US008372620B2

(12) United States Patent
Sibbesen et al.

(10) Patent No.: US 8,372,620 B2
(45) Date of Patent: Feb. 12, 2013

(54) BACTERIAL XYLANASES

(75) Inventors: Ole Sibbesen, Bagsvaerd (DK); Jens Frisbaek Sorensen, Aarhus (DK)

(73) Assignee: DuPont Nutrition Biosciences ApS, Copenhagen K (DK)

( * ) Notice: Subject to any disclaimer, the term of this patent is extended or adjusted under 35 U.S.C. 154(b) by 776 days.

(21) Appl. No.: 10/626,583

(22) Filed: Jul. 25, 2003

(65) Prior Publication Data

US 2004/0234998 A1 Nov. 25, 2004

Related U.S. Application Data

(63) Continuation of application No. 09/869,155, filed as application No. PCT/IB99/02071 on Dec. 17, 1999, now abandoned.

(30) Foreign Application Priority Data

| Dec. 23, 1998 | (GB) | .................................. | 9828599.2 |
| Apr. 6, 1999 | (GB) | .................................. | 9907805.7 |
| Apr. 15, 1999 | (GB) | .................................. | 9908645.6 |

(51) Int. Cl.
*C12N 9/42* (2006.01)
*C12N 9/14* (2006.01)
*C12P 21/06* (2006.01)
*C07H 21/04* (2006.01)
*C07K 1/00* (2006.01)

(52) U.S. Cl. ......... 435/209; 435/195; 435/69.1; 426/20; 536/23.2; 530/350

(58) Field of Classification Search .................. 435/4, 6, 435/69–1, 183, 200, 252–3, 320–1, 209, 435/195; 426/549, 20; 536/23–2, 23–7, 536/23.2; 530/350
See application file for complete search history.

(56) References Cited

U.S. PATENT DOCUMENTS

| 3,512,992 | A | | 5/1970 | Cooke et al. |
| 5,176,927 | A | * | 1/1993 | Haarasilta et al. ............... 426/20 |
| 5,306,633 | A | | 4/1994 | Gottschalk et al. |
| 5,405,769 | A | * | 4/1995 | Campbell et al. ............. 435/200 |
| 6,346,407 | B1 | | 2/2002 | De Buyl et al. |

FOREIGN PATENT DOCUMENTS

| EP | 0096430 | 12/1983 |
| EP | 120516 | 10/1984 |
| EP | 0134048 | 3/1985 |
| EP | 0184438 | 6/1986 |
| EP | 0284603 | 10/1986 |
| EP | 0253455 | 1/1988 |
| EP | 0301670 | 2/1989 |
| EP | 0449374 | 10/1991 |
| EP | 0 698 667 A1 | 2/1996 |
| EP | 0 828 002 | 3/1998 |
| EP | 0 979 830 | 2/2000 |
| WO | WO 83/04050 A1 | 11/1983 |
| WO | WO 86/06097 A1 | 10/1986 |
| WO | WO 95/23515 | 9/1995 |
| WO | WO 96/39851 | 12/1996 |
| WO | WO 98/49278 | 11/1998 |

OTHER PUBLICATIONS

Paice et al. Accession No. P18429, UnitProt Database, 1990.*
Wolf et al. Accession No. I40569, PIR Database, 1996.*
Wolf et al. and Poutanen (Trends in Food Science and Technol., 1997, vol. 8(300-306).*
Paice et al., A xylanase gene from *Bacillus subtilis*: nucleotide sequence and comparison with *B. pumilus* gene. Arch. Microbiol. 1986, vol. 144: 201-206.*
Poutanene K., Enzymes: An important tool in the improvement of the quality of cereal foods. Trends in Food Svi. & Technol., 1997, vol. 8: 300-306.*
Autio et al., Effects of purified endo-b-xylanase and endo-b-glucanase on the structural and baking characteristics of rye doughs. Academic Press, 1996, pp. 18-27.*
McLauchlan, W. Russell et al., "A novel class of protein from wheat which inhibits xylanases1", *Biochem. J.*, © 1999 Biochemical Society, pp. 441-446, (1999).
Debyser, W. et al., "*Triticum aestivum* Xylanase Inhibitor (TAXI), a New Class of Enxyme Inhibitor Affecting Breadmaking Performance", *Journal of Cereal Science*, 30, © Academic Press, pp. 39-43, (1999).
Paice, Michael G. et al., "A xylanase gene from *Bacillus subtilis*: nucleotide sequence and comparison with *B. pumilus* gene", *Arch Microbiol.*, 144, © Springer-Verlag 1986, pp. 201-206, (1986).
Wolf, Monika et al., "Genes encoding xylan and β-glucan hydrolysing enzymes in *Bacillus subtilis*: characterization, mapping and construction of strains deficient in lichenase, cellulase and xylanase", *Microbiology*, 141., pp. 281-290, (1995).
Yu, Ju-Hyun et al, "Nucleotide Sequence and Analysis of a Xylanase gene (*xynS*) from Alkali-tolerant *Bacillus* sp. YA-14 and Comparison with Other Xylanases", *Journal of Microbiology and Biotechnology*, vol. 3, No. 3, pp. 139-145, (1993).
Yang, Robert C. et al., "Nucleotide sequence of a *Bacillus circulans* xylanase gene", *Nucleic Acids Research*, vol. 16, No. 14, © IRL Press Limited, p. 7187, (1988).
Rouau, X. et al., "Evidence for the Presence of a Pentosanase Inhibitor in Wheat Flours", *Journal of Cerial Science*, 28, © 1998 Academic Press, pp. 63-70, (1998).
Debyser, Winok et al, "Arabinoxylan Solubilization and Inhibition of the Barley Malt Xylanolytic System by Wheat During Mashing with Wheat Wholemeal Adjunct: Evidence for a New Class of Enzyme Inhibitors in Wheat", *J. Am Soc. Brew. Chem.*, 55(4) pp. 153-166, (1997).
Maat et al., "Xylanases and their application in bakery," *Xylans and Xylanases* (1992), J. Visser et al., ed., pp. 349-360, Elsevier Science Publishers B.V.
Fincher et al., "Cell Walls and Their Components in Cereal Grain Technology," *Advances in Cereal Technology*, (1986), vol. VIII (Pomeranz, ed.), AACC, St. Paul, Minnesota, pp. 207-295.
Meuser et al., "Non-starch Polysaccharides," *Chemistry and Physics of Baking*, (1985), Royal Society of Chemistry, London, pp. 42-61.
McCleary, "Enzymatic modification of plant polysaccharides," *International Journal of Bilogical Macro Molecules*, (1986) vol. 8, pp. 349-354, Butterworth & Co.

(Continued)

*Primary Examiner* — Ganapathirama Raghu

(74) *Attorney, Agent, or Firm* — Steptoe & Johnson LLP

(57) ABSTRACT

An improved dough for preparing bakery products is made by substituting a bacterial xylanase for the usual fungal xylanase, resulting in a dough which is less sticky. Suitable bacterial xylanases and xylanase inhibitors are identified.

16 Claims, 22 Drawing Sheets

OTHER PUBLICATIONS

Figure 1:
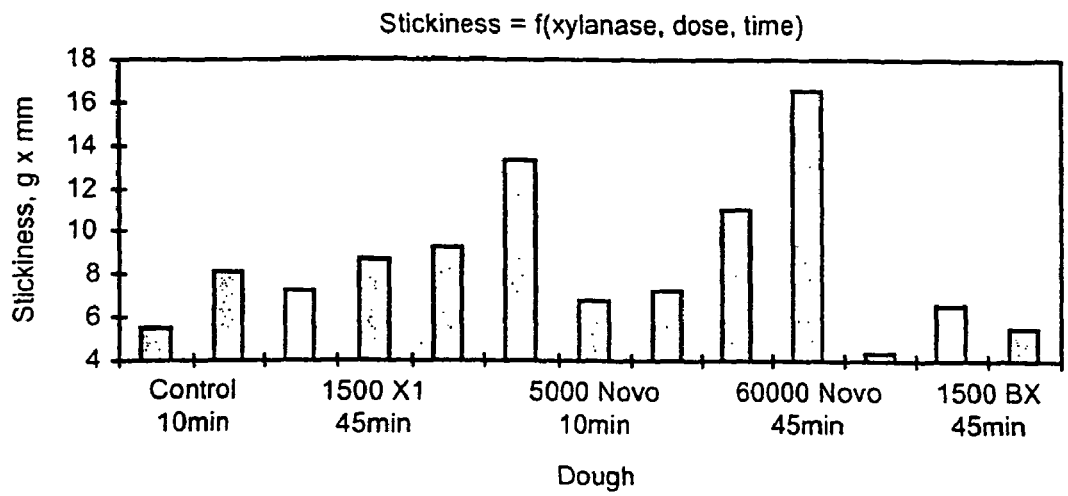

Sleat et al., "Characterisation of the 5'-leader sequence of tobacco mosaic virus RNA as a general enhancer of translation in vitro," *Gene* (1987), vol. 217, pp. 217-225, Elsevier Science Publishers B.V.

Dowson Day et al., "Plant viral leaders influence expression of a reporter gene in tobacco," *Plant Mol. Biol.* (1993), vol. 23, pp. 97-109, Kluwer Academic Publishers.

An et al., "Transformation of Tobacco, Tomato, Potato and *Arabidopsis thaliana* Using a Binary Ti Vector System," *Plant Physiol.* (1986), vol. 81, pp. 301-305.

Butcher et al., "The role of tissue culture in the study of crown-gall tumorigenesis," *Tissue Culture Methods for Plant Pathologists* (1980), pp. 203-208.

Potrykus, "Gene Transfer to Plants: Assessment of Published Approaches and Results," *Annu. Rev. Plant Physiol Plant Mol.Biol* (1991), vol. 42, pp. 205-225.

Winter et al., "Man-made antibodies," *Nature* (1991), vol. 349, pp. 293-299.

Orlandi et al., "Cloning immunoglobulin variable domains for expression by the polymerase chain reaction," *Proc Natl. Acad. Sci.* (1989), vol. 86, pp. 3833-3837.

Takeda et al., "Construction of chimaeric processed immunoglobulin genes containing mouse variable and human constant region sequences," *Nature* (1985), vol. 314, pp. 452-454.

Neuberger et al., "Recombinant antibodies possessing novel effector functions," *Nature* (1984), vol. 312, pp. 604-608.

Morrison et al., "Chimeric human antibody molecules: Mouse antigen-binding domains with human constant region domains," *Proc. Natl. Acad. Sci.* (1984), vol. 81, pp. 6851-6855.

Cole et al., "The EBV-Hybridoma Technique and its application to human lung cancer," *Monoclonal Antibodies and Cancer Therapy* (1985), Reisfeld et al., ed., pp. 77-96.

Cote et al., "Generation of human monoclonal antibodies reactive with cellular antigens," *Proc. Natl Acad. Sci.* (1983), vol. 80, pp. 2026-2030.

Kozbor et al., "The production of monoclonal antibodies from human lymphocytes," *Immunol Today* (1983), vol. 4, No. 3, pp. 72-79.

Koehler et al., "Continuous cultures of fused cells secreting antibody of predefined specificity," *Nature* (1975), vol. 256, pp. 495-497.

Veron Special Product Specification, 1995, 2 pgs.

Solutions to the Bromate Problem, Asia pacific Baker, Jul./Aug. 14-15, 1998, 3 pgs.

Ehlers, "Developing Enzyme Influence," *Food Ingred. Anal. Int*, vol. 18, No. 1, pp. 22-23 (1996).

Notice of Reasons for Refusal cited in related Japanese Patent Application No. 2000-591181, dated Aug. 6, 2009.

McCleary, et al., "Enzymatic modification of plant polysaccharides," Int. J. Biol. Macromol., vol. 8, pp. 349-354, Dec. (1986).

* cited by examiner

SEQUENCE LISTING

<160> NUMBER OF SEQ ID NOS: 19

<210> SEQ ID NO 1
<211> LENGTH: 57
<212> TYPE: PRT
<213> ORGANISM: Artificial Sequence
<220> FEATURE:
<221> NAME/KEY: MOD_RES
<222> LOCATION: (17)
<223> OTHER INFORMATION: Any Amino Acid
<220> FEATURE:
<221> NAME/KEY: MOD_RES
<222> LOCATION: (43)
<223> OTHER INFORMATION: Any Amino Acid
<221> NAME/KEY: MOD_RES
<222> LOCATION: (49)
<223> OTHER INFORMATION: Any Amino Acid
<220> FEATURE:
<223> OTHER INFORMATION: Description of Artificial Sequence: Synthetic
      Xylanase Inhibitor

<400> SEQUENCE: 1

Leu Ala Val Val Ala Arg Ala Val Lys Asp Val Ala Pro Phe Gly Val
1               5                   10                  15

Xaa Tyr Asp Thr Lys Thr Leu Gly Asn Asn Leu Gly Gly Tyr Ala Val
            20                  25                  30

Pro Asn Gln Leu Gly Leu Leu Asp Gly Gly Xaa Asp Trp Thr Met Ile
        35                  40                  45

Xaa Lys Asn Ser Met Val Asp Val Lys
    50                  55

<210> SEQ ID NO 2
<211> LENGTH: 38
<212> TYPE: PRT
<213> ORGANISM: Artificial Sequence
<220> FEATURE:
<221> NAME/KEY: MOD_RES
<222> LOCATION: (26)
<223> OTHER INFORMATION: Any Amino Acid
<220> FEATURE:
<221> NAME/KEY: MOD_RES
<222> LOCATION: (31)
<223> OTHER INFORMATION: Any Amino Acid
<220> FEATURE:
<221> NAME/KEY: MOD_RES
<222> LOCATION: (34)
<223> OTHER INFORMATION: Any Amino Acid
<221> NAME/KEY: MOD_RES
<222> LOCATION: (38)
<223> OTHER INFORMATION: Any Amino Acid
<220> FEATURE:
<223> OTHER INFORMATION: Description of Artificial Sequence: Synthetic
      Xylanase Inhibitor

<400> SEQUENCE: 2

Gly Pro Pro Leu Ala Pro Val Thr Glu Ala Pro Ala Thr Ser Leu Tyr
1               5                   10                  15

Thr Ile Pro Phe His His Gly Ala Ala Xaa Val Leu Asp Val Xaa Ser
            20                  25                  30

Ser Xaa Leu Leu Trp Xaa
        35

<210> SEQ ID NO 3
<211> LENGTH: 213
<212> TYPE: PRT
<213> ORGANISM: Unknown Organism
<220> FEATURE:
<223> OTHER INFORMATION: Description of Unknown Organism: Xylanase

<400> SEQUENCE: 3

```
Met Phe Lys Phe Lys Lys Lys Phe Leu Val Gly Leu Thr Ala Ala Phe
 1               5                  10                  15
Met Ser Ile Ser Met Phe Ser Ala Thr Ala Ser Ala Ala Gly Thr Asp
             20                  25                  30
Tyr Trp Gln Asn Trp Thr Asp Gly Gly Gly Thr Val Asn Ala Val Asn
         35                  40                  45
Gly Ser Gly Gly Asn Tyr Ser Val Asn Trp Ser Asn Thr Gly Asn Phe
     50                  55                  60
Val Val Gly Lys Gly Trp Thr Thr Gly Ser Pro Phe Arg Thr Ile Asn
 65                  70                  75                  80
Tyr Asn Ala Gly Val Trp Ala Pro Asn Gly Asn Gly Tyr Leu Thr Leu
                 85                  90                  95
Tyr Gly Trp Thr Arg Ser Pro Leu Ile Glu Tyr Tyr Val Val Asp Ser
            100                 105                 110
Trp Gly Thr Tyr Arg Pro Thr Gly Thr Tyr Lys Gly Thr Val Lys Ser
        115                 120                 125
Asp Gly Gly Thr Tyr Asp Ile Tyr Thr Thr Arg Tyr Asn Ala Pro
    130                 135                 140
Ser Ile Asp Gly Asp Asn Thr Thr Phe Thr Gln Tyr Trp Ser Val Arg
145                 150                 155                 160
Gln Ser Lys Arg Pro Thr Gly Ser Asn Ala Ala Ile Thr Phe Ser Asn
                165                 170                 175
His Val Asn Ala Trp Lys Ser His Gly Met Asn Leu Gly Ser Asn Trp
            180                 185                 190
Ala Tyr Gln Val Leu Ala Thr Glu Gly Tyr Lys Ser Ser Gly Ser Ser
        195                 200                 205
Asn Val Thr Val Trp
    210
```

<210> SEQ ID NO 4
<211> LENGTH: 642
<212> TYPE: DNA
<213> ORGANISM: Unknown Organism
<220> FEATURE:
<223> OTHER INFORMATION: Description of Unknown Organism: Xylanase

<400> SEQUENCE: 4

```
atgtttaagt ttaaaaagaa attcttagtt ggattaacgg cagctttcat gagtatcagc      60
atgttttcgg caaccgcctc tgcagctggc acagattact ggcaaaattg gactgacggg     120
ggcgggacag taaacgcagt caatggctct ggcggaaatt acagtgttaa ttggtctaat     180
accgggaatt tcgttgttgg taaaggctgg actacaggct cgccatttag aacaataaac     240
tataatgccg gtgtttgggc gccgaatggc aatggatatt taactttata tggctggacg     300
agatcgcccc tcatcgaata ttatgtgtg gattcatggg gtacttacag acctaccgga     360
acgtataaag gtaccgtaaa gagtgatgga ggtacatatg acatatatac aacgacacgt     420
tataacgcac cttccattga tggcgataac actacttta cgcagtactg gagtgtccgc     480
cagtcgaaga gaccgaccgg aagcaacgct gcaatcactt tcagcaatca tgttaacgca     540
tggaagagcc atggaatgaa tctgggcagt aattgggctt atcaagtctt agcgacagaa     600
ggatataaaa gcagcggaag ttctaatgta acagtgtggt aa                        642
```

<210> SEQ ID NO 5
<211> LENGTH: 213

<212> TYPE: PRT
<213> ORGANISM: Bacillus subtilis

<400> SEQUENCE: 5

```
Met Phe Lys Phe Lys Lys Asn Phe Leu Val Gly Leu Ser Ala Ala Leu
 1               5                  10                  15

Met Ser Ile Ser Leu Phe Ser Ala Thr Ala Ser Ala Ala Ser Thr Asp
             20                  25                  30

Tyr Trp Gln Asn Trp Thr Asp Gly Gly Gly Ile Val Asn Ala Val Asn
         35                  40                  45

Gly Ser Gly Gly Asn Tyr Ser Val Asn Trp Ser Asn Thr Gly Asn Phe
     50                  55                  60

Val Val Gly Lys Gly Trp Thr Thr Gly Ser Pro Phe Arg Thr Ile Asn
 65                  70                  75                  80

Tyr Asn Ala Gly Val Trp Ala Pro Asn Gly Asn Gly Tyr Leu Thr Leu
                 85                  90                  95

Tyr Gly Trp Thr Arg Ser Pro Leu Ile Glu Tyr Tyr Val Val Asp Ser
            100                 105                 110

Trp Gly Thr Tyr Arg Pro Thr Gly Thr Tyr Lys Gly Thr Val Lys Ser
        115                 120                 125

Asp Gly Gly Thr Tyr Asp Ile Tyr Thr Thr Thr Arg Tyr Asn Ala Pro
    130                 135                 140

Ser Ile Asp Gly Asp Arg Thr Thr Phe Thr Gln Tyr Trp Ser Val Arg
145                 150                 155                 160

Gln Ser Lys Arg Pro Thr Gly Ser Asn Ala Thr Ile Thr Phe Ser Asn
                165                 170                 175

His Val Asn Ala Trp Lys Ser His Gly Met Asn Leu Gly Ser Asn Trp
            180                 185                 190

Ala Tyr Gln Val Met Ala Thr Glu Gly Tyr Gln Ser Ser Gly Ser Ser
        195                 200                 205

Asn Val Thr Val Trp
    210
```

<210> SEQ ID NO 6
<211> LENGTH: 642
<212> TYPE: DNA
<213> ORGANISM: Bacillus subtilis

<400> SEQUENCE: 6

```
atgtttaagt ttaaaaagaa tttcttagtt ggattatcgg cagctttaat gagtattagc    60
ttgttttcgg caaccgcctc tgcagctagc acagactact ggcaaaattg gactgatggg   120
ggcggtatag taaacgctgt caatgggtct ggcgggaatt acagtgttaa ttggtctaat   180
accggaaatt tgttgttgg taaaggttgg actacaggtt cgccatttag gacgataaac   240
tataatgccg gagtttgggc gccgaatggc aatggatatt taactttata tggttggacg   300
agatcacctc tcatagaata ttatgtagtg gattcatggg gtacttatag acctactgga   360
acgtataaag gtactgtaaa aagtgatggg ggtacatatg acatatatac aactacacgt   420
tataacgcac cttccattga tggcgatcgc actactttta cgcagtactg gagtgttcgc   480
cagtcgaaga gaccaaccgg aagcaacgct acaatcactt tcagcaatca tgtgaacgca   540
tggaagagcc atggaatgaa tctgggcagt aattgggctt accaagtcat ggcgacagaa   600
ggatatcaaa gtagtggaag ttctaacgta acagtgtggt aa                     642
```

<210> SEQ ID NO 7
<211> LENGTH: 213

<210> SEQ ID NO 7
<211> LENGTH: 210
<212> TYPE: PRT
<213> ORGANISM: Artificial Sequence
<220> FEATURE:
<223> OTHER INFORMATION: Description of Artificial Sequence: Synthetic Mutant Xylanase

<400> SEQUENCE: 7

```
Met Phe Lys Phe Lys Lys Asn Phe Leu Val Gly Leu Ser Ala Ala Leu
1               5                   10                  15

Met Ser Ile Ser Leu Phe Ser Ala Thr Ala Ser Ala Ala Ser Thr Asp
            20                  25                  30

Tyr Trp Gln Asn Trp Thr Asp Gly Gly Gly Thr Val Asn Ala Val Asn
        35                  40                  45

Gly Ser Gly Gly Asn Tyr Ser Val Asn Trp Ser Asn Thr Gly Asn Phe
    50                  55                  60

Val Val Gly Lys Gly Trp Thr Thr Gly Ser Pro Phe Arg Thr Ile Asn
65                  70                  75                  80

Tyr Asn Ala Gly Val Trp Ala Pro Asn Gly Asn Gly Tyr Leu Thr Leu
                85                  90                  95

Tyr Gly Trp Thr Arg Ser Pro Leu Ile Glu Tyr Tyr Val Val Asp Ser
            100                 105                 110

Trp Gly Thr Tyr Arg Pro Thr Gly Thr Tyr Lys Gly Thr Val Lys Ser
        115                 120                 125

Asp Gly Gly Thr Tyr Asp Ile Tyr Thr Thr Thr Arg Tyr Asn Ala Pro
    130                 135                 140

Ser Ile Asp Gly Asp Arg Thr Thr Phe Thr Gln Tyr Trp Ser Val Arg
145                 150                 155                 160

Gln Ser Lys Arg Pro Thr Gly Ser Asn Ala Ala Ile Thr Phe Ser Asn
                165                 170                 175

His Val Asn Ala Trp Lys Ser His Gly Met Asn Leu Gly Ser Asn Trp
            180                 185                 190

Ala Tyr Gln Val Leu Ala Thr Glu Gly Tyr Lys Ser Ser Gly Ser Ser
        195                 200                 205

Asn Val Thr Val Trp
    210
```

<210> SEQ ID NO 8
<211> LENGTH: 642
<212> TYPE: DNA
<213> ORGANISM: Artificial Sequence
<220> FEATURE:
<223> OTHER INFORMATION: Description of Artificial Sequence: Synthetic Mutant Xylanase

<400> SEQUENCE: 8

```
atgtttaagt ttaaaaagaa tttcttagtt ggattatcgg cagctttaat gagtattagc      60
ttgttttcgg caaccgcctc tgcagctagc acagactact ggcaaaattg gactgatggg     120
ggcggtaccg taaacgctgt caatgggtct ggcgggaatt acagtgttaa ttggtctaat     180
accggaaatt ttgttgttgg taaaggttgg actacaggtt cgccatttag gacgataaac     240
tataatgccg gagtttgggc gccgaatggc aatggatatt taactttata tggttggacg     300
agatcaccct ctatagaata ttatgtagtg gattcatggg gtacttatag acctactgga     360
acgtataaag gtactgtaaa aagtgatggg ggtacatatg acatatatac aactacacgt     420
tataacgcac cttccattga tggcgatcgc actactttta cgcagtactg gagtgttcgc     480
cagtcgaaga gaccaaccgg aagcaacgct gctatcactt tcagcaatca tgtgaacgca     540
tggaagagcc atggaatgaa tctgggcagt aattgggctt accaagtcct cgcgacagaa     600
```
ggatataaaa gttccggaag ttctaacgta acagtgtggt aa         642

<210> SEQ ID NO 9
<211> LENGTH: 213
<212> TYPE: PRT
<213> ORGANISM: Artificial Sequence
<220> FEATURE:
<223> OTHER INFORMATION: Description of Artificial Sequence: Synthetic
      Mutant Xylanase

<400> SEQUENCE: 9

Met Phe Lys Phe Lys Lys Asn Phe Leu Val Gly Leu Ser Ala Ala Leu
 1               5                  10                  15

Met Ser Ile Ser Leu Phe Ser Ala Thr Ala Ser Ala Ala Ser Thr Asp
            20                  25                  30

Tyr Trp Gln Asn Trp Thr Asp Gly Gly Gly Thr Val Asn Ala Val Asn
        35                  40                  45

Gly Ser Gly Gly Asn Tyr Ser Val Asn Trp Ser Asn Thr Gly Asn Phe
    50                  55                  60

Val Val Gly Lys Gly Trp Thr Thr Gly Ser Pro Phe Arg Thr Ile Asn
65                  70                  75                  80

Tyr Asn Ala Gly Val Trp Ala Pro Asn Gly Asn Gly Tyr Leu Thr Leu
                85                  90                  95

Tyr Gly Trp Thr Arg Ser Pro Leu Ile Glu Tyr Tyr Val Val Asp Ser
            100                 105                 110

Trp Gly Thr Tyr Arg Pro Thr Gly Thr Tyr Lys Gly Thr Val Lys Ser
        115                 120                 125

Asp Gly Gly Thr Tyr Asp Ile Tyr Thr Thr Thr Arg Tyr Asn Ala Pro
    130                 135                 140

Ser Ile Asp Gly Asp Asn Thr Thr Phe Thr Gln Tyr Trp Ser Val Arg
145                 150                 155                 160

Gln Ser Lys Arg Pro Thr Gly Ser Asn Ala Ala Ile Thr Phe Ser Asn
                165                 170                 175

His Val Asn Ala Trp Lys Ser His Gly Met Asn Leu Gly Ser Asn Trp
            180                 185                 190

Ala Tyr Gln Val Leu Ala Thr Glu Gly Tyr Lys Ser Ser Gly Ser Ser
        195                 200                 205

Asn Val Thr Val Trp
    210

<210> SEQ ID NO 10
<211> LENGTH: 642
<212> TYPE: DNA
<213> ORGANISM: Artificial Sequence
<220> FEATURE:
<223> OTHER INFORMATION: Description of Artificial Sequence: Synthetic
      Mutant Xylanase

<400> SEQUENCE: 10
atgtttaagt ttaaaaagaa tttcttagtt ggattatcgg cagctttaat gagtattagc         60
ttgttttcgg caaccgcctc tgcagctagc acagactact gcaaaattg gactgatggg        120 ggcggtaccg taaacgctgt caatgggtct ggcgggaatt acagtgttaa ttggtctaat        180
accggaaatt ttgttgttgg taaggttgg actacaggtt cgccatttag acgataaac        240 tataatgccg gagtttgggc gccgaatggc aatggatatt taactttata tggttggacg        300
agatcacctc tcatagaata ttatgtagtg gattcatggg gtacttatag acctactgga        360
acgtataaag gtactgtaaa aagtgatggg ggtacatatg acatatatac aactacacgt        420
tataacgcac cttccattga tggcgataat actactttta cgcagtactg gagtgttcgc    480
cagtcgaaga gaccaaccgg aagcaacgct gctatcactt tcagcaatca tgtgaacgca    540
tggaagagcc atggaatgaa tctgggcagt aattgggctt accaagtcct cgcgacagaa    600
ggatataaaa gttccggaag ttctaacgta acagtgtggt aa                        642

<210> SEQ ID NO 11
<211> LENGTH: 213
<212> TYPE: PRT
<213> ORGANISM: Artificial Sequence
<220> FEATURE:
<223> OTHER INFORMATION: Description of Artificial Sequence: Synthetic
      Mutant Xylanase

<400> SEQUENCE: 11

Met Phe Lys Phe Lys Lys Asn Phe Leu Val Gly Leu Ser Ala Ala Leu
 1               5                  10                  15

Met Ser Ile Ser Leu Phe Ser Ala Thr Ala Ser Ala Ala Ser Thr Asp
            20                  25                  30

Tyr Trp Gln Asn Trp Thr Asp Gly Gly Gly Thr Val Asn Ala Val Asn
        35                  40                  45

Gly Ser Gly Gly Asn Tyr Ser Val Asn Trp Ser Asn Thr Gly Asn Phe
    50                  55                  60

Val Val Gly Lys Gly Trp Thr Thr Gly Ser Pro Phe Arg Thr Ile Asn
65                  70                  75                  80

Tyr Asn Ala Gly Val Trp Ala Pro Asn Gly Asn Gly Tyr Leu Thr Leu
                85                  90                  95

Tyr Gly Trp Thr Arg Ser Pro Leu Ile Glu Tyr Tyr Val Val Asp Ser
            100                 105                 110

Trp Gly Thr Tyr Arg Pro Thr Gly Thr Tyr Lys Gly Thr Val Lys Ser
        115                 120                 125

Asp Gly Gly Thr Tyr Asp Ile Tyr Thr Thr Thr Arg Tyr Asn Ala Pro
    130                 135                 140

Ser Ile Asp Gly Asp Asn Thr Thr Phe Thr Gln Tyr Trp Ser Val Arg
145                 150                 155                 160

Gln Ser Lys Arg Pro Thr Gly Ser Asn Ala Thr Ile Thr Phe Ser Asn
                165                 170                 175

His Val Asn Ala Trp Lys Ser His Gly Met Asn Leu Gly Ser Asn Trp
            180                 185                 190

Ala Tyr Gln Val Met Ala Thr Glu Gly Tyr Gln Ser Ser Gly Ser Ser
        195                 200                 205

Asn Val Thr Val Trp
    210

<210> SEQ ID NO 12
<211> LENGTH: 642
<212> TYPE: DNA
<213> ORGANISM: Artificial Sequence
<220> FEATURE:
<223> OTHER INFORMATION: Description of Artificial Sequence: Synthetic
      Mutant Xylanase

<400> SEQUENCE: 12
atgtttaagt ttaaaaagaa tttcttagtt ggattatcgg cagctttaat gagtattagc     60
ttgttttcgg caaccgcctc tgcagctagc acagactact ggcaaaattg gactgatggg    120
ggcggtaccg taaacgctgt caatgggtct ggcgggaatt acagtgttaa ttggtctaat    180
accggaaatt ttgttgttgg taaaggttgg actacaggtt cgccatttag gacgataaac    240

```
tataatgccg agtttgggc gccgaatggc aatggatatt taactttata tggttggacg    300
agatcacctc tcatagaata ttatgtagtg gattcatggg gtacttatag acctactgga    360
acgtataaag gtactgtaaa aagtgatggg ggtacatatg acatatatac aactacacgt    420
tataacgcac cttccattga tggcgataat actactttta cgcagtactg gagtgttcgc    480
cagtcgaaga gaccaaccgg aagcaacgct acaatcactt tcagcaatca tgtgaacgca    540
tggaagagcc atggaatgaa tctgggcagt aattgggctt accaagtcat ggcgacagaa    600
ggatatcaaa gtagtggaag ttctaacgta acagtgtggt aa                      642
```

```
<210> SEQ ID NO 13
<211> LENGTH: 35
<212> TYPE: PRT
<213> ORGANISM: Artificial Sequence
<220> FEATURE:
<223> OTHER INFORMATION: Description of Artificial Sequence: Synthetic
      Xylanase Inhibitor

<400> SEQUENCE: 13

Gly Ala Pro Val Ala Arg Ala Val Glu Ala Val Ala Pro Phe Gly Val
  1               5                  10                  15

Cys Tyr Asp Thr Lys Thr Leu Gly Asn Asn Leu Gly Gly Tyr Ala Val
             20                  25                  30

Pro Asn Val
         35

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      Xylanase Inhibitor

<400> SEQUENCE: 14

Lys Arg Leu Gly Phe Ser Arg Leu Pro His Phe Thr Gly Cys Gly Gly
  1               5                  10                  15

Leu

<210> SEQ ID NO 15
<211> LENGTH: 21
<212> TYPE: PRT
<213> ORGANISM: Artificial Sequence
<220> FEATURE:
<223> OTHER INFORMATION: Description of Artificial Sequence: Synthetic
      Xylanase Inhibitor

<400> SEQUENCE: 15

Leu Pro Val Pro Ala Pro Val Thr Lys Asp Pro Ala Thr Ser Leu Tyr
  1               5                  10                  15

Thr Ile Pro Phe His
             20

<210> SEQ ID NO 16
<211> LENGTH: 31
<212> TYPE: PRT
<213> ORGANISM: Artificial Sequence
<220> FEATURE:
<223> OTHER INFORMATION: Description of Artificial Sequence: Synthetic
      Xylanase Inhibitor

<400> SEQUENCE: 16

Leu Leu Ala Ser Leu Pro Arg Gly Ser Thr Gly Val Ala Gly Leu Ala
```

```
                1               5              10              15

Asn Ser Gly Leu Ala Leu Pro Ala Gln Val Ala Ser Ala Gln Lys
                        20                  25                  30

<210> SEQ ID NO 17
<211> LENGTH: 24
<212> TYPE: PRT
<213> ORGANISM: Artificial Sequence
<220> FEATURE:
<223> OTHER INFORMATION: Description of Artificial Sequence: Synthetic
      Xylanase Inhibitor

<400> SEQUENCE: 17

Gly Gly Ser Pro Ala His Tyr Ile Ser Ala Arg Phe Ile Glu Val Gly
  1               5                  10                  15

Asp Thr Arg Val Pro Ser Val Glu
                20

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      Xylanase Inhibitor

<400> SEQUENCE: 18

Val Asn Val Gly Val Leu Ala Ala Cys Ala Pro Ser Lys
  1               5                  10

<210> SEQ ID NO 19
<211> LENGTH: 41
<212> TYPE: PRT
<213> ORGANISM: Artificial Sequence
<220> FEATURE:
<223> OTHER INFORMATION: Description of Artificial Sequence: Synthetic
      Xylanase Inhibitor

<400> SEQUENCE: 19

Val Ala Asn Arg Phe Leu Leu Cys Leu Pro Thr Gly Gly Pro Gly Val
  1               5                  10                  15

Ala Ile Phe Gly Gly Gly Pro Val Pro Trp Pro Gln Phe Thr Gln Ser
                20                  25                  30

Met Pro Tyr Thr Leu Val Val Val Lys
                35                  40
```

BACTERIAL XYLANASES

CROSS-REFERENCE TO RELATED APPLICATIONS

The present application is a continuation of U.S. patent application Ser. No. 09/869,155, filed Oct. 1, 2001, now abandoned, which is a National Stage of International Patent Application No. PCT/IB99/02071, filed Dec. 17, 1999, which was published in English.

BACKGROUND OF THE PRESENT INVENTION

The present invention relates to proteins.

In particular, the present invention relates to the isolation of and characterisation of an endogenous endo-β-1,4-xylanase inhibitor that is present in wheat flour and its effect on different xylanases. The present invention also relates to xylanases identified by a screen using the inhibitor and to novel xylanases identified thereby.

BACKGROUND ART

Xylanases have been used in bakery for several years.

In this regard, it is known that wheat flour contains arabinoxylan originating from the endosperm cell walls. The amount of arabinoxylan in the flour differs depending on the origin of the flour—for example, see Rouau et al, Journal of Cereal Science (1994), 19, 259-272 *Effect of an Enzyme Preparation Containing Pentosanases on the Bread-making Quality of Flour in Relation to Changes in Pentosan Properties*; Fincher and Stone, (1986) *Advances in Cereal Technology*, Vol. VIII (Why Pomeranz, Ed.) AACC, St Paul, Minn., 207-295; and Meuser and Suckow (1986). *Chemistry and Physics of Baking* (J. M. V. Blanchard, P J Frasier and T Gillard, Eds.) Royal Society of Chemistry, London, 42-61. Typically the amount of arabinoxylan can vary from 2-5% ((w/w) based on flour dry weight).

Fincher and Stone (1986) report 70% of the polysaccharides in the endosperm cell wall are arabinoxylan. A characteristic feature of arabinoxylan is its ability to bind to water. Part of the arabinoxylan is water insoluble pentosan (WIP) and part is water soluble pentosan (WSP). Experimental results have shown a correlation between degradation of WIP to high molecular weight (HMW) water soluble polymers and bread volume.

During the production of a bakery product, it is known that using a xylanase at a proper dosage may result in a more stable dough system (which will typically comprise salt, flour, yeast and water) and a better volume of, for example, raised bread.

In this respect, a good xylanase for increasing bread volume should solubilise WIP giving an increased viscosity in the dough liquid without further degradation of WSP into xylose oligomers. This degradation of WIP into low molecular weight (LMW) WSP is believed to be detrimental for the dough properties and may give rise to stickiness (Rouau et al and McCleary (1986) *International Journal of Biological Macro Molecules*, 8, 349-354).

U.S. Pat. No. 5,306,633 discloses a xylanase obtained from a *Bacillus subtilis* strain. Apparently, this xylanase may improve the consistency and increase the volume of bread and baked goods containing the same.

Another xylanase from *Bacillus subtilis* has been isolated and sequenced (see Paice, M. G., Bourbonnais, R., Desrochers, M., Jurasek, L. and Yaguchi, M. A xylanase gene from *Bacillus subtilis*: nucleotide sequence and comparison with *B. pumilus* gene, Arch. Microbiol. 144, 201-206 (1986)).

It has been considered for some time now that bacterial xylanases would produce very sticky dough. Hence, one would normally expect the xylanases of *Bacillus subtilis*—such as that of U.S. Pat. No. 5,306,633—to produce a very sticky dough.

Prior art enzymes which caused stickiness had to be used in carefully controlled amounts so that stickiness would not adversely affect handling to such a degree that effective commercial handling was hampered. However, the need to carefully control dosage prohibited the addition of xylanase directly to flour prior to production of the dough. It was therefore necessary with prior art systems to add the xylanase in a very controlled manner during the production of the dough.

To date, fungal xylanases have been typically used in baking. For example, J Maat et al. (Xylans and Xylanases, edited by J Visser et al, 349-360, *Xylanases and their application in bakery*) teach a β-1,4-xylanase produced by an *Aspergillus Niger* var. *awarmori* strain. According to these authors, the fungal xylanase is effective in increasing the specific volume of breads, without giving rise to a negative side effect on dough handling (stickiness of the dough) as can be observed with xylanases derived from other fungal or from bacterial sources.

It has been proposed by W Debyser et al., (J. Am. Soc. Brew. Ch m. 55(4), 153-156, 1997, *Arabinoxylan Solubilization and Inhibition of the Barely Malt Xylanolytic System by Wheat During Mashing with Wheat Wholemeal Adjunt: Evidence for a New Class of Enzyme Inhibitors in Wheat*), that xylanase inhibitors may be present in wheat. The inhibitor discussed by W Debyser et al. was not isolated. Furthermore, it is not disclosed by W Debyser et al. whether the inhibitor is endogenous or microbiological. Moreover, no chemical data were presented for this inhibitor.

The presence of xylanase inhibitor in wheat flour has also recently been discussed by X Rouau and A Surget, (Journal of Cereal Science, 28 (1998) 63-70, *Evidence for the Presence of a Pentosanase Inhibitor in Wheat Flours*). Similar to Debyser et al., Rouau and Surget believed that they have identified the existence of a thermolabile compound in the soluble fraction of wheat flours, which limited the action of an added pentosanase. Also similarly to Debyser et al., these authors did not isolate an inhibitor and were unable to conclude whether the inhibitor is endogenous or is of microbial origin. Likewise, no chemical data were presented for this inhibitor.

Thus, a known problem in the art is how to prepare baked goods from a dough which does not have adverse handling properties. A more particular problem is how to provide a dough which is non-sticky—i.e. a dough that is not so sticky that it causes handling and processing problems.

The present invention seeks to provide a solution to these problems.

SUMMARY ASPECTS OF THE PRESENT INVENTION

Aspects of the present invention are presented in the claims and in the following commentary.

In brief, some aspects of the present invention relate to:
1. An endogenous endo-β-1,4-xylanase inhibitor—including nucleotide sequences coding therefor and the amino acid sequences thereof, as well as variants, homologues, or fragments thereof.
2. Assay methods for determining the effect of the β-1,4-xylanase inhibitor on different xylanases.

3. Assay methods for determining the effect of different xylanases in dough.
4. Assay methods for determining the effect of glucanase(s) on different doughs containing xylanases.
5. Novel xylanases—including nucleotide sequences coding therefor and the amino acid sequences thereof, as well as variants, homologues, or fragments thereof.
6. Novel uses of xylanases.
7. Foodstuffs prepared with xylanases.

Other aspects concerning the amino acid sequence of the present invention and/or the nucleotide sequence of the present invention include: a construct comprising or capable of expressing the sequences of the present invention; a vector comprising or capable of expressing the sequences of the present invention; a plasmid comprising or capable of expressing the sequences of present invention; a tissue comprising or capable of expressing the sequences of the present invention; an organ comprising or capable of expressing the sequences of the present invention; a transformed host comprising or capable of expressing the sequences of the present invention; a transformed organism comprising or capable of expressing the sequences of the present invention. The present invention also encompasses methods of expressing the same, such as expression in a micro-organism; including methods for transferring same.

The present invention differs from the teachings of WO-A-98/49278 because inter alia that PCT patent application contains minimal sequence information regarding the proteinic inhibitor disclosed therein.

Aspects of the present invention are now discussed under appropriate section headings. For the sake of convenience, generally applicable teachings for the aspects of the present invention may be found in the sections titled "General Definitions" and "General Teachings". However, the teachings under each section are not necessarily limited to each particular section.

GENERAL DEFINITIONS

The term "wheat flour" as used herein is a synonym for the finely-ground meal of wheat. Preferably, however, the term means flour obtained from wheat per se and not from another grain. Thus, and unless otherwise expressed, references to "wheat flour" as used herein preferably mean references to wheat flour per se as well as to wheat flour when present in a medium, such as a dough.

The term "xylanase" is used in its normal sense—e.g. an enzyme that is inter alia capable of catalysing the depolymerisation of arabinoxylan which may be present in wheat (e.g. an enzyme that is inter alia capable of catalysing the solubilisation of WIP and catalysing the depolymerisation of WSP which may be present in wheat).

An assay for determining endo-$\beta$-1,4-xylanase activity is presented later. For convenience, this assay is called the "Xylanase Assay".

The term "nucleotide sequence" in relation to the present invention includes genomic DNA, cDNA, recombinant DNA (i.e. DNA prepared by use of recombinant DNA techniques), synthetic DNA, and RNA—as well as combinations thereof.

Preferably, the term "nucleotide sequence" means DNA.

The nucleotide sequences of the present invention may be single or double stranded.

The nucleotide sequences of the present invention may include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the nucleotide sequences described herein may be modified by any method available in the art. Such modifications may be carried out in to enhance the in vivo activity or life span of nucleotide sequences of the present invention.

The terms "variant" or "homologue" with respect to the nucleotide sequence of the present invention and the amino acid sequence of the present invention are synonymous with allelic variations of the sequences.

In particular, the term "homology" as used herein may be equated with the term "identity". Here, sequence homology with respect to the nucleotide sequence of the present invention and the amino acid sequence of the present invention can be determined by a simple "eyeball" comparison (i.e. a strict comparison) of any one or more of the sequences with another sequence to see if that other sequence has at least 75% identity to the sequence(s). Relative sequence homology (i.e. sequence identity) can also be determined by commercially available computer programs that can calculate % homology between two or more sequences. A typical example of such a computer program is CLUSTAL.

Hence, homology comparisons can be conducted by eye. However, more usually they are conducted with the aid of readily available sequence comparison programs. These commercially available computer programs can calculate % homology between two or more sequences.

% homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

Preferably, sequence comparisons are conducted using the simple BLAST search algorithm provided at www.ncbi.nlm.nih.gov/BLAST using the default parameters.

The present invention also encompasses nucleotide sequences that are complementary to the sequences presented herein, or any derivative, fragment or derivative thereof. If the sequence is complementary to a fragment thereof then that sequence can be used a probe to identify similar coding sequences in other organisms etc.

The present invention also encompasses nucleotide sequences that are capable of hybridising to the sequences presented herein, or any derivative, fragment or derivative thereof.

The present invention also encompasses nucleotide sequences that are capable of hybridising to the sequences that are complementary to the sequences presented herein, or any derivative, fragment or derivative thereof.

The term "complementary" also covers nucleotide sequences that can hybridise to the nucleotide sequences of the coding sequence.

The term "variant" also encompasses sequences that are complementary to sequences that are capable of hydridising to the nucleotide sequences presented herein.

Preferably, the term "variant" encompasses sequences that are complementary to sequences that are capable of hybridising under stringent conditions (e.g. 65° C. and 0.1×SSC {1×SSC=0.15 M NaCl, 0.015 Na$_3$ citrate pH 7.0}) to the nucleotide sequences presented herein.

The present invention also relates to nucleotide sequences that can hybridise to the nucleotide sequences of the present invention (including complementary sequences of those presented herein).

The present invention also relates to nucleotide sequences that are complementary to sequences that can hybridise to the nucleotide sequences of the present invention (including complementary sequences of those presented herein).

The term "hybridization" as used herein shall include "the process by which a strand of nucleic acid joins with a complementary strand through base pairing" (Coombs J (1994) Dictionary of Biotechnology, Stockton Press, New York N.Y.) as well as the process of amplification as carried out in polymerase chain reaction technologies as described in Dieffenbach C W and G S Dveksler (1995, PCR Primer, a Laboratory Manual, Cold Spring Harbor Press, Plainview N.Y.).

Also included within the scope of the present invention are polynucleotide sequences that are capable of hybridizing to the nucleotide sequences presented herein under conditions of intermediate to maximal stringency. Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences.

In a preferred aspect, the present invention covers nucleotide sequences that can hybridise to the nucleotide sequence of the present invention under stringent conditions (e.g. 65° C. and 0.1×SSC).

Endogenous Endo-β-1,4-Xylanase Inhibitor

In one aspect the present invention provides an endogenous endo-β-1,4-xylanase inhibitor that is obtainable from wheat flour.

In our studies, we have found that the inhibitor is a dipeptide, having a MW of about 40 kDa (as measured by SDS or MS) and that it has a pl of about 8 to about 9.5.

In one aspect of the present invention, the inhibitor is in an isolated form and/or in a substantially pure form. Here, the term "isolated" means that the inhibitor is not in its natural environment.

Sequence analysis to date has revealed the that the inhibitor has at least one or more of the sequences presented as SEQ ID No. 13, SEQ ID No. 14, SEQ ID No 15, SEQ ID No. 16, SEQ ID No. 17, SEQ ID No. 18 and/or SEQ ID No. 19.

Thus, the present invention encompasses an endo-β-1,4-xylanase inhibitor which comprises has at least one or more of the sequences presented as SEQ ID No. 13, SEQ ID No. 14, SEQ ID No 15, SEQ ID No. 16, SEQ ID No. 17, SEQ ID No. 18 and/or SEQ ID No. 19 or a variant, homologue, or fragment thereof.

The terms "variant", "homologue" or "fragment" in relation to the inhibitor of the present invention include any substitution of, variation of, modification of, replacement of, deletion of or addition of one (or more) amino acid from or to the sequence providing the resultant amino acid sequence has xylanase inhibitory action, preferably having at least the same activity as an inhibitor that has at least one or more of the sequences presented as SEQ ID No. 13, SEQ ID No. 14, SEQ ID No 15, SEQ ID No. 16, SEQ ID No. 17, SEQ ID No. 18 and/or SEQ ID No. 19. In particular, the term "homologue" covers homology with respect to structure and/or function providing the resultant inhibitor has xylanase inhibitory action, preferably having at least the same activity of an inhibitor that has at least one or more of the sequences presented as SEQ ID No. 13, SEQ ID No. 14, SEQ ID No 15, SEQ ID No. 16, SEQ ID No. 17, SEQ ID No. 18 and/or SEQ ID No. 19. With respect to sequence homology (i.e. sequence similarity or sequence identity), preferably there is at least 75%, more preferably at least 80%, more preferably at least 85%, more preferably at least 90% homology to the sequence shown in the attached sequence listings. More preferably there is at least 95%, more preferably at least 98%, homology to the sequence shown in the attached sequence listings.

A putative example of a variant of the inhibitor of the present has at least one or more of the sequences presented as SEQ. ID No. 1 and SEQ. ID No. 2.

The inhibitor aspect of the present invention is advantageous for a number of reasons.

By way of example, by now knowing the chemical identity of an endogenous endo-β-1,4-xylanase inhibitor workers can now determine the quantity of the inhibitor in, for example, a wheat flour. For convenience, we shall call this method the "Inhibitor Amount Determination Method".

The Inhibitor Amount Determination Method would enable workers to select one or more appropriate xylanases for addition to the wheat flour and/or select appropriate amounts of one or more xylanases for addition to the wheat flour.

Thus, the present invention provides a method comprising: (a) determining the amount or type of inhibitor in a wheat flour, (b) selecting a suitable xylanase for addition to the wheat flour and/or selecting a suitable amount of a xylanase for addition to the wheat flour; and (c) adding the suitable xylanase and/or suitable amount of the xylanase to the wheat flour.

The present invention also provides a method comprising: (a) determining the amount or type of inhibitor in a wheat flour; (b) selecting a suitable xylanase inhibitor for addition to the wheat flour and/or selecting a suitable amount of a xylanase inhibitor for addition to the wheat flour, and (c) adding the suitable xylanase inhibitor and/or suitable amount of the xylanase inhibitor to the wheat flour.

The present invention also provides a method comprising: (a) determining the amount or type of inhibitor in a wheat flour; (b) selecting a suitable xylanase and a suitable xylanase inhibitor for addition to the wheat flour and/or selecting a suitable amount of a xylanase inhibitor for addition to the wheat flour; and (c) adding the suitable xylanase and the suitable xylanase inhibitor and/or suitable amount of the xylanase inhibitor to the wheat flour.

Detection of the amount of inhibitor can be determined by standard chemical techniques, such as by analysis of solid state NMR spectra. The amount of inhibitor may even be determined by use of xylanase enzymes that are known to be detrimentally affected by the inhibitor. In this last aspect, it would be possible to take a sample of the wheat flour and add it to a known quantity of such a xylanase. At a certain time point the activity of the xylanase can be determined, which resultant activity can then be correlated to an amount of inhibitor in the wheat flour.

Thus, the present invention also encompasses the use of the combination of a xylanase and the inhibitor as a means to calibrating and/or determining the quantity of inhibitor in a wheat flour sample.

Antibodies to the inhibitor can be used to screen wheat flour samples for the presence of the inhibitor of the present invention. The antibodies may even be used to isolate amounts of the inhibitor from a wheat flour sample.

Assay Methods for Determining the Effect of the β-1,4-Xylanase Inhibitor on Different Xylanases There is an additional important use of the inhibitor of the present invention.

In this respect, the inhibitor could be used in an assay/screen to identify xylanases that are affected by the inhibitor.

By way of example, in some circumstances, it may be desirable to screen for a xylanase that has a low resistance— i.e. are not that resistant—to the inhibitor.

In one aspect, the inhibitor can be used in an assay/screen to identify xylanases that have a fair (medium) resistance— i.e. are reasonably resistant—to the inhibitor.

In one aspect, the inhibitor can be used in an assay/screen to identify xylanases that have a high resistance to the inhibitor.

A suitable Protocol for determining the degree of inhibition by the inhibitor is presented later on. For convenience, we shall call this Protocol "Inhibitor Assay Protocol".

Thus, the present invention provides a method for determining the degree of resistance of a xylanase to a xylanase inhibitor, wherein the method comprises: (a) contacting a xylanase of interest with the inhibitor; and (b) determining whether the inhibitor inhibits the activity of the xylanase of interest. For convenience, we shall call this method the "Inhibitor Assay Method".

Here, the term "resistant" means that the activity of the xylanase is not totally inhibited by the inhibitor. In other words, the inhibitor can be used in an assay/screen to identify xylanases that are not detrimentally affected by the inhibitor.

Thus, the term "degree of resistance" in relation to the xylanase vis-a-vis the xylanase inhibitor is synonymous with the degree of non-inhibition of the activity of a xylanase by the xylanase inhibitor. Thus, a xylanase that has a high degree of resistance to the xylanase inhibitor is akin to a high degree of non-inhibition of a xylanase by the xylanase inhibitor.

The present invention also encompasses a process comprising the steps of (a) performing the Inhibitor Assay Method; (b) identifying one or more xylanases having a high (or medium or low) degree of resistance to the inhibitor; (c) preparing a quantity of those one or more identified xylanases.

Suitable identified xylanases can then be used to prepare a foodstuff, in particular a dough to make a bakery product.

In addition, by identifying a xylanase that is resistant to some extent to the inhibitor (i.e. a xylanase that is not inhibited as much as other xylanases), it is possible to add less of that identified xylanase to a medium for subsequent utilisation thereof. End uses for the xylanases can include any one or more of the preparation of foodstuffs, protein and starch production, paper production and pulp processing etc.

Thus, the present invention also encompasses a process comprising the steps of: (a) performing the Inhibitor Assay Method; (b) identifying one or more xylanases having a high (or medium or low) degree of resistance to the inhibitor; and (c) preparing a dough comprising the one or more identified xylanases.

In the course of the experiments relating to the present invention, we surprisingly found that bacterial xylanases were able to be resistant to the inhibitor, in the sense that their activity was not completely abolished. In some cases, the xylanases exhibited very favourable resistance to the inhibitor.

Assay Methods for Determining the Effect of Different Xylanases in Doughs

When some bacterial xylanases that had been identified as being suitable by the Inhibitor Assay Method were present in a dough mixture, we surprisingly found that the dough mixture was not as sticky as a dough mixture comprising a fungal xylanase. These results were completely unexpected in view of the teachings of the prior art.

Thus, the present invention provides a further assay method for identifying a bacterial xylanase or mutant thereof suitable for use in the preparation of a baked foodstuff. The method comprises (a) incorporating a bacterial xylanase of interest in a dough mixture; and (b) determining the stickiness of the resultant dough mixture; such that the bacterial xylanase or mutant thereof is suitable for use in the preparation of a baked foodstuff if the resultant dough mixture has a stickiness that is less than a similar dough mixture comprising a fungal xylanase. For convenience, we shall call this method the "Stickiness Assay Method".

Thus, the present invention also provides a process comprising the steps of: (a) performing the Stickiness Assay Method; (b) identifying one or more xylanases suitable for use in the preparation of a baked foodstuff; (c) preparing a quantity of those one or more identified xylanases.

A suitable Protocol for determining the stickiness of a dough is presented later on. For convenience, we shall call this Protocol the "Stickiness Protocol". In accordance with the present invention a dough comprising a xylanase according to the present invention that is less sticky than a dough comprising a fungal xylanase may be called, on occasion, a "non-sticky dough".

If a bacterial xylanase shows favourable properties—in that it does not produce a dough that is as sticky as a dough comprising a fungal xylanase—then that xylanase may be used to prepare a foodstuff, such as a dough for preparing a bakery product.

Thus, the present invention also provides a process comprising the steps of: (a) performing the Stickiness Assay Method; (b) identifying one or more xylanases suitable for use in the preparation of a baked foodstuff; and (c) preparing a dough comprising the one or more identified xylanases.

Assay Methods for Determining the Effect of Glucanase(s) on Dough Properties for Doughs that May Comprise Xylanases In the course of the experiments relating to the present invention, we also found that the presence of glucanase enzymes in certain amounts could have a detrimental effect on the xylanases.

Thus, in one aspect, it is advantageous not to have detrimental levels of glucanase enzymes in the xylanase preparation—such as the medium used to prepare or extract the xylanase enzymes. In addition, for some aspects, it is advantageous not to have detrimental levels of glucanase enzymes in a medium that is to be used to prepare a foodstuff which medium will contain the xylanase. Here, the term "detrimental level" means an amount of glucanase is present such that the benefits from the xylanase are masked by the adverse effect of the glucanase enzymes.

Thus, the present invention provides a further assay method for identifying a xylanase composition (such as a xylanase preparation) or a medium in which a xylanase is to be prepared or a medium to which a xylanase is to be added that is to be suitable for use in the preparation of a baked foodstuff, the method comprising (a) providing a composition containing the xylanase of interest or a medium in which the xylanase is to be prepared or a medium to which the xylanase is to be added; and (b) determining the presence of active glucanase enzyme(s) in the composition or medium; such that if there is at most a low level of active glucanase enzyme(s) in the composition or medium then that composition or medium is suitable for the preparation of a baked foodstuff. For convenience, we shall call this method the "Glucanase Assay Method".

The present invention also provides a process comprising the steps of: (a) performing the Glucanase Assay Method; (b) identifying one or more compositions or mediums suitable for use in the preparation of a baked foodstuff; (c) preparing a quantity of those one or more identified compositions or mediums.

A suitable Protocol for determining the activity of glucanases is presented later on. For convenience, we shall call this Protocol the "Glucanase Protocol".

If the composition or medium shows favourable properties—in the sense that the beneficial effects associated with the xylanase are not completely masked by the presence of detrimental amounts of glucanase enzymes—then that composition or medium may be used to prepare a foodstuff, preferably dough that is used to make a bakery product.

Thus, the present invention also encompasses a process comprising the steps of: (a) performing the Glucanase Assay Method; (b) identifying one or more identified compositions or mediums suitable for use in the preparation of a baked foodstuff; and (c) preparing a dough comprising the one or more identified compositions or mediums.

Thus, the present invention covers a xylanase preparation, wherein the xylanase preparation is substantially free of glucanase enzyme(s).

In this respect, the xylanase preparation can be prepared from an initial preparation from which at least substantially all of the glucanase enzyme(s) that may be present is(are) removed or even wherein the activity of the glucanase enzyme(s) is suppressed or eliminated. Techniques for achieving this could include using antibodies that recognise and bind to the glucanase enzyme(s) and in doing so inactivate the activity of the glucanase enzyme(s). Alternatively, glucanase enzyme(s) specific antibodies could be bound to a support such that passage of the initial preparation past the bound antibodies would result in the glucanase enzyme(s) being removed from it thereby forming a xylanase preparation being substantially free of glucanase enzyme(s). In an alternative embodiment, or even in an additional embodiment, the xylanase preparation can be prepared from a host organism that has minimal or no glucanase enzyme activity. In this aspect, the activity of the glucanase enzymes that are present in the host organism may be inactivated. In an alternative aspect, the expression of the glucanase genes can be silenced and/or knocked-out. Techniques for achieving this could include using antisense sequences to the glucanase coding sequences. In a further embodiment, a host organism is used that has no or at most minimal expression of glucanase enzymes.

$K_i$ Assay

In some cases, measurement of the $K_i$ value of a xylanase (which we call here a "$K_i$ assay") may be useful. In this respect, we have found that in some cases the $K_i$ value is sometimes indicative of the suitability of the xylanase for certain application(s). Knowledge of the $K_i$ value could be useful on its own.

Combination Assays

The present invention also encompasses suitable combinations of the assays of the present invention.

In this respect, the present invention includes a combination method comprising two or more of the following steps: a step comprising the Inhibitor Amount Determination Method, a step comprising the Inhibitor Assay Method, a step comprising the Stickiness Assay Method; a step comprising the Glucanase Assay Method; and a step comprising the $K_i$ assay. In the combination method, the steps can occur in any order and need not necessarily occur simulataneously or consecutively.

Novel Xylanases

As indicated above, the present invention provides a suitable assay for identifying xylanases that can be used in the preparation of foodstuffs, in particular doughs for use in the preparation of bakery products.

In this respect, we have identified three new xylanases that are suitable for the preparation of foodstuffs, in particular doughs for use in the preparation of bakery products.

Thus, the present invention also includes an amino acid sequence comprising any one of the amino acid sequences presented as SEQ ID No. 7, SEQ ID No. 9 or SEQ ID No. 11, or a variant, homologue or fragment thereof.

The terms "variant", "homologue" or "fragment" in relation to the xylanase of the present invention include any substitution of, variation of, modification of, replacement of, deletion of or addition of one (or more) amino acid from or to the sequence providing the resultant amino acid sequence has xylanase activity, preferably having at least the same activity comprising any one of the amino acid sequences presented as SEQ ID No. 7, SEQ ID No. 9 or SEQ ID No. 11. In particular, the term "homologue" covers homology with respect to structure and/or function providing the resultant protein has xylanase activity, preferably at least the same activity of any one of the amino acid sequences presented as SEQ ID No. 7, SEQ ID No. 9 or SEQ ID No. 11. With respect to sequence homology (i.e. sequence similarity or sequence identity), preferably there is at least 75%, more preferably at least 85%, more preferably at least 90% homology to the sequence shown in the attached sequence listings. More preferably there is at least 95%, more preferably at least 98%, homology to the sequence shown in the attached sequence listings.

Preferably, the xylanase comprises the sequence presented as SEQ ID No. 7 or SEQ ID No. 11, or a variant, homologue or fragment thereof.

The present invention also encompasses a nucleotide sequence encoding the amino acid sequence of the present invention.

Preferably, the nucleotide sequence of the present invention is selected from:
(a) a nucleotide sequence comprising any one of the nucleotide sequences presented as SEQ ID No. 8, SEQ ID No. 10 or SEQ ID No. 12, or a variant, homologue or fragment thereof;
(b) any one of the nucleotide sequences presented as SEQ ID No. 8, SEQ ID No. 10 or SEQ ID No. 12, or the complement thereof;
(c) a nucleotide sequence capable of hybridising any one of the nucleotide sequences presented as SEQ ID No. 8, SEQ ID No. 10 or SEQ ID No. 12, or a fragment thereof;
(d) a nucleotide sequence capable of hybridising to the complement any one of the nucleotide sequences presented as SEQ ID No. 8, SEQ ID No. 10 or SEQ ID No. 12, or a fragment thereof; and
(e) a nucleotide sequence which is degenerate as a result of the genetic code to the nucleotides defined in (a), (b), (c) or (d).

The terms "variant", "homologue" or "fragment" in relation to the nucleotide sequence of the present invention include any substitution of, variation of, modification of, replacement of, deletion of or addition of one (or more) nucleic acid from or to the sequence providing the resultant nucleotide sequence codes for an amino acid sequence has xylanase activity, preferably having at least the same activity comprising any one of the amino acid sequences presented as SEQ ID No. 7, SEQ ID No. 9 or SEQ ID No. 11. In particular, the term "homologue" covers homology with respect to structure and/or function providing the resultant expressed protein has xylanase activity, preferably at least the same activity of any one of the amino acid sequences presented as SEQ ID No. 7, SEQ ID No. 9 or SEQ ID No. 11. With respect to sequence homology (i.e. sequence similarity or sequence identity), preferably there is at least 75%, more preferably at least 85%, more preferably at least 90% homology to the sequence shown as SEQ ID No. 8, SEQ ID No. 10 or SEQ ID No. 12 in the attached sequence listings. More preferably there is at least 95%, more preferably at least 98%, homology to the sequence shown in the attached sequence listings.

Preferably, the nucleotide sequence of the present invention comprises the sequence presented as SEQ ID No. 8 or SEQ ID No. 12, or a variant, homologue or fragment thereof.

Novel Uses of Xylanases

As indicated above, the present invention also provides a suitable assay for identifying xylanases that can be used in the preparation of non-sticky doughs (as defined herein) for use in the preparation of bakery products.

In this respect, we have identified certain xylanases, both known and new bacterial xylanases, that are suitable for the preparation of foodstuffs, in particular doughs for use in the preparation of bakery products.

Thus, the present invention covers a non-sticky dough (as herein defined) which dough comprises a xylanase identifiable by the assay of the present invention. Preferably, the xylanase has an amino acid sequence presented as any one of SEQ ID No.s 3, 5, 7, 9, 11, or a variant, derivative or homologue thereof. More preferably, the xylanase has an amino acid sequence presented as any one of SEQ ID No.s 5, 7, 9, 11, or a variant, derivative or homologue thereof.

In contrast to the prior art systems, the present invention provides for the possibility of the addition of xylanase directly to flour prior to production of the dough. Thus, a single batch a flour/xylanase mixture may be delivered to the dough producer. Moreover, the dough producer does not require dosing equipment to be able to obtain a readily handable dough.

Foodstuffs Prepared with Xylanases

The present invention provides a means of identifying suitable xylanases for use in the manufacture of a foodstuff. Typical foodstuffs, which also include animal feed, include dairy products, meat products, poultry products, fish products and bakery products.

Preferably, the foodstuff is a bakery product. Typical bakery (baked) products incorporated within the scope of the present invention include bread—such as loaves, rolls, buns, pizza bases etc.—pretzels, tortillas, cakes, cookies, biscuits, crackers etc.

General Teachings

In the following commentary references to "nucleotide sequence of the present invention" and "amino acid sequence of the present invention" refer respectively to any one or more of the nucleotide sequences presented herein and to any one or more of the amino acid sequences present herein.

Amino Acid Sequence/Polypeptide Sequence

The term "amino acid sequence of the present invention" is synonymous with the phrase "polypeptide sequence of the present invention". Here, the amino acid sequence may be that for the xylanase or the xylanase inhibitor.

Polypeptides of the present invention also include fragments of the presented amino acid sequence and variants thereof. Suitable fragments will be at least 5, e.g. at least 10, 12, 15 or 20 amino acids in size.

Polypeptides of the present invention may also be modified to contain one or more (e.g. at least 2, 3, 5, or 10) substitutions, deletions or insertions, including conserved substitutions.

Conserved substitutions may be made according to the following table which indicates conservative substitutions, where amino acids on the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |
| OTHER | | N Q D E |

Polypeptides of the present invention may be in a substantially isolated form. It will be understood that the polypeptide may be mixed with carriers or diluents which will not interfere with the intended purpose of the polypeptide and still be regarded as substantially isolated. A polypeptide of the present invention may also be in a substantially purified form, in which case it will generally comprise the polypeptide in a preparation in which more than 90%, e.g. 95%, 98% or 99% of the polypeptide in the preparation is a polypeptide of the present invention. Polypeptides of the present invention may be modified for example by the addition of histidine residues to assist their purification or by the addition of a signal sequence to promote their secretion from a cell as discussed below.

Polypeptides of the present invention may be produced by synthetic means (e.g. as described by Geysen et al., 1996) or recombinantly, as described below.

The use of suitable host cells—such as yeast, fungal and plant host cells—may provide for such post-translational modifications (e.g. myristolation, glycosylation, truncation, lapidation and tyrosine, serine or threonine phosphorylation) as may be needed to confer optimal biological activity on recombinant expression products of the present invention.

Nucleotide Sequence/Polynucleotide Sequence

The term "nucleotide sequence of the present invention" is synonymous with the phrase "polynucleotide sequence of the present invention".

Polynucleotides of the present invention include nucleotide acid sequences encoding the polypeptides of the present invention. It will appreciated that a range of different polynucleotides encode a given amino acid sequence as a consequence of the degeneracy of the genetic code.

By knowledge of the amino acid sequences set out herein it is possible to devise partial and full-length nucleic acid sequences such as cDNA and/or genomic clones that encode the polypeptides of the present invention. For example, polynucleotides of the present invention may be obtained using degenerate PCR which will use primers designed to target sequences encoding the amino acid sequences presented herein. The primers will typically contain multiple degenerate positions. However, to minimise degeneracy, sequences will be chosen that encode regions of the amino acid sequences presented herein containing amino acids such as methionine which are coded for by only one triplet. In addition, sequences will be chosen to take into account codon usage in the organism whose nucleic acid is used as the template DNA for the PCR procedure. PCR will be used at stringency conditions lower than those used for cloning sequences with single sequence (non-denegerate) primers against known sequences.

Nucleic acid sequences obtained by PCR that encode polypeptide fragments of the present invention may then be used to obtain larger sequences using hybridization library screening techniques. For example a PCR clone may be labelled with radioactive atoms and used to screen a cDNA or genomic library from other species, preferably other plant species or fungal species. Hybridization conditions will typically be conditions of medium to high stringency (for example 0.03M sodium chloride and 0.03M sodium citrate at from about 50° C. to about 60° C.).

Degenerate nucleic acid probes encoding all or part of the amino acid sequence may also be used to probe cDNA and/or genomic libraries from other species, preferably other plant species or fungal species. However, it is preferred to carry out PCR techniques initially to obtain a single sequence for use in further screening procedures.

Polynucleotide sequences of the present invention obtained using the techniques described above may be used to obtain further homologous sequences and variants using the techniques described above. They may also be modified for use in expressing the polypeptides of the present invention in a variety of host cells systems, for example to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

Polynucleotides of the present invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the present invention as used herein.

Polynucleotides or primers of the present invention may carry a revealing label. Suitable labels include radioisotopes such as $^{32}P$ or $^{35}S$, enzyme labels, or other protein labels such as biotin. Such labels may be added to polynucleotides or primers of the present invention and may be detected using by techniques known per se.

Polynucleotides such as a DNA polynucleotide and primers according to the present invention may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15-30 nucleotides) to a region of the endo-β-1,4-xylanase inhibitor gene which it is desired to clone, bringing the primers into contact with mRNA or cDNA obtained from a fungal, plant or prokaryotic cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Regulatory Sequences

Preferably, the polynucleotide of the present invention is operably linked to a regulatory sequence which is capable of providing for the expression of the coding sequence, such as by the chosen host cell. By way of example, the present invention covers a vector comprising the polynucleotide of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals.

The term "promoter" is used in the normal sense of the art, e.g. an RNA polymerase binding site.

Enhanced expression of the polynucleotide encoding the polypeptide of the present invention may also be achieved by the selection of heterologous regulatory regions, e.g. promoter, secretion leader and terminator regions, which serve to increase expression and, if desired, secretion levels of the protein of interest from the chosen expression host and/or to provide for the inducible control of the expression of the polypeptide of the present invention Preferably, the nucleotide sequence of the present invention may be operably linked to at least a promoter.

Aside from the promoter native to the gene encoding the polypeptide of the present invention, other promoters may be used to direct expression of the polypeptide of the present invention. The promoter may be selected for its efficiency in directing the expression of the polypeptide of the present invention in the desired expression host.

In another embodiment, a constitutive promoter may be selected to direct the expression of the desired polypeptide of the present invention. Such an expression construct may provide additional advantages since it circumvents the need to culture the expression hosts on a medium containing an inducing substrate.

Examples of strong constitutive and/or inducible promoters which are preferred for use in fungal expression hosts are those which are obtainable from the fungal genes for xylanase (xlnA), phytase, ATP-synthetase, subunit 9 (oliC), triose phosphate isomerase (tpi), alcohol dehydrogenase (AdhA), α-amylase (amy), amyloglucosidase (AG—from the glaA gene), acetamidase (amdS) and glyceraldehyde-3-phosphate dehydrogenase (gpd) promoters.

Examples of strong yeast promoters are those obtainable from the genes for alcohol dehydrogenase, lactase, 3-phosphoglycerate kinase and triosephosphate isomerase.

Examples of strong bacterial promoters are the α-amylase and SP02 promoters as well as promoters from extracellular protease genes.

Hybrid promoters may also be used to improve inducible regulation of the expression construct.

The promoter can additionally include features to ensure or to increase expression in a suitable host. For example, the features can be conserved regions such as a Pribnow Box or a TATA box. The promoter may even contain other sequences to affect (such as to maintain, enhance, decrease) the levels of expression of the nucleotide sequence of the present invention. For example, suitable other sequences include the Sh1-intron or an ADH intron. Other sequences include inducible elements—such as temperature, chemical, light or stress inducible elements. Also, suitable elements to enhance transcription or translation may be present. An example of the latter element is the TMV 5' signal sequence (see Sleat Gene 217 [1987] 217-225; and Dawson Plant Mol. Biol. 23 [1993] 97).

Secretion

Often, it is desirable for the polypeptide of the present invention to be secreted from the expression host into the culture medium from where the polypeptide of the present invention may be more easily recovered. According to the present invention, the secretion leader sequence may be selected on the basis of the desired expression host. Hybrid signal sequences may also be used with the context of the present invention.

Typical examples of heterologous secretion leader sequences are those originating from the fungal amyloglucosidase (AG) gene (glaA—both 18 and 24 amino acid versions e.g. from *Aspergillus*), the a-factor gene (yeasts e.g. *Saccharomyces* and *Kluyveromyces*) or the α-amylase gene (*Bacillus*).

Constructs

The term "construct"—which is synonymous with terms such as "conjugate", "cassette" and "hybrid"—includes the nucleotide sequence according to the present invention directly or indirectly attached to a promoter. An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In each case, the terms do not cover the natural combination of the nucleotide sequence coding for the protein ordinarily associated with the wild type gene promoter and when they are both in their natural environment.

The construct may even contain or express a marker which allows for the selection of the genetic construct in, for example, a bacterium, preferably of the genus *Bacillus*, such as *Bacillus subtilis*, or plants, such as potatoes, sugar beet etc., into which it has been transferred. Various markers exist which may be used, such as for example those encoding mannose-6-phosphate isomerase (especially for plants) or those markers that provide for antibiotic resistance—e.g. resistance to G418, hygromycin, bleomycin, kanamycin and gentamycin.

Preferably the construct of the present invention comprises at least the nucleotide sequence of the present invention operably linked to a promoter.

Vectors

The term "vector" includes expression vectors and transformation vectors and shuttle vectors.

The term "expression vector" means a construct capable of in vivo or in vitro expression.

The term "transformation vector" means a construct capable of being transferred from one entity to another entity—which may be of the species or may be of a different species. If the construct is capable of being transferred from one species to another—such as from an *E. coli* plasmid to a bacterium, preferably of the genus *Bacillus*, then the transformation vector is sometimes called a "shuttle vector". It may even be a construct capable of being transferred from an *E. coli* plasmid to an *Agrobacterium* to a plant.

The vectors of the present invention may be transformed into a suitable host cell as described below to provide for expression of a polypeptide of the present invention. Thus, in a further aspect the invention provides a process for preparing polypeptides according to the present invention which comprises cultivating a host cell transformed or transfected with an expression vector as described above under conditions to provide for expression by the vector of a coding sequence encoding the polypeptides, and recovering the expressed polypeptides.

The vectors may be for example, plasmid, virus or phage vectors provided with an origin of replication, optionally a promoter for the expression of the said polynucleotide and optionally a regulator of the promoter.

The vectors of the present invention may contain one or more selectable marker genes. The most suitable selection systems for industrial micro-organisms are those formed by the group of selection markers which do not require a mutation in the host organism. Examples of fungal selection markers are the genes for acetamidase (amdS), ATP synthetase, subunit 9 (oliC), orotidine-5'-phosphate-decarboxylase (pvrA), phleomycin and benomyl resistance (benA). Examples of non-fungal selection markers are the bacterial G418 resistance gene (this may also be used in yeast, but not in fungi), the ampicillin resistance gene (*E. coli*), the neomycin resistance gene (*Bacillus*) and the *E. coli* uidA gene, coding for β-glucuronidase (GUS).

Vectors may be used in vitro, for example for the production of RNA or used to transfect or transform a host cell.

Thus, polynucleotides of the present invention can be incorporated into a recombinant vector (typically a replicable vector), for example a cloning or expression vector. The vector may be used to replicate the nucleic acid in a compatible host cell. Thus in a further embodiment, the invention provides a method of making polynucleotides of the present invention by introducing a polynucleotide of the present invention into a replicable vector, introducing the vector into a compatible host cell, and growing the host cell under conditions which bring about replication of the vector. The vector may be recovered from the host cell. Suitable host cells are described below in connection with expression vectors.

Tissue

The term "tissue" as used herein includes tissue per se and organ.

Host Cells

The term "host cell"—in relation to the present invention includes any cell that could comprise the nucleotide sequence coding for the recombinant protein according to the present invention and/or products obtained therefrom, wherein a promoter can allow expression of the nucleotide sequence according to the present invention when present in the host cell.

Thus, a further embodiment of the present invention provides host cells transformed or transfected with a polynucleotide of the present invention. Preferably said polynucleotide is carried in a vector for the replication and expression of said polynucleotides. The cells will be chosen to be compatible with the said vector and may for example be prokaryotic (for example bacterial), fungal, yeast or plant cells.

The gram-negative bacterium *E. coli* is widely used as a host for heterologous gene expression. However, large amounts of heterologous protein tend to accumulate inside the cell. Subsequent purification of the desired protein from the bulk of *E. coli* intracellular proteins can sometimes be difficult.

In contrast to *E. coli*, bacteria from the genus *Bacillus* are very suitable as heterologous hosts because of their capability to secrete proteins into the culture medium. Other bacteria suitable as hosts are those from the genera *Streptomyces* and *Pseudomonas*.

Depending on the nature of the polynucleotide encoding the polypeptide of the present invention, and/or the desirability for further processing of the expressed protein, eukaryotic hosts such as yeasts or fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a fungal host organism should be selected.

Examples of preferred expression hosts within the scope of the present invention are fungi such as *Aspergillus* species (such as those described in EP-A-0184438 and EP-A-0284603) and *Trichoderma* species; bacteria such as *Bacillus* species (such as those described in EP-A-0134048 and EP-A-0253455), *Streptomyces* species and *Pseudomonas* species; and yeasts such as *Kluyveromyces* species (such as those described in EP-A-0096430 and EP-A-0301670) and *Saccharomyces* species.

Typical expression hosts may be selected from *Aspergillus niger, Aspergillus niger* var. *tubigenis, Aspergillus niger* var. *awamori, Aspergillus aculeatis, Aspergillus nidulans, Aspergillus oryzae, Trichoderma reesei, Bacillus subtilis, Bacillus licheniformis, Bacillus amyloliquefaciens, Kluyveromyces lactis* and *Saccharomyces cerevisiae*.

Organism

The term "organism" in relation to the present invention includes any organism that could comprise the nucleotide sequence coding for the recombinant protein according to the present invention and/or products obtained therefrom, wherein a promoter can allow expression of the nucleotide sequence according to the present invention when present in the organism. For the xylanase inhibitor aspect of the present invention, preferable organisms may include a fungus, yeast or a plant. For the xylanase aspect of the present invention, a preferable organism may be a bacterium, preferably of the genus *Bacillus*, more preferably *Bacillus subtilis*.

The term "transgenic organism" in relation to the present invention includes any organism that comprises the nucleotide sequence coding for the protein according to the present invention and/or products obtained therefrom, wherein the promoter can allow expression of the nucleotide sequence according to the present invention within the organism. Preferably the nucleotide sequence is incorporated in the genome of the organism.

The term "transgenic organism" does not cover the native nucleotide coding sequence according to the present invention in its natural environment when it is under the control of its native promoter which is also in its natural environment. In addition, the present invention does not cover the native protein according to the present invention when it is in its natural environment and when it has been expressed by its native nucleotide coding sequence which is also in its natural environment and when that nucleotide sequence is under the control of its native promoter which is also in its natural environment.

Therefore, the transgenic organism of the present invention includes an organism comprising any one of, or combinations of, the nucleotide sequence coding for the amino acid sequence according to the present invention, constructs according to the present invention (including combinations thereof), vectors according to the present invention, plasmids according to the present invention, cells according to the present invention, tissues according to the present invention or the products thereof. The transformed cell or organism could prepare acceptable quantities of the desired compound which would be easily retrievable from, the cell or organism.

Transformation of Host Cells/Host Organisms

As indicated earlier, the host organism can be a prokaryotic or a eukaryotic organism. Examples of suitable prokaryotic hosts include *E. coli* and *Bacillus subtilis*. Teachings on the transformation of prokaryotic hosts is well documented in the art, for example see Sambrook et al (Molecular Cloning: A Laboratory Manual, 2nd edition, 1989, Cold Spring Harbor Laboratory Press) and Ausubel et al., Current Protocols in Molecular Biology (1995), John Wiley & Sons, Inc.

If a prokaryotic host is used then the nucleotide sequence may need to be suitably modified before transformation—such as by removal of introns.

As mentioned above, a preferred host organism is of the genus *Bacillus*, such as *Bacillus subtilis*.

In another embodiment the transgenic organism can be a yeast. In this regard, yeast have also been widely used as a vehicle for heterologous gene expression. The species *Saccharomyces cerevisiae* has a long history of industrial use, including its use for heterologous gene expression. Expression of heterologous genes in *Saccharomyces cerevisiae* has been reviewed by Goodey et al (1987, Yeast Biotechnology, D R Berry et al, eds, pp 401-429, Allen and Unwin, London) and by King et al (1989, Molecular and Cell Biology of Yeasts, E F Walton and G T Yarronton, eds, pp 107-133, Blackie, Glasgow).

For several reasons *Saccharomyces cerevisiae* is well suited for heterologous gene expression. First, it is non-pathogenic to humans and it is incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of *Saccharomyces cerevisiae*.

A review of the principles of heterologous gene expression in *Saccharomyces cerevisiae* and secretion of gene products is given by E Hinchcliffe E Kenny (1993, "Yeast as a vehicle for the expression of heterologous genes", Yeasts, Vol 5, Anthony H Rose and J Stuart Harrison, eds, 2nd edition, Academic Press Ltd.).

Several types of yeast vectors are available, including integrative vectors, which require recombination with the host genome for their maintenance, and autonomously replicating plasmid vectors.

In order to prepare the transgenic *Saccharomyces*, expression constructs are prepared by inserting the nucleotide sequence of the present invention into a construct designed for expression in yeast. Several types of constructs used for heterologous expression have been developed. The constructs contain a promoter active in yeast fused to the nucleotide sequence of the present invention, usually a promoter of yeast origin, such as the GAL1 promoter, is used. Usually a signal sequence of yeast origin, such as the sequence encoding the SUC2 signal peptide, is used. A terminator active in yeast ends the expression system.

For the transformation of yeast several transformation protocols have been developed. For example, a transgenic *Saccharomyces* according to the present invention can be prepared by following the teachings of Hinnen et al (1978, Proceedings of the National Academy of Sciences of the USA 75, 1929); Beggs, J D (1978, Nature, London, 275, 104); and Ito, H et al (1983, J Bacteriology 153, 163-168).

The transformed yeast cells are selected using various selective markers. Among the markers used for transformation are a number of auxotrophic markers such as LEU2, HIS4 and TRP1, and dominant antibiotic resistance markers such as aminoglycoside antibiotic markers, eg G418.

Another host organism is a plant. The basic principle in the construction of genetically modified plants is to insert genetic information in the plant genome so as to obtain a stable maintenance of the inserted genetic material.

Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205-225) and Christou (Agro-Food-Industry Hi-Tech March/April 1994 17-27).

Thus, in one aspect, the present invention relates to a vector system which carries a nucleotide sequence or construct according to the present invention and which is capable of introducing the nucleotide sequence or construct into the genome of an organism, such as a plant.

The vector system may comprise one vector, but it can comprise two vectors. In the case of two vectors, the vector system is normally referred to as a binary vector system. Binary vector systems are described in further detail in Gynheung An et al. (1980), Binary Vectors, Plant Molecular Biology Manual A3, 1-19.

One extensively employed system for transformation of plant cells with a given nucleotide sequence is based on the use of a Ti plasmid from *Agrobacterium tumefaciens* or a Ri plasmid from *Agrobacterium rhizogenes* An et al. (1986), Plant Physiol. 81, 301-305 and Butcher D. N. et al. (1980), Tissue Culture Methods for Plant Pathologists, eds.: D. S. Ingrams and J. P. Helgeson, 203-208.

Several different Ti and Ri plasmids have been constructed which are suitable for the construction of the plant or plant cell constructs described above. A non-limiting example of such a Ti plasmid is pGV3850.

The nucleotide sequence or construct of the present invention should preferably be inserted into the Ti-plasmid between the terminal sequences of the T-DNA or adjacent a T-DNA sequence so as to avoid disruption of the sequences immediately surrounding the T-DNA borders, as at least one of these regions appear to be essential for insertion of modified T-DNA into the plant genome.

As will be understood from the above explanation, if the organism is a plant, then the vector system of the present invention is preferably one which contains the sequences necessary to infect the plant (e.g. the vir region) and at least one border part of a T-DNA sequence, the border part being located on the same vector as the genetic construct. Preferably, the vector system is an *Agrobacterium tumefaciens* Ti-plasmid or an *Agrobacterium rhizogenes* Ri-plasmid or a derivative thereof, as these plasmids are well-known and widely employed in the construction of transgenic plants, many vector systems exist which are based on these plasmids or derivatives thereof.

In the construction of a transgenic plant the nucleotide sequence or construct of the present invention may be first constructed in a microorganism in which the vector can replicate and which is easy to manipulate before insertion into the plant. An example of a useful microorganism is *E. coli*., but other microorganisms having the above properties may be used. When a vector of a vector system as defined above has been constructed in *E. coli*, it is transferred, if necessary, into a suitable *Agrobacterium* strain, e.g. *Agrobacterium tumefaciens*. The Ti-plasmid harbouring the nucleotide sequence or construct of the present invention is thus preferably transferred into a suitable *Agrobacterium* strain, e.g. *A. tumefaciens*, so as to obtain an *Agrobacterium* cell harbouring the nucleotide sequence or construct of the present invention, which DNA is subsequently transferred into the plant cell to be modified.

In this way, the nucleotide or construct of the present invention can be introduced into a suitable restriction position in the vector. The contained plasmid is used for the transformation in *E. coli*. The *E. coli* cells are cultivated in a suitable nutrient medium and then harvested and lysed. The plasmid is then recovered. As a method of analysis there is generally used sequence analysis, restriction analysis, electrophoresis and further biochemical-molecular biological methods. After each manipulation, the used DNA sequence can be restricted and connected with the next DNA sequence. Each sequence can be cloned in the same or different plasmid.

After each introduction method of the desired nucleotide sequence according to the present invention in the plants the presence and/or insertion of further DNA sequences may be necessary. If, for example, for the transformation the Ti- or Ri-plasmid of the plant cells is used, at least the right boundary and often however the right and the left boundary of the Ti- and Ri-plasmid T-DNA, as flanking areas of the introduced genes, can be connected. The use of T-DNA for the transformation of plant cells has been intensively studied and is described in EP-A-120516; Hoekema, in: The Binary Plant Vector System Offset-drukkerij Kanters B. B., Alblasserdam, 1985, Chapter V; Fraley, et al., Crit. Rev. Plant Sci., 4:1-46; and An et al., EMBO J. (1985) 4:277-284.

Direct infection of plant tissues by *Agrobacterium* is a simple technique which has been widely employed and which is described in Butcher D. N. et al. (1980), Tissue Culture Methods for Plant Pathologists, eds.: D. S. Ingrams and J. P. Helgeson, 203-208. For further teachings on this topic see Potrykus (Annu Rev Plant Physiol Plant Mol Biol [1991] 42:205-225) and Christou (Agro-Food-Industry Hi-Tech March/April 1994 17-27). With this technique, infection of a plant may be done on a certain part or tissue of the plant, i.e. on a part of a leaf, a root, a stem or another part of the plant.

Typically, with direct infection of plant tissues by *Agrobacterium* carrying the nucleotide sequence, a plant to be infected is wounded, e.g. by cutting the plant with a razor or puncturing the plant with a needle or rubbing the plant with an abrasive. The wound is then inoculated with the *Agrobacterium*. The inoculated plant or plant part is then grown on a suitable culture medium and allowed to develop into mature plants.

When plant cells are constructed, these cells may be grown and maintained in accordance with well-known tissue culturing methods such as by culturing the cells in a suitable culture medium supplied with the necessary growth factors such as amino acids, plant hormones, vitamins, etc. Regeneration of the transformed cells into genetically modified plants may be accomplished using known methods for the regeneration of plants from cell or tissue cultures, for example by selecting transformed shoots using an antibiotic and by subculturing the shoots on a medium containing the appropriate nutrients, plant hormones, etc.

Further teachings on plant transformation may be found in EP-A-0449375.

Production of the Polypeptide

According to the present invention, the production of the polypeptide of the present invention can be effected by the culturing of, for example, microbial expression hosts, which have been transformed with one or more polynucleotides of the present invention, in a conventional nutrient fermentation medium. The selection of the appropriate medium may be based on the choice of expression hosts and/or based on the regulatory requirements of the expression construct. Such media are well-known to those skilled in the art. The medium may, if desired, contain additional components favouring the transformed expression hosts over other potentially contaminating microorganisms.

Antibodies

The amino acid sequence of the present invention can also be used to generate antibodies—such as by use of standard techniques—against the amino acid sequence. For the production of antibodies, various hosts including goats, rabbits, rats, mice, etc. may be immunized by injection with the inhibitor or any portion, variant, homologue, fragment or derivative thereof or oligopeptide which retains immunogenic properties. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol. BCG (*Bacilli* Calmette-Guerin) and *Corynebacterium parvum* are potentially useful human adjuvants which may be employed.

Monoclonal antibodies to the amino acid sequence may be even prepared using any technique which provides for the production of antibody molecules by continuous cell lines in culture. These include, but are not limited to, the hybridoma technique originally described by Koehler and Milstein (1975 Nature 256:495-497), the human B-cell hybridoma technique (Kosbor et al (1983) Immunol Today 4:72; Cote et al (1983) Proc Natl Acad Sci 80:2026-2030) and the EBV-hybridoma technique (Cole et al (1985) Monoclonal Antibodies and Cancer Therapy, Alan R Liss Inc, pp 77-96). In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851-6855; Neuberger et al (1984) Nature 312:604-608; Takeda et al (1985) Nature 314:452-454). Alternatively, techniques described for the production of single chain antibodies (U.S. Pat. No. 4,946,779) can be adapted to produce inhibitor specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833-3837), and Winter G and Milstein C (1991; Nature 349:293-299).

PROTOCOLS

Protocol 1

Xylanase Assay

Endo-β-1,4-Xylanase Activity

Xylanase samples are diluted in citric acid (0.1M)-di-sodium-hydrogen phosphate (0.2M) buffer, pH 5.0, to obtain approx. OD=0.7 in the final assay. Three dilutions of the sample and an internal standard with a defined activity are thermostated for 5 minutes at 40° C. To time=5 minutes, 1 Xylazyme tab (crosslinked, dyed xylan substrate) is added to the enzyme solution. To time=15 minutes the reaction is terminated, by adding 10 ml of 2% TRIS. The reaction mixture is centrifuged and the OD of the supernatant is measured at 590 nm. Taking into account the dilutions and the amount of xylanase, the activity (TXU, Total-Xylanase-Units) of the sample can be calculated relatively to the standard.

Protocol 2

Stickiness Protocol

Stickiness Determination

Dough stickiness is measured on a TA-XT2 system (Stable Micro Systems) using a SMS Dough Stickiness Cell. The protocol is a modified version of the method described by Chen and Hoseney (1995). A dough is made from flour, 2% NaCl and water to 400 Brabender Units (BU) using a Farinograph (AACC method 54-21). The flour and NaCl is dry mixed for 1 minute. Water is added and the dough is mixed for another 5 minutes. The obtained dough could advantageously be rested for 10, 30 or 45 minutes in sealed containers at 30° C.

Approx. 4 gram dough is placed in the Dough Stickiness Cell. 4 mm dough is extruded to obtain an uniform extrusion. Hereafter 5 measurement are made according to Stable Micro Systems protocol (TA-XT2 application study for measurement of dough stickiness). In brief, 1 mm dough is extruded. The probe (25 mm perspex cylinder probe), connected to the TA-XT2 system, is pressed into the extruded dough at a set force. The probe is raised and the adhesion between the dough and the probe is recorded. The following TA-XT2 setting are used:

| Option: | Adhesive test |
|---|---|
| Pre-test speed: | 2.0 mm/s |
| Test speed: | 2.0 mm/s |
| Post-test speed: | 10.0 mm/s |
| Distance: | 15 mm |
| Force: | 40 g |
| Time: | 0.1 s |
| Trigger Type: | Auto - 5 g |
| Data Acquisition rate: | 400 pps |

The results recorded from the test are peak force, meaning the force needed to raise the probe from the extruded dough. The distance, meaning the distance the dough attach to the probe. Area, meaning area below the obtained curve.

Dough stickiness is depending on the quality of the flour used and the recipe. Therefore a non-sticky dough is a dough differing in stickiness from 100% to 200% (relative) compared to a reference dough, without the xylanase or having preferably less than 70% (relative) of the stickiness obtained with a commercial fungal xylanase (i.e. Pentopan mono BG, Novo Nordisk) when dosed at a levels giving the same volume increase in a baking trial.

Protocol 3

Inhibitor Assay Protocol

Inhibitor Assay

To detect the inhibitor during isolation and characterisation the following assay is used. 100 µl inhibitor fraction, 250 µl xylanase solution (containing 12 TXU/ml) and 650 µl buffer (0.1 M citric acid-0.2M di-sodium hydrogen phosphate buffer, pH 5.0) is mixed. The mixture is thermostated for 5 minutes at 40.0° C. At time=5 minutes one Xylazyme tab is added. At time=15 minutes the reaction is terminated by adding 10 ml 2% TRIS. The reaction mixture is centrifuged (3500 g, 10 minutes, room temperature) and the supernatant is measured at 590 nm. The inhibition is calculated as residual activity compared to the blank. The blank is prepared the same way, except that the 100 µl inhibitor is substituted with 100 µl buffer (0.1 M citric acid-0.2 M di-sodium hydrogen phosphate buffer, pH 5.0). By way of example, XM-1 may be considered to have a high degree of resistance to the inhibitor (see FIG. 20). XM-2 and XM-3 may be considered to have a medium degree of resistance to the inhibitor (see FIG. 20).

Protocol 4

Glucanase Protocol I

Endo-β-1,4-Glucanase Activity

Glucanase samples are diluted in 0.1M sodium-acetate-citric acid buffer, pH=5.0, to obtain approx. OD=0.7 in the final assay. Three dilutions of the sample and an internal standard with a defined activity are thermostated for 5 minutes at 40° C. To time=5 minutes, 1 Glucazyme tab (crosslinked, dyed glucan substrate) is added to the enzyme solution. To time=15 minutes the reaction is terminated, by adding 10 ml of 2% TRIS. The reaction mixture is centrifuged and the OD of the supernatant is measured at 590 nm. Taking into account the dilutions and the amount of glucanase, the activity (BGU, Beta-Glucanase-Units) of the sample can be calculated relatively to the standard.

Protocol 5

Inhibitor Assay Protocol II

Inhibitor Kinetics Assay

To study kinetics on the inhibitor a soluble substrate was used (Azo-xylan, Megazyme). A 2% (w/v) solution of the substrate was prepared, according to manufacturers protocol, in 20 mM NaPi, pH 6.0. The assay was performed by pre-heating substrate, xylanase and inhibitor at 40° C. for 5 minutes.

For a preliminary inhibitor characterisation, the xylanase used is diluted to 40 TXU/ml. For $K_i$ determinations, the xylanases are diluted to approx. 40 TXU/ml.

0.5 ml of substrate, 0.1 ml of xylanase and 0.1 ml of inhibitor was mixed at time=0 minutes, 40° C. At time=125 minutes, the reaction was terminated by adding 2 ml of ethanol (95%), followed by vortexing for 10 seconds. Precipitated unhydrolysed substrate was removed by centrifugation (3500×g, 10 minutes, room temperature). OD in the supernatant was measured against water at 590 nm.

A blank was prepared the same way. The only modification was substitution of the inhibitor with 20 mM NaPi, pH 6.0.

For kinetic experiments with decreased substrate concentration, the following substrate concentrations were made by dilution in 20 mM NaPi, pH 6.0. 2%, 1%, 0.5% and 0.25% soluble azo-xylan (w/v).

For $K_i$ determinations the above mentioned xylanases and substrate concentrations were used. These were combined with the following concentrations of inhibitor extract in the assay: 0, 2, 5, 10, 25, 50 and 100 µl in the assay. Using µl inhibitor and not a molar concentration of the inhibitor, $K_i$ is expressed as µl inhibitor.

SUMMARY

In summary the present invention provides inter alia:
a. The isolation of an endogenous endo-β-1,4-xylanase inhibitor from wheat flour.
b. The characterisation of an endogenous endo-β-1,4-xylanase inhibitor isolated from wheat flour.
c. The characterisation of the effect of endogenous endo-β-1,4-xylanase inhibitor on different xylanases.
d. A means for selecting xylanases not detrimentally affected by endogenous endo-β-1,4-xylanase inhibitor.
e. A means for selecting xylanases which are not detrimentally affected by endo-β-1,4-xylanase inhibitors.

f. Xylanases that provide dough exhibiting favourable volume and acceptable stickiness than when compared to doughs comprising fungal xylanases.

g. A method for screening xylanases and/or mutating the same using an endogenous endo-β-1,4-xylanase inhibitor, and the use of those xylanases or mutants thereof in the manufacture of doughs.

h. A foodstuff prepared with the xylanases of the present invention.

DEPOSITS

The following samples were deposited in accordance with the Budapest Treaty at the recognised depositary The National Collections of Industrial and Marine Bacteria Limited (NCIMB) at 23 St. Machar Drive, Aberdeen, Scotland, United Kingdom, AB2 1RY on 22 December 1998:

| | |
|---|---|
| DN5α::pCR2.1__BS xylanase | NCIMB number NCIMB 40999 |
| BL21(DE3)::pET24A__XM1 | NCIMB number NCIMB 41000 |
| BL21(DE3)::pET24A__XM3 | NCIMB number NCIMB 41001 |

DH5α::pCR2.1__BS xylanase comprises wild type xylanase.
BL21(DE3)::pET24A__XM1 comprises XM1 xylanase.
BL21(DE3)::pET24A__XM3 comprises XM3 xylanase.

The present invention also encompasses sequences derivable and/or expressable from those deposits and embodiments comprising the same.

INTRODUCTION TO THE EXAMPLES SECTION AND THE FIGURES

Figure 2:
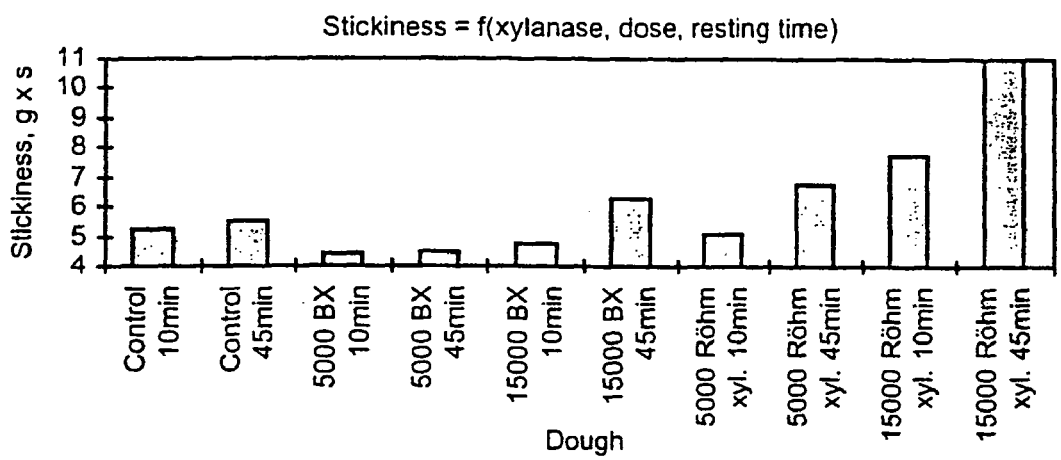
Figure 3:
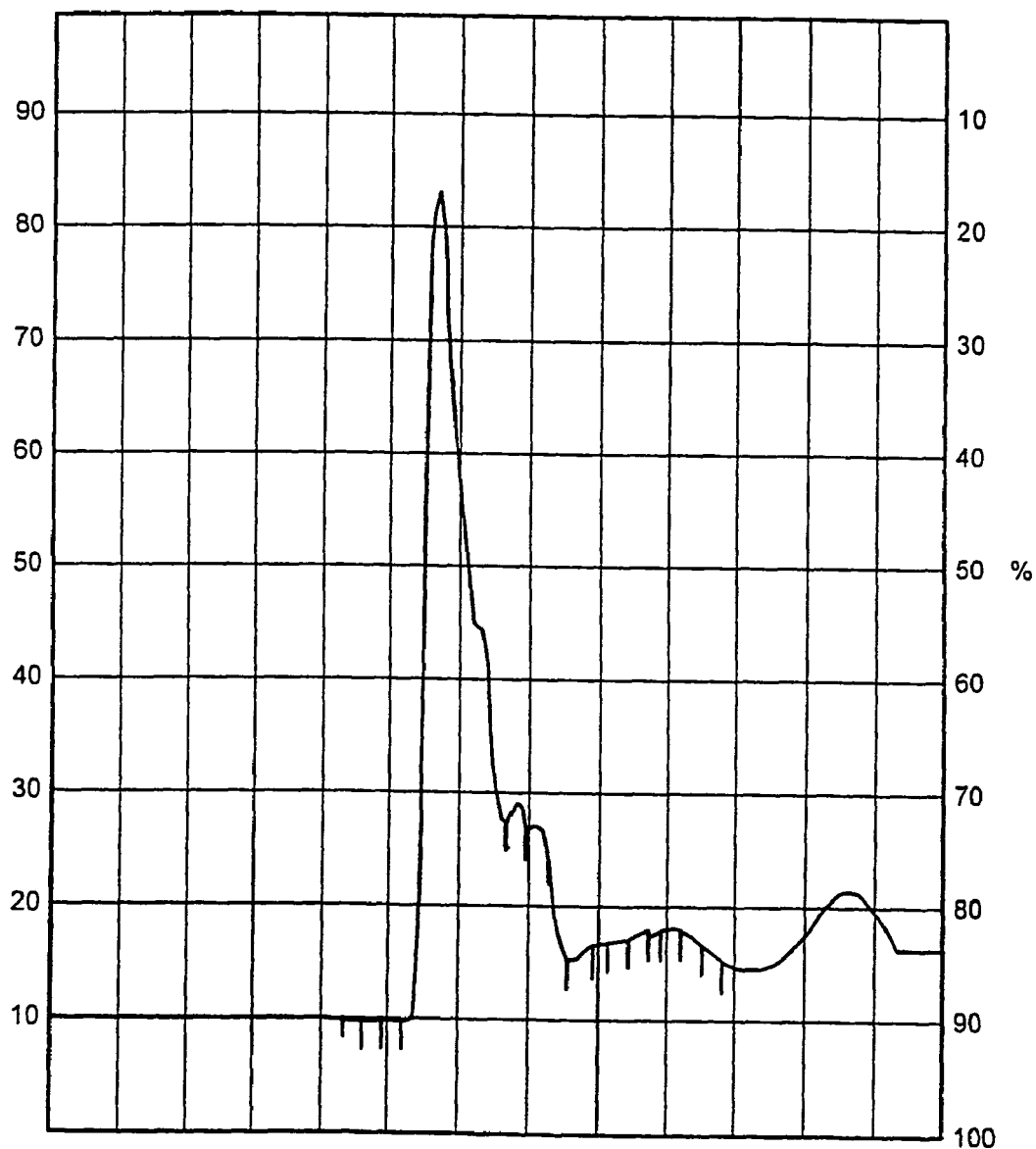
Figure 4:
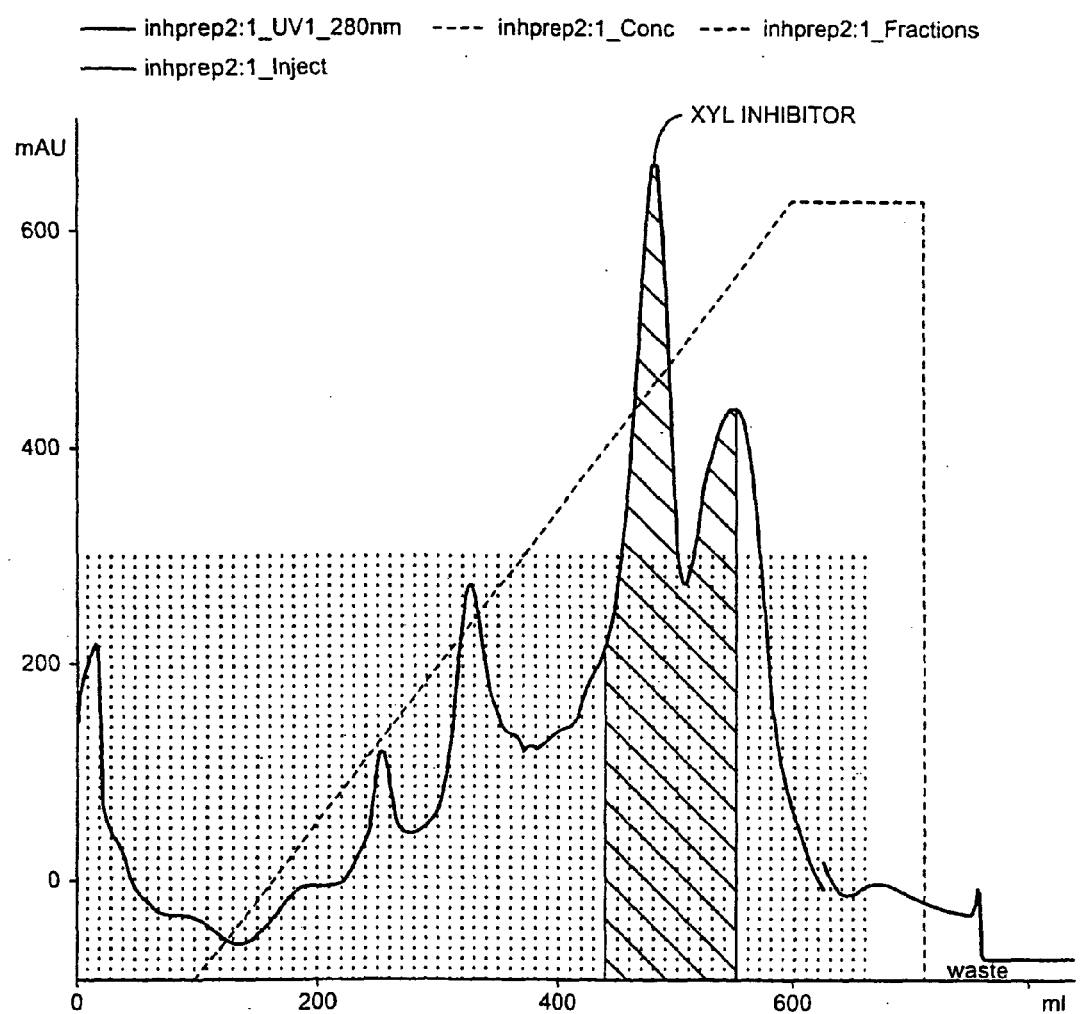
Figure 5:
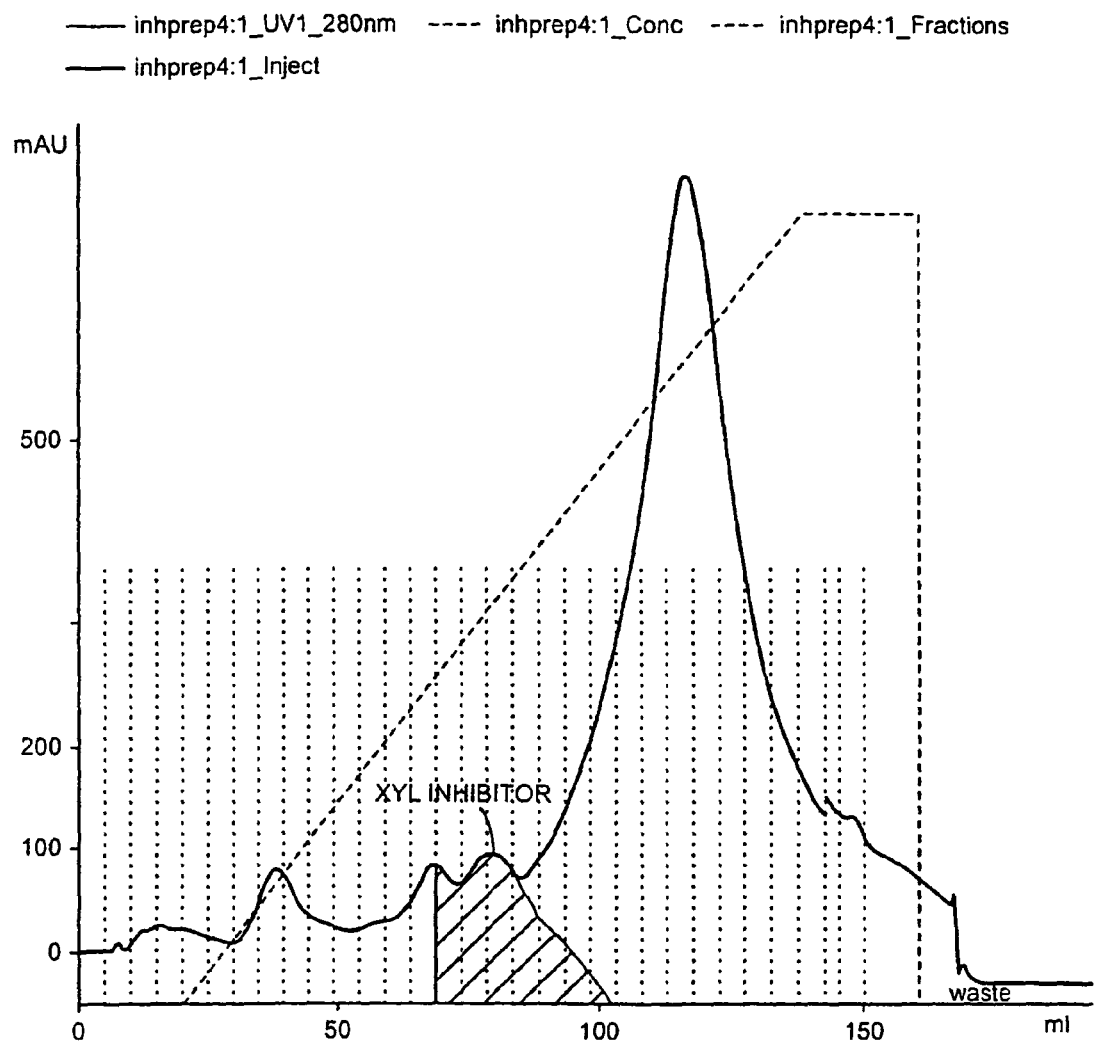
Figure 6:
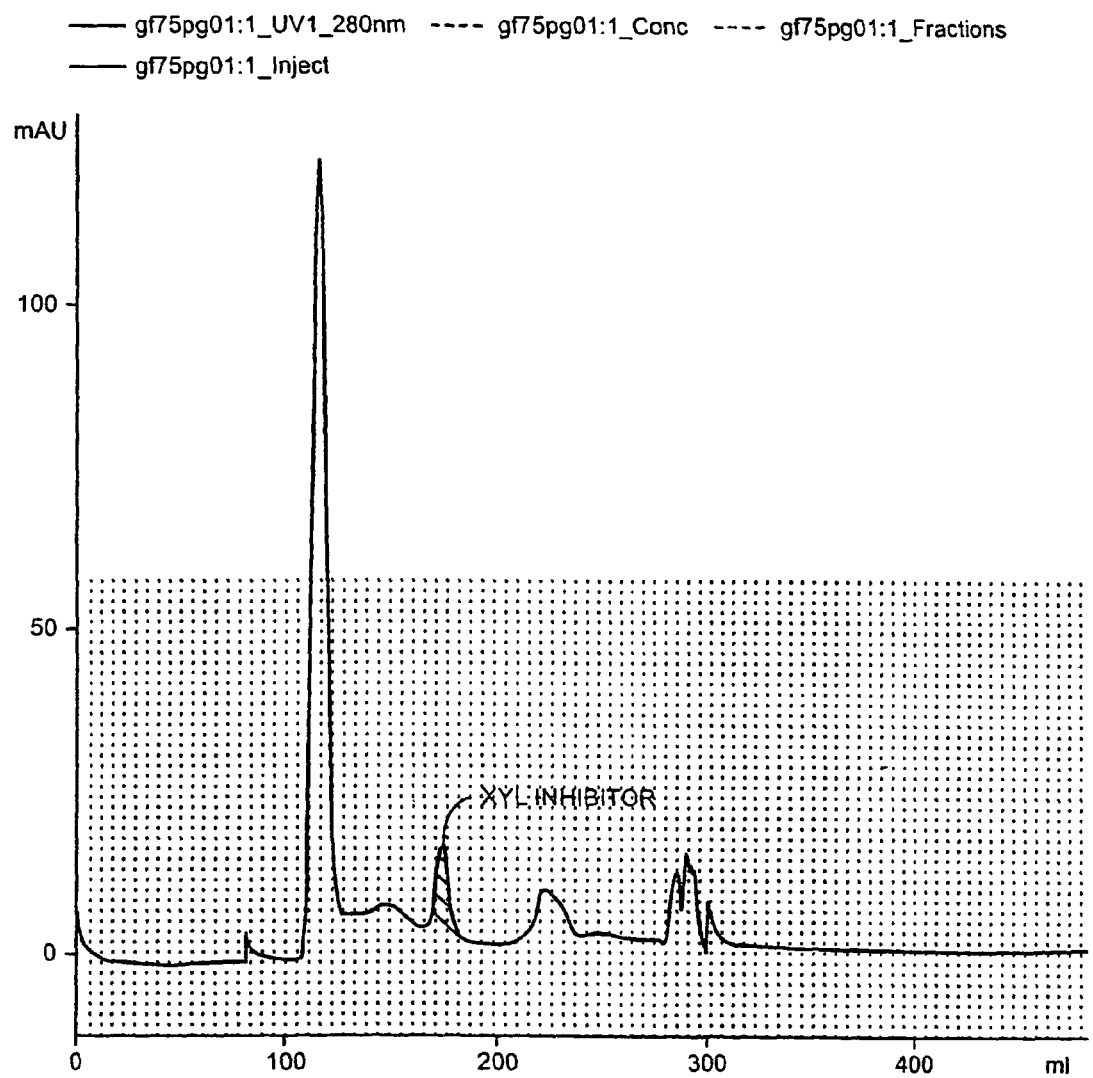
Figure 7:
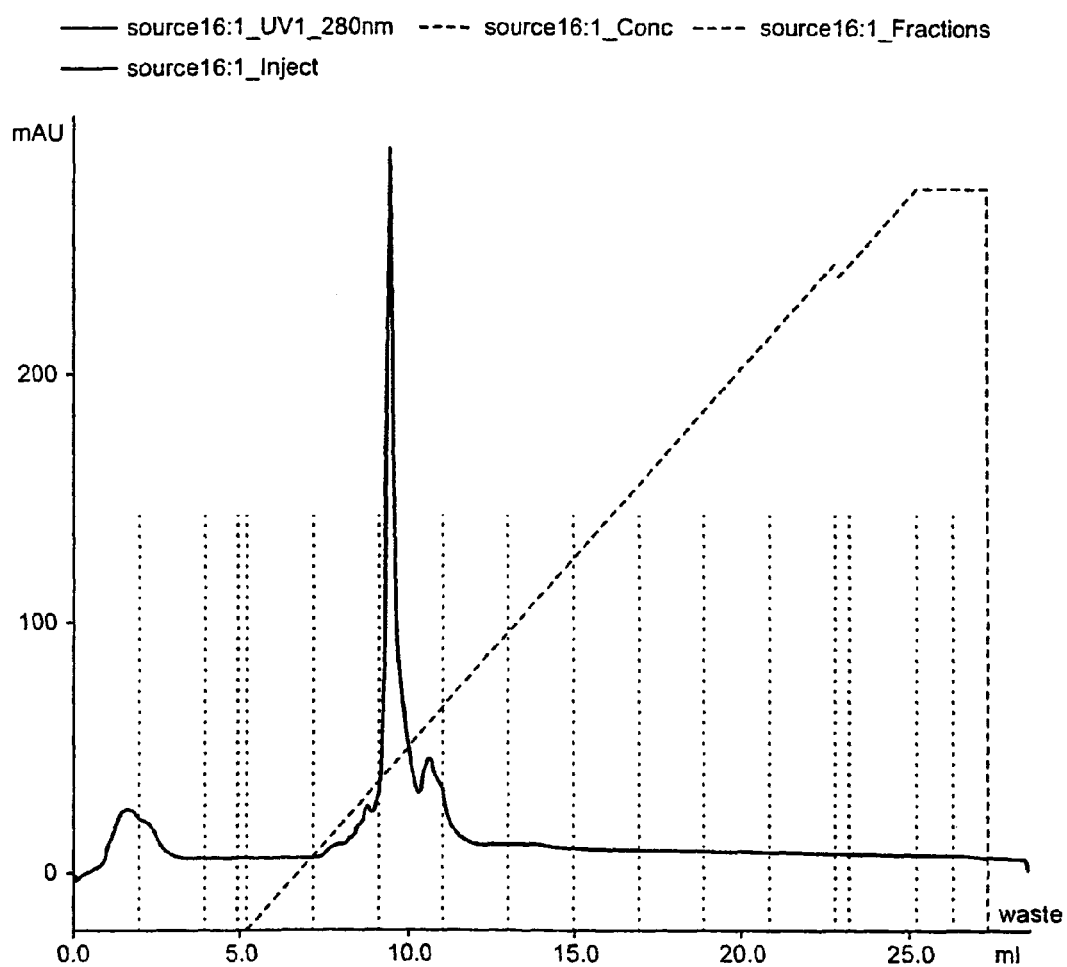
Figure 8:
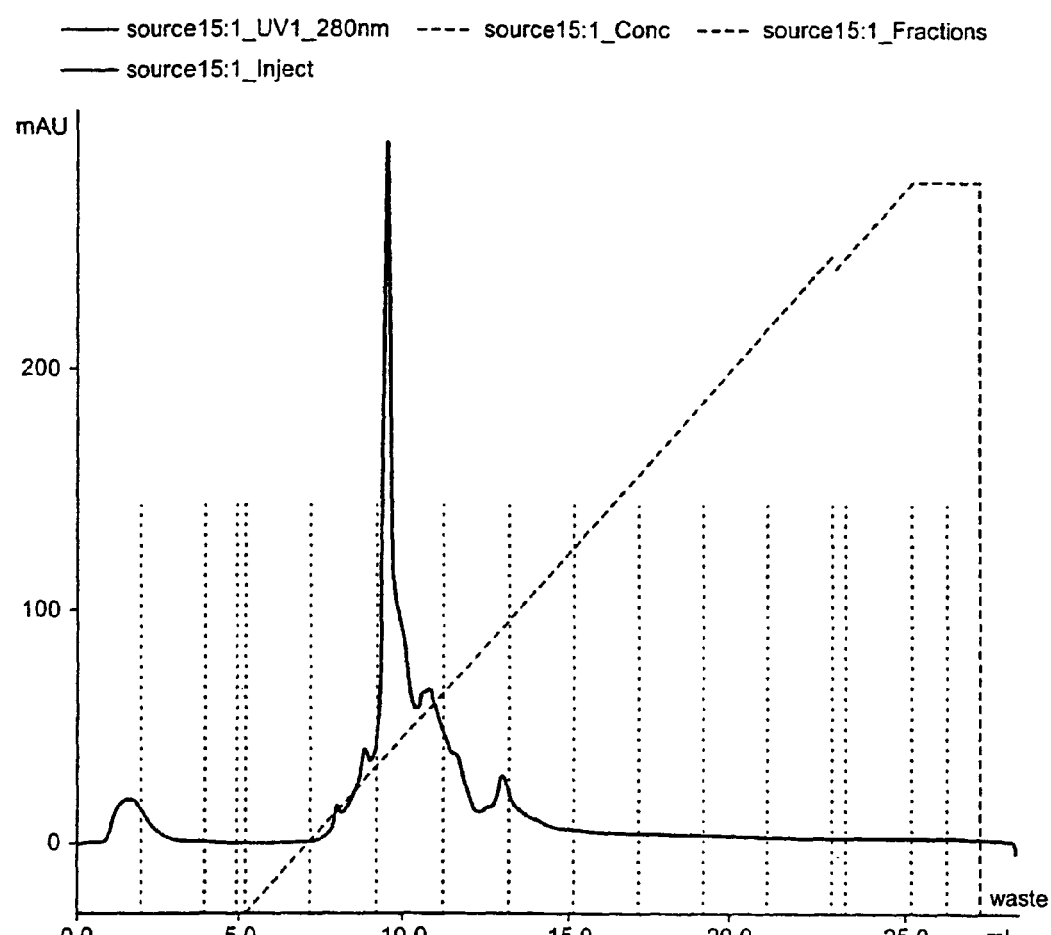
Figure 9:
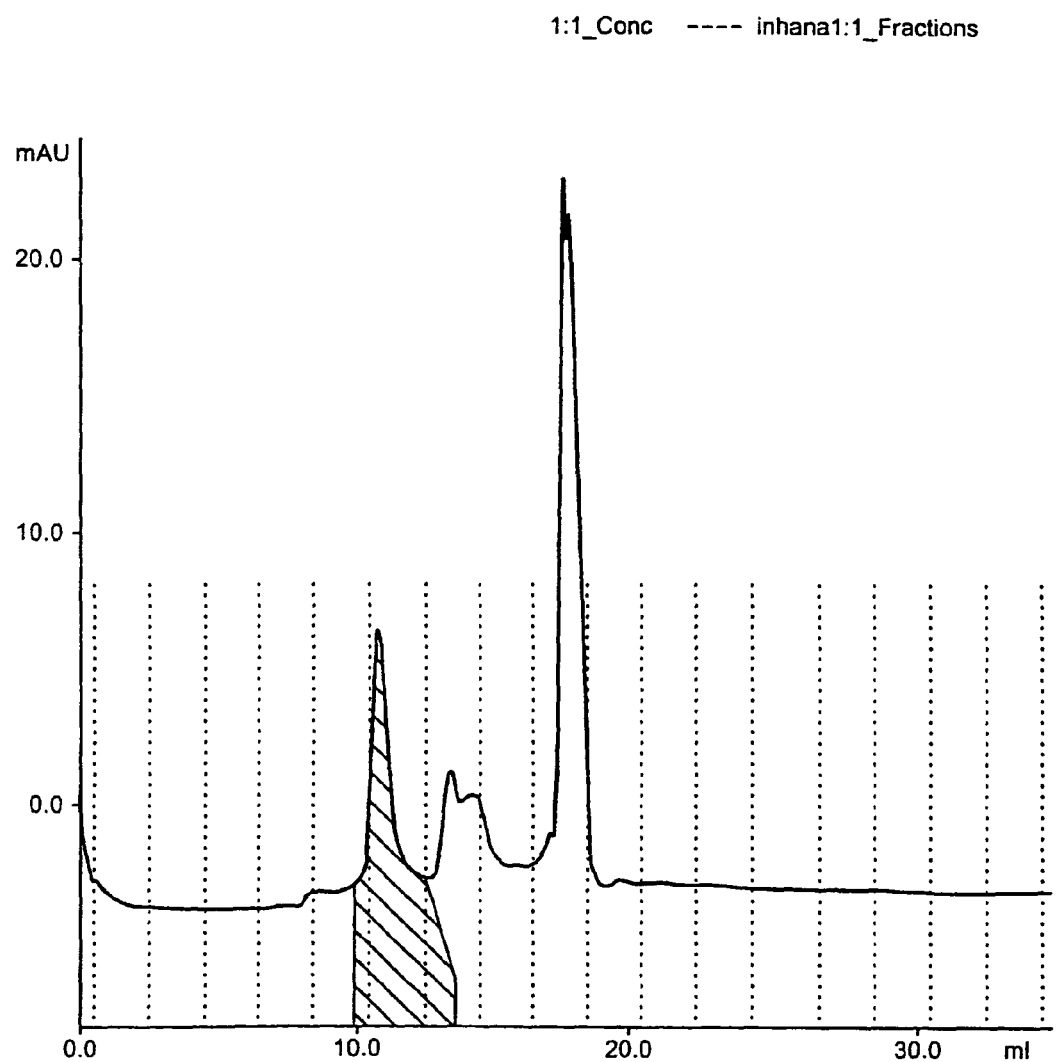
Figure 10:
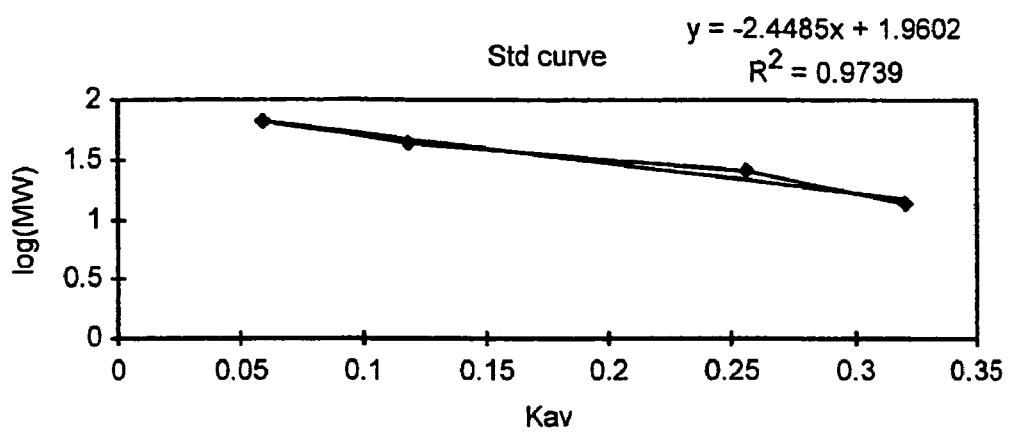
Figure 11:
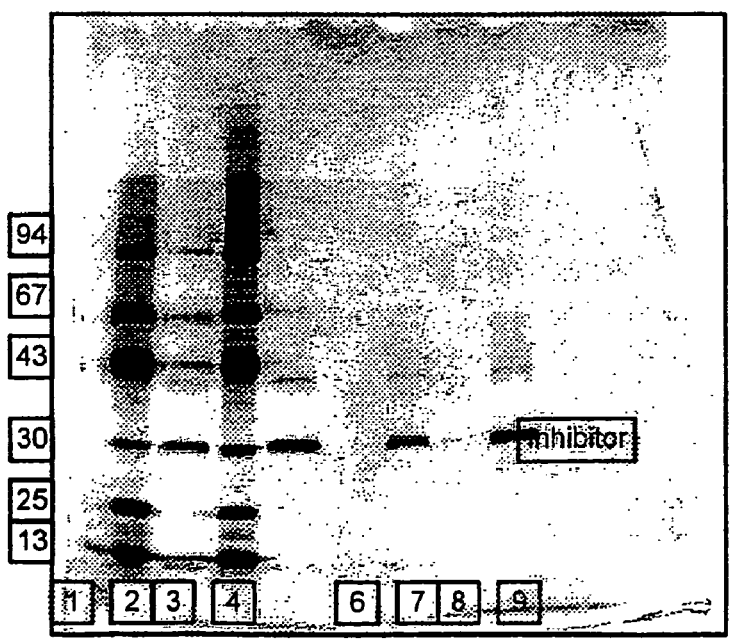
Figure 12:
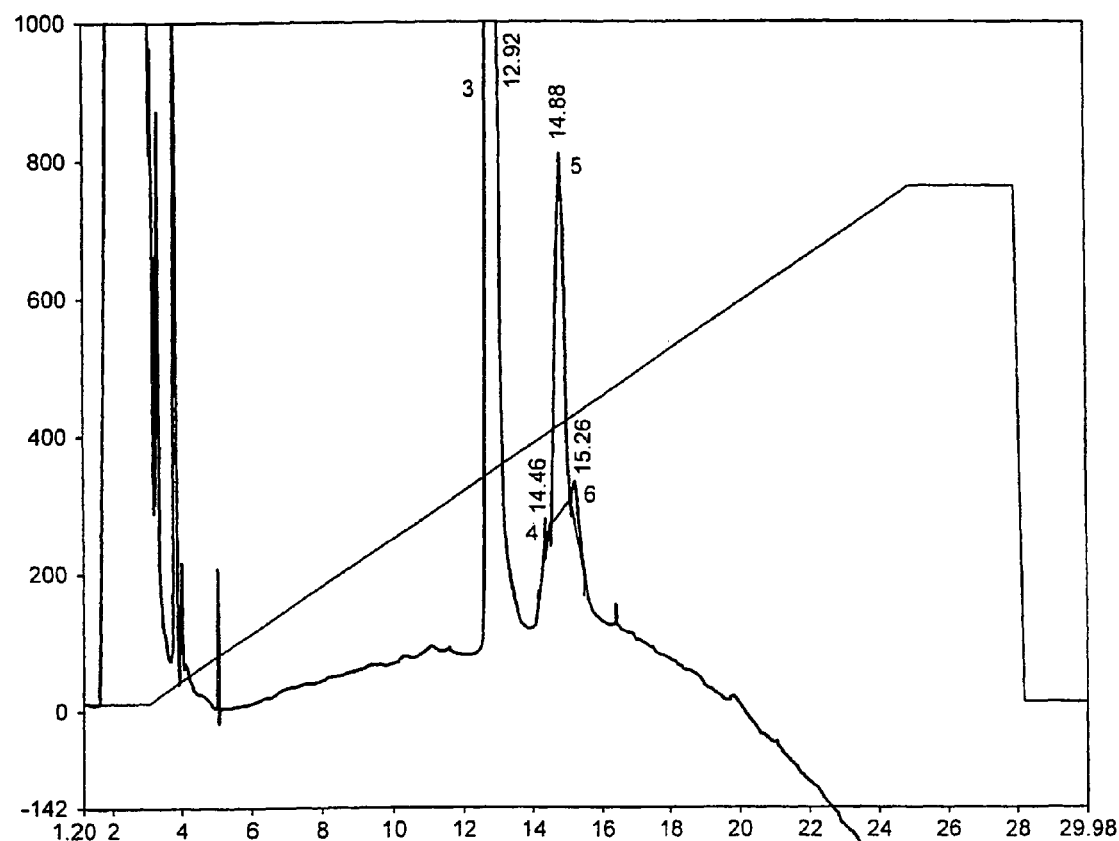
Figure 13:
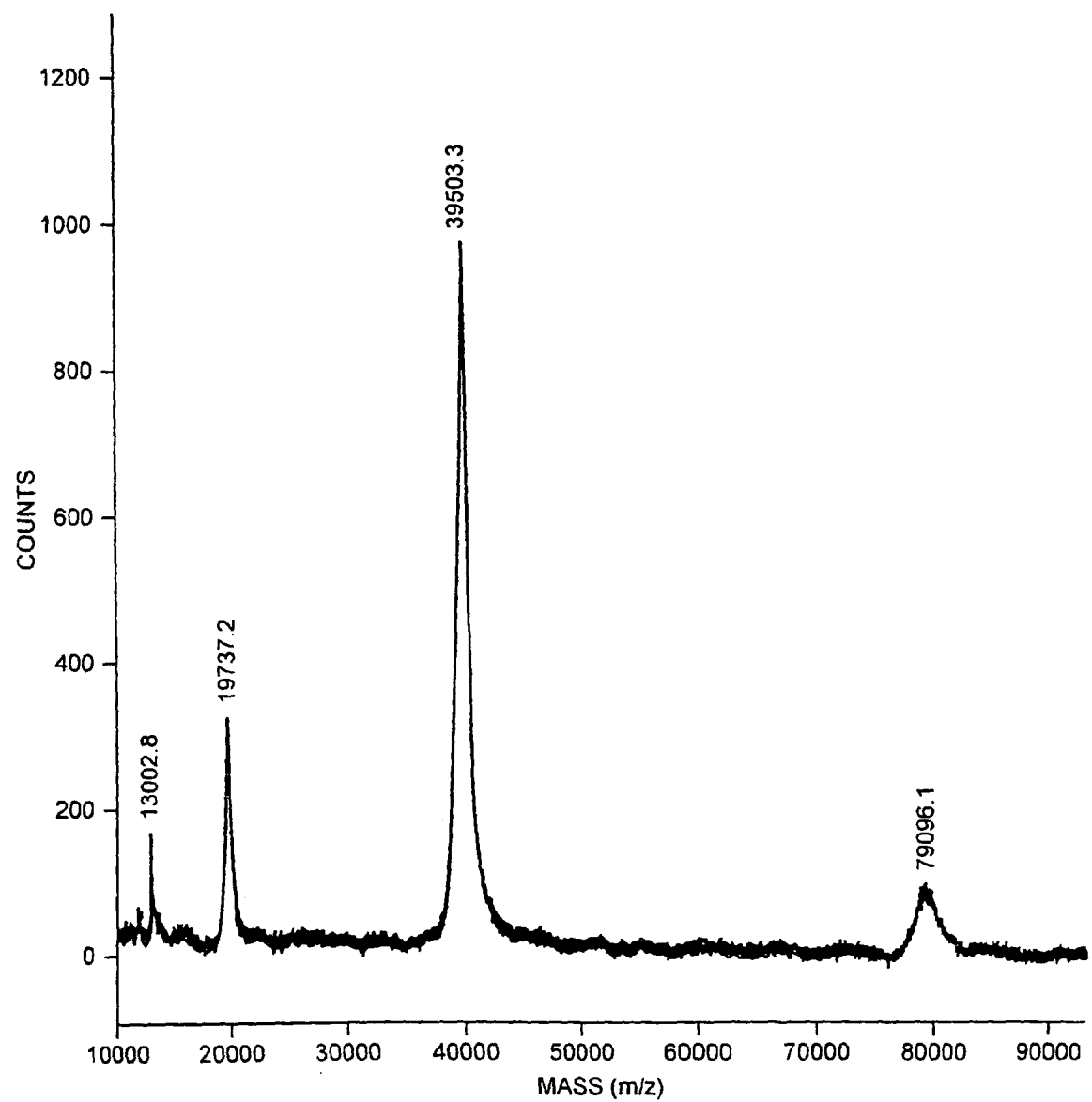
Figure 14:
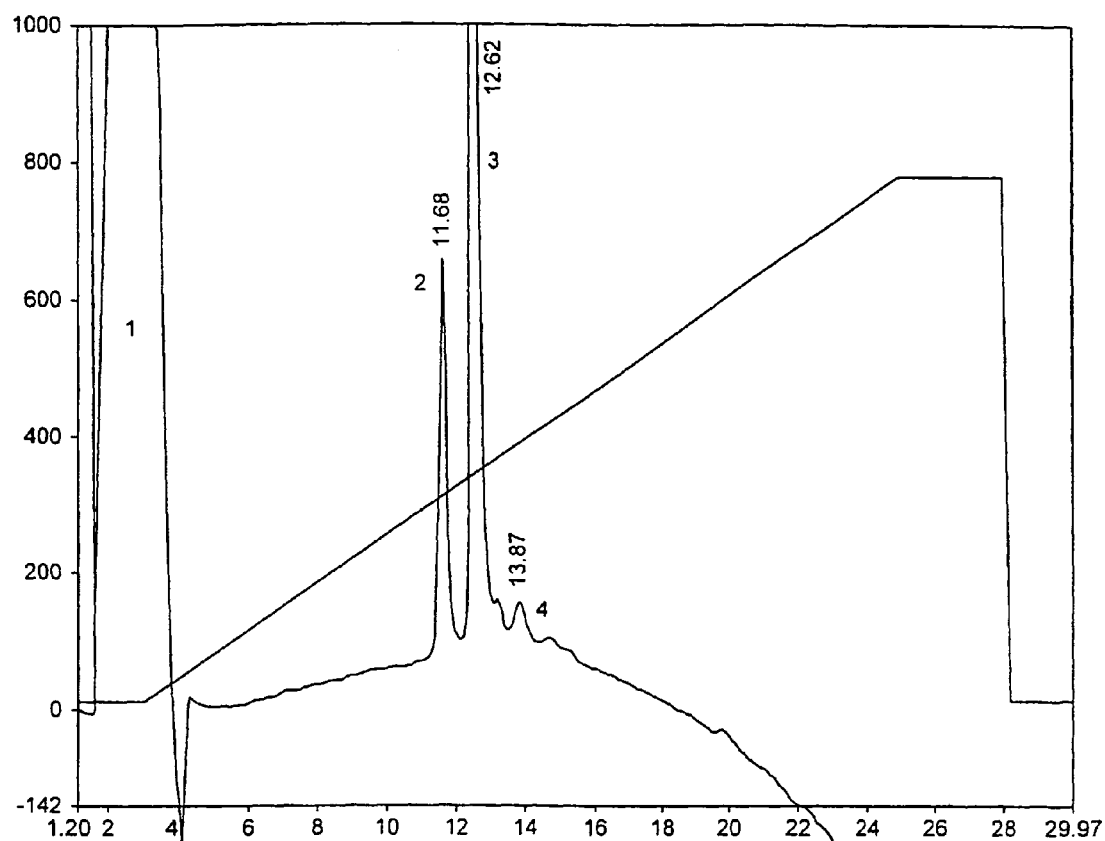
Figure 15:
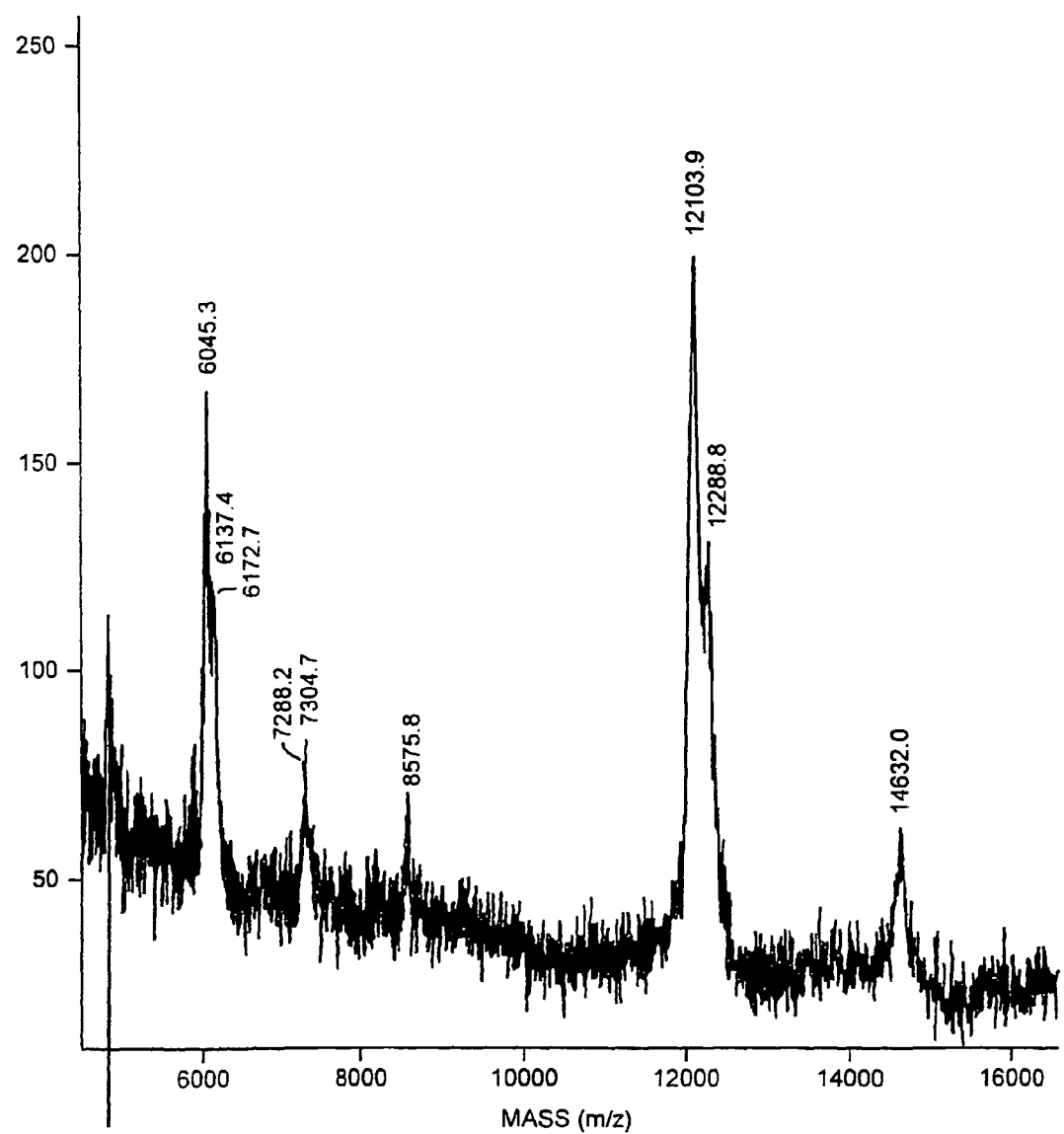
Figure 16:
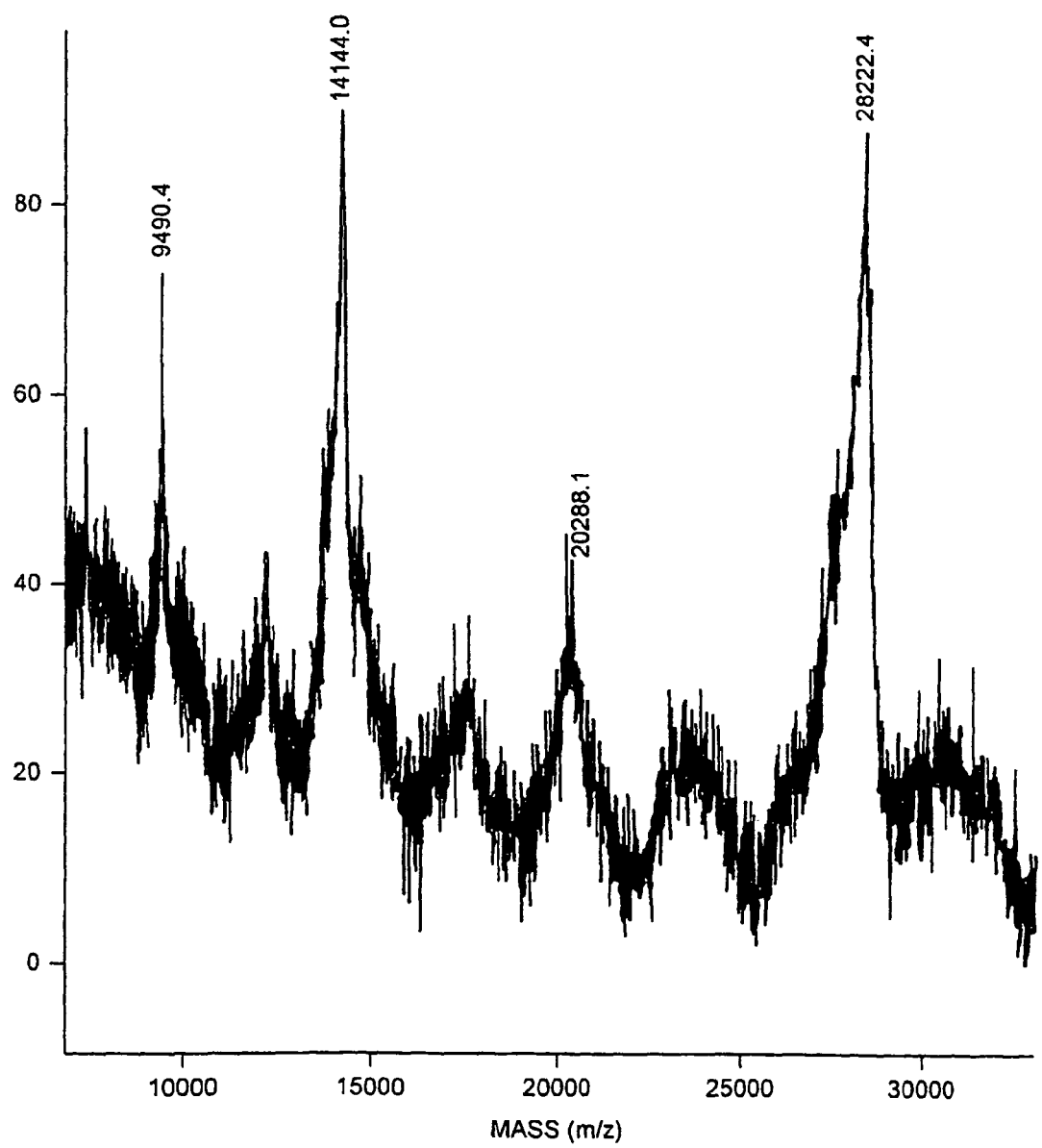
Figure 17:
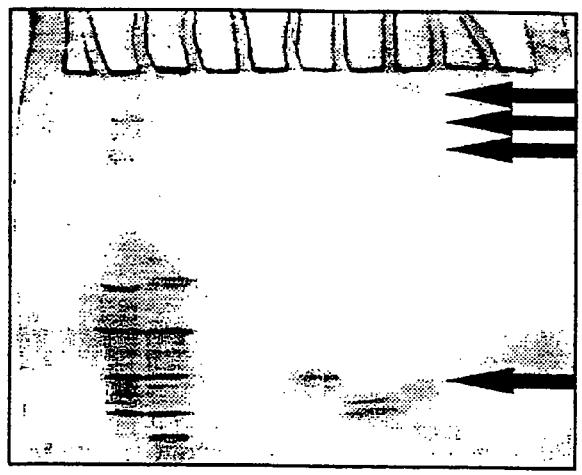
Figure 18:
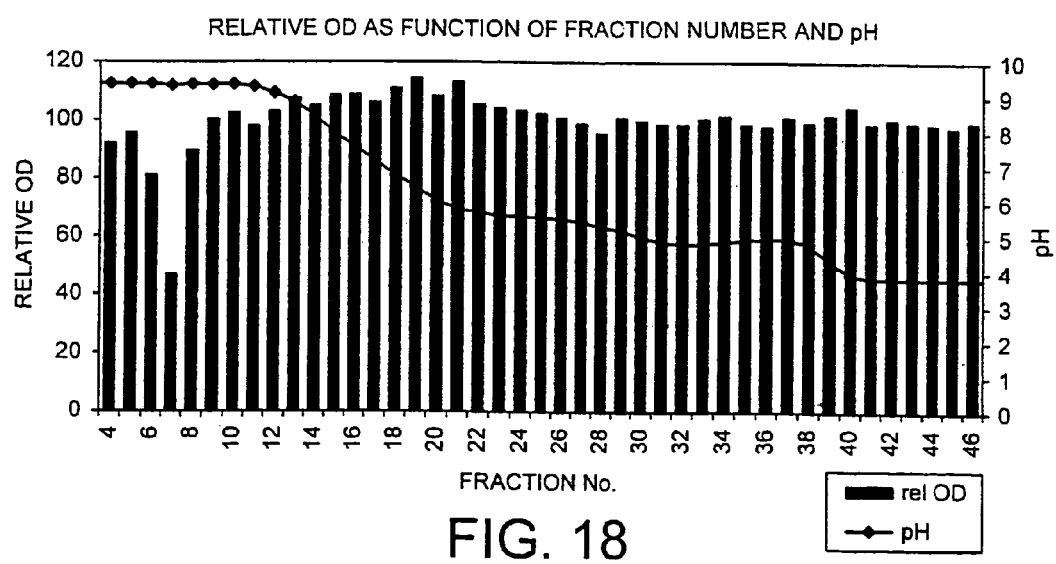
Figure 19:
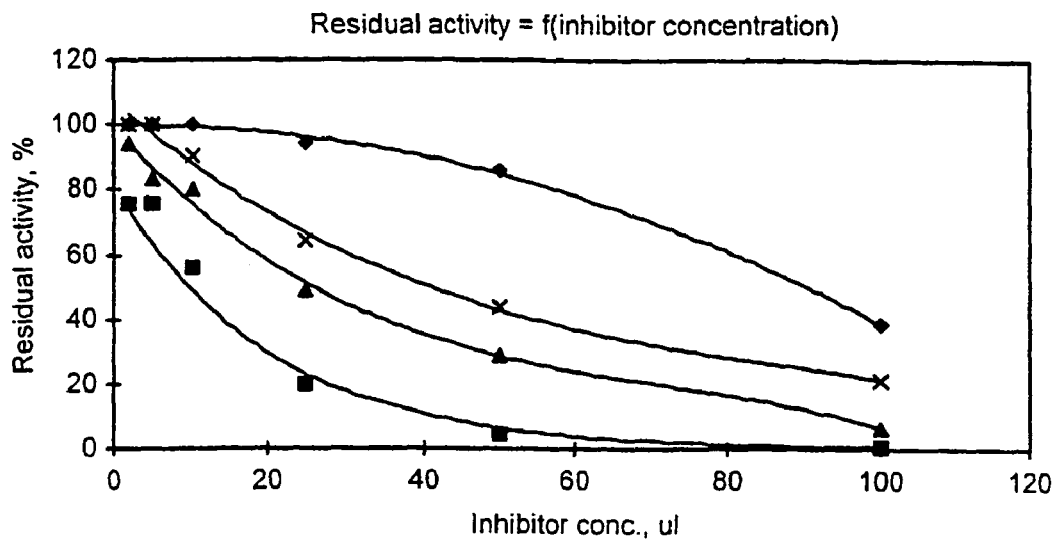
Figure 20:
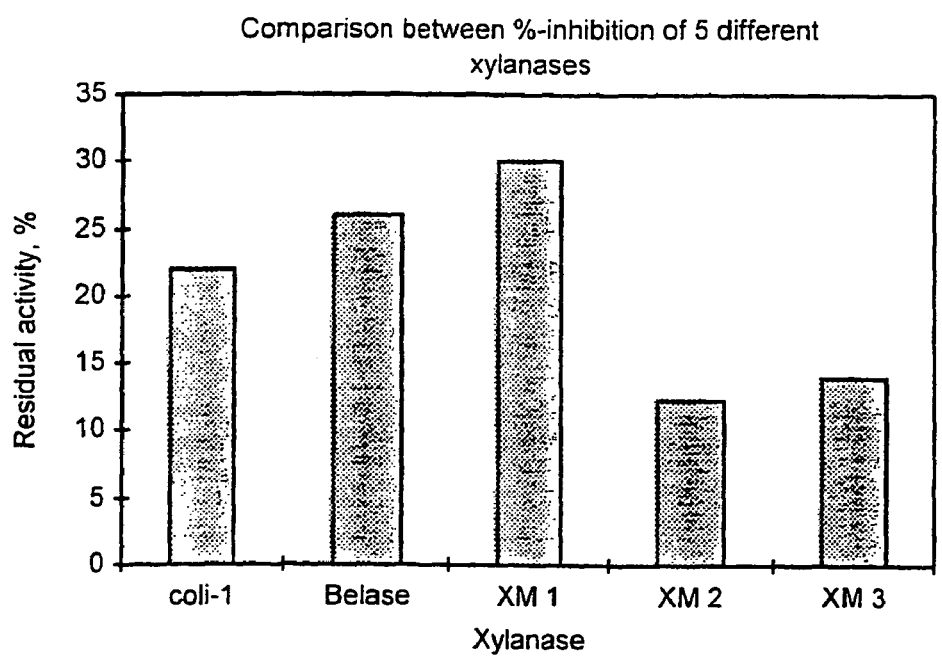
Figure 21:
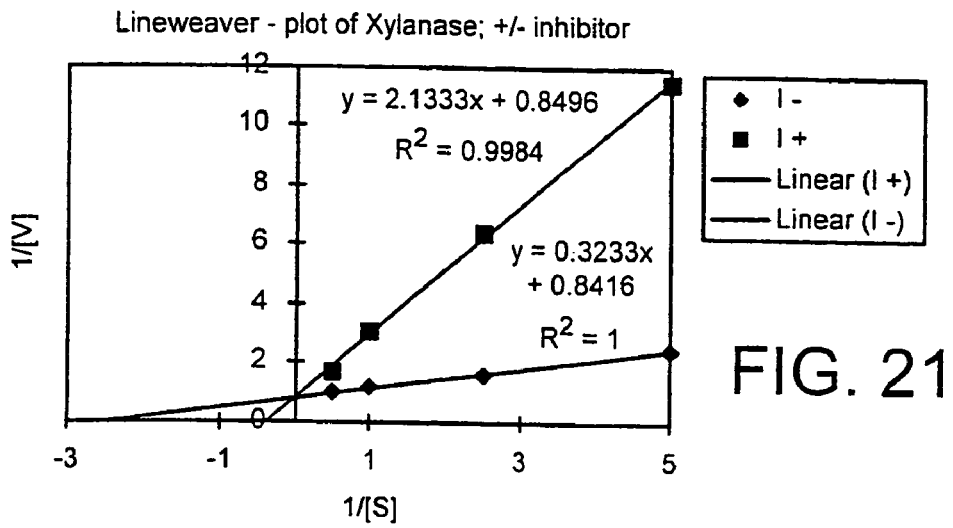
Figure 22:
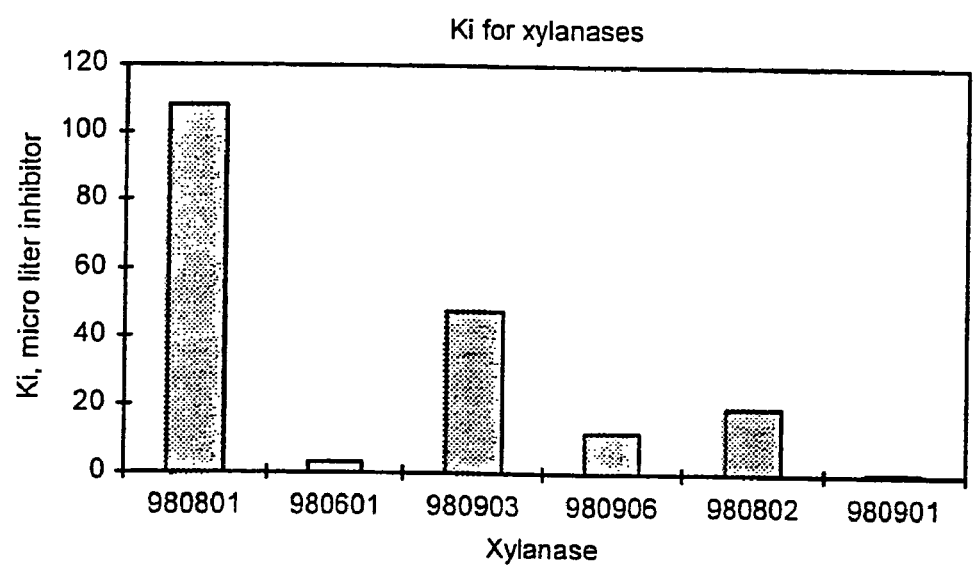
Figure 23:
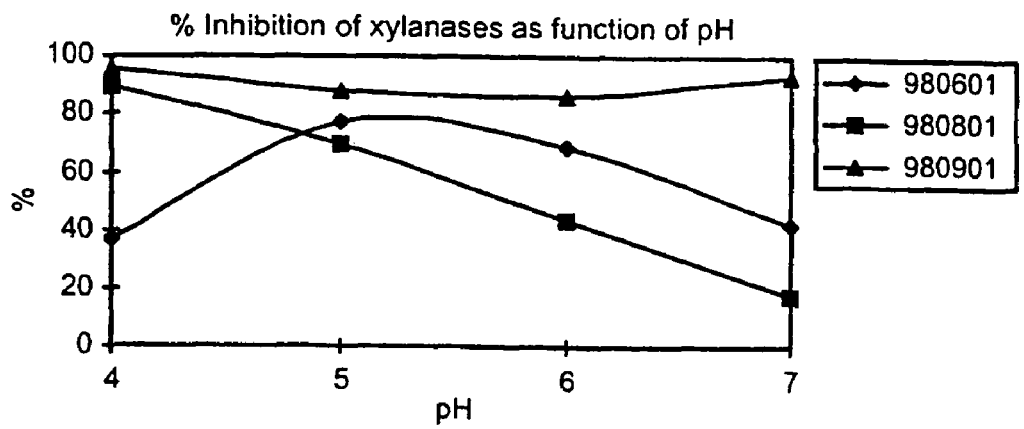
Figure 24:
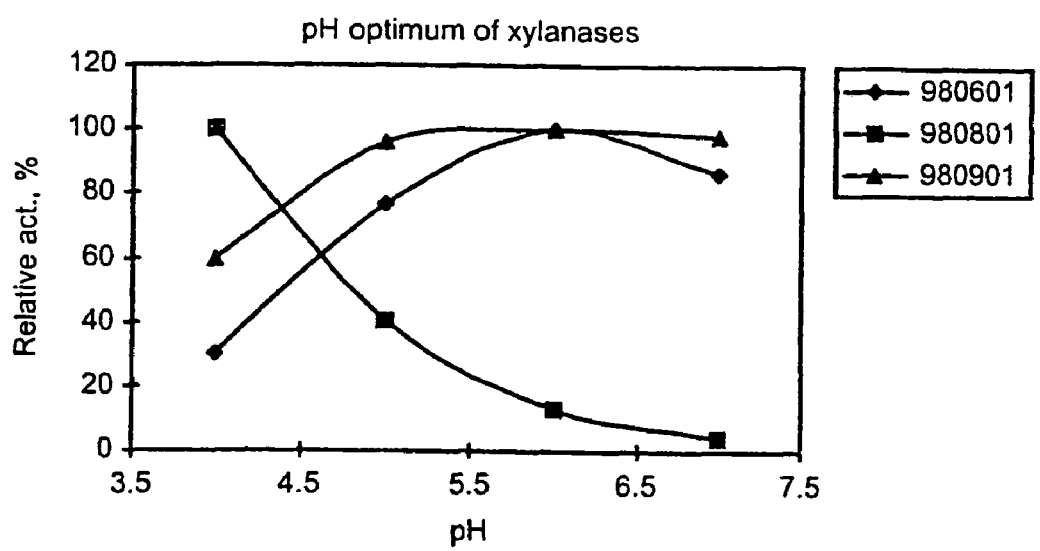
Figure 25:
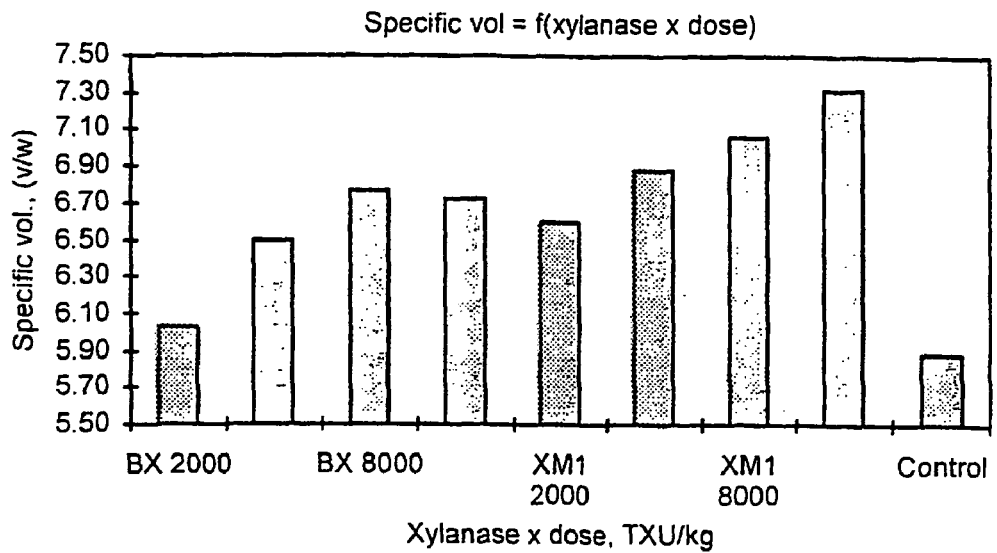
Figure 26:
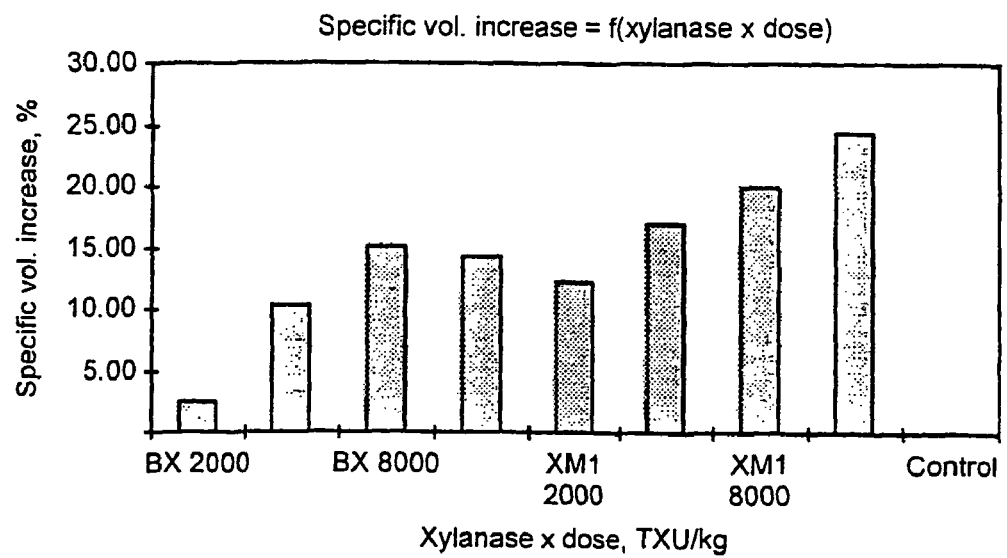
Figure 27:
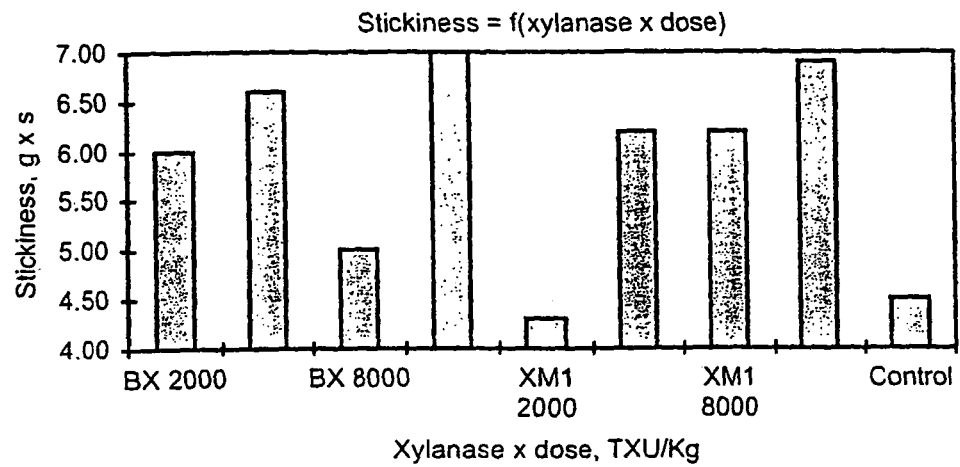
Figure 28:
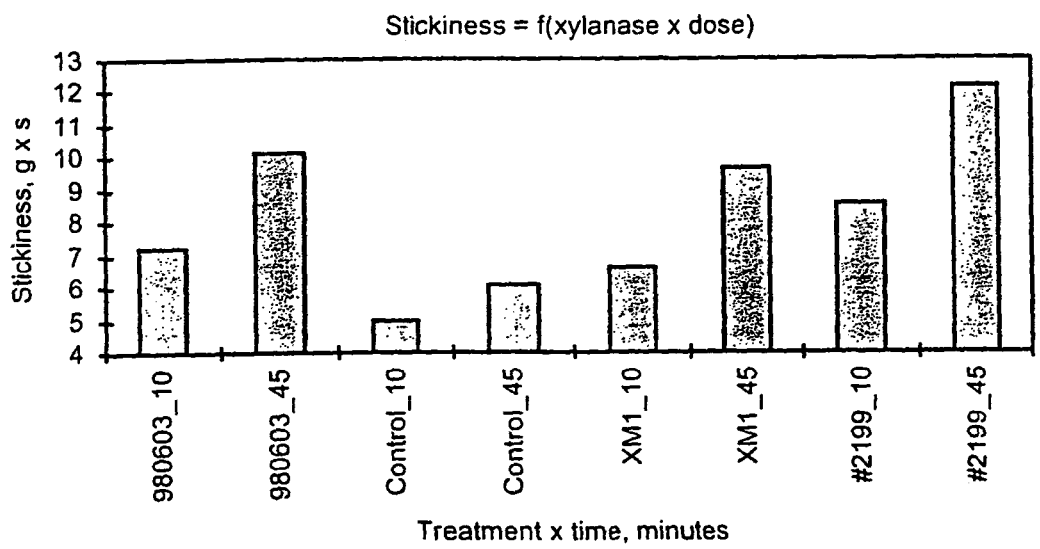
Figure 29:
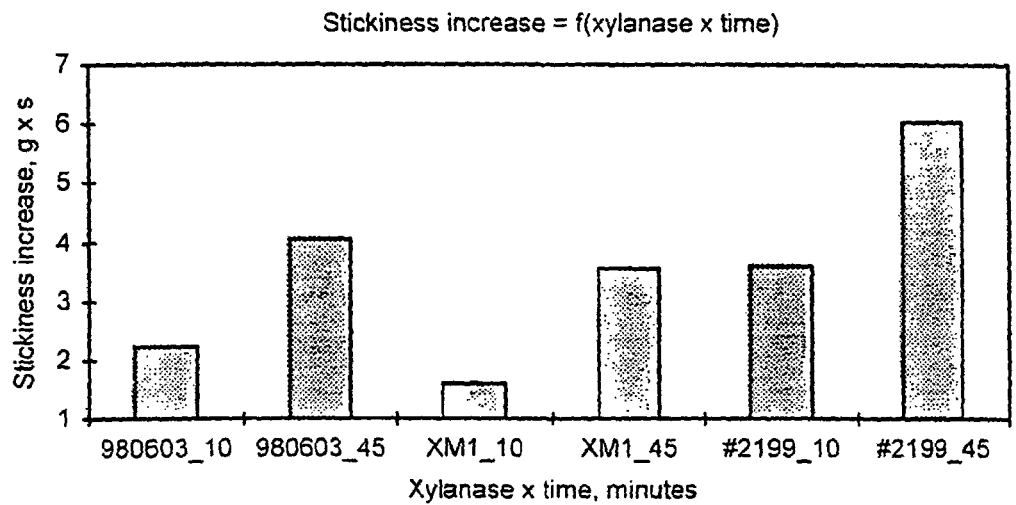
Figure 30:
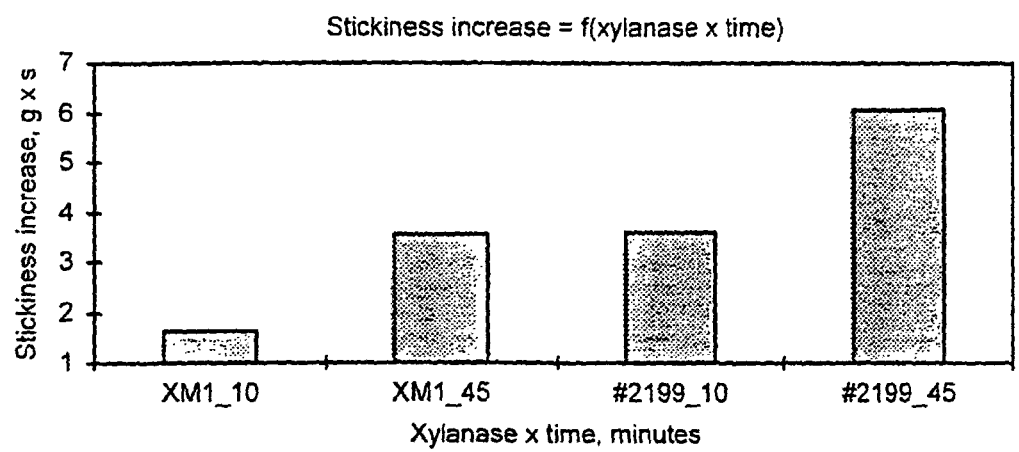
Figure 31:
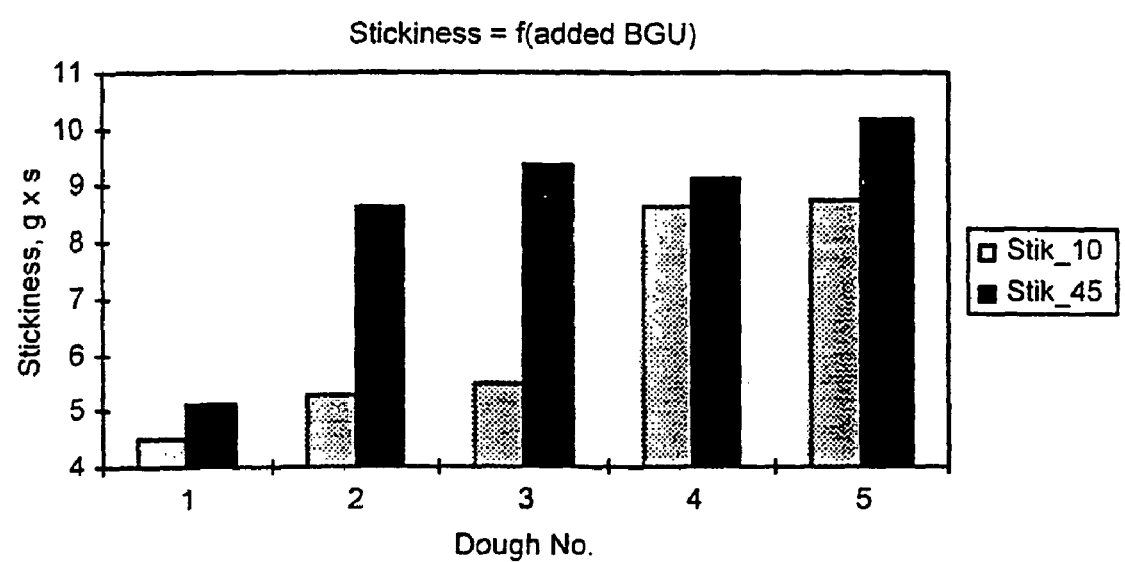

The present invention will now be described, by way of example only, with reference to the accompanying drawings in which:

FIG. 1 shows a graph;
FIG. 2 shows a graph;
FIG. 3 shows a graph;
FIG. 4 shows a graph;
FIG. 5 shows a graph;
FIG. 6 shows a graph;
FIG. 7 shows a graph;
FIG. 8 shows a graph;
FIG. 9 shows a graph;
FIG. 10 shows a graph;
FIG. 11 shows an image result of an SDS PAGE experiment;
FIG. 12 shows a graph;
FIG. 13 shows a graph;
FIG. 14 shows a graph;
FIG. 15 shows a graph;
FIG. 16 shows a graph;
FIG. 17 shows an image result of an IEF experiment;
FIG. 18 shows a graph;
FIG. 19 shows a graph;
FIG. 20 shows a graph;
FIG. 21 shows a graph;
FIG. 22 shows a graph;
FIG. 23 shows a graph;
FIG. 24 shows a graph;
FIG. 25 shows a graph;
FIG. 26 shows a graph;
FIG. 27 shows a graph;
FIG. 28 shows a graph;
FIG. 29 shows a graph;
FIG. 30 shows a graph; and
FIG. 31 shows a graph.

In slightly more detail:

FIG. 1—Stickiness as a function of xylanases, dose and resting time.

FIG. 2—Stickiness as a function of xylanases, dose and resting time.

FIG. 3—Gel filtration chromatography of a 75 ml inhibitor extract sample. Column: 500 ml Superdex G-25 F, Flow: 10 ml/min, Fraction size: 30 ml.

FIG. 4—Cation exchange chromatography of a 240 ml gel filtrated inhibitor extract sample. Column: 50 ml Sepharose SP, Flow: 5.0 ml/min, Fraction size: 10 ml.

FIG. 5—HIC chromatography of a 147 ml ion exchanged inhibitor extract sample added $(NH_4)_2SO_4$ to 1.0M. Column: 10 ml Phenyl HIC, Flow: 2.0 ml/min, Fraction size: 2.5 ml.

FIG. 6—Preparative gel filtration chromatography of 2 ml concentrated inhibitor sample. Inhibitor eluted at 176 ml. Column: 330 ml Superdex 75 PG (Pharmacia). Eluent: 50 mM NaOAc, 200 mM NaCl, pH 5.0. Flow: 1 ml/minute. Fraction size: 5.5 ml.

FIG. 7—Cation exchange chromatogram of pure xylanase+boiled inhibitor extract. Sample: 1 ml desalted 980601+boiled inhibitor extract. Column: 1 ml Source S 15. Buffer system: A: 50 mM NaOAc, pH 4.5, B: A+1 M NaCl. Flow: 2 ml/minute.

FIG. 8—Cation exchange chromatogram of pure xylanase after three hours incubation with inhibitor extract. Sample: 1 ml desalted 980601+inhibitor. Column: 1 ml Source S 15. Buffer system: A: 50 mM NaOAc, pH 4.5, B: A+1 M NaCl. Flow: 2 ml/minute.

FIG. 9—Analytical gel filtration chromatography of 100 µl concentrated inhibitor sample. Inhibitor eluted at 10.81 ml. Column: 24 ml Superdex 75 10/30 (Pharmacia, Sweden). Eluent: 50 mM NaOAc, 100 mM NaCl, pH 5.0, Flow: 0.5 ml/minute. Fraction size: 2.0 ml.

FIG. 10—Log(MW) as function of Kav for standard proteins run on a Superdex 75 10/30.

FIG. 11—SDS PAGE of fraction 31, 32 and fraction 33 from Preparative gel filtration. Lane 1 and 3 are MW markers (Pharmacia's LMW markers, Sweden). Lane 2 and 4 are frac. 32, loaded with 10 and 25 µl respectively. Lane 6 and 8 are frac. 31, loaded with 10 and 25. Lane 7 and 9 are frac. 33, loaded with 10 and 25.

FIG. 12—Reverse Phase Chromatogram of fraction 33 from Gel. Filtration Chromatography. Chromatogram reveals four destinct peaks. Peak 3 is the xylanase inhibitor. Peak 4, 5 and 6 are sequenced and show very high homology to the Wheat protein, Serpin.

FIG. 13—MS of fraction 3 from RP—chromatography. Spectra shows one molecule having a molecular weight of 39503 Da.

FIG. 14—Reverse Phase Chromatography of carboxy methylated fraction 3 from Reverse Phase Chromatogram of fraction 33 (see FIG. 12). The chromatogram revealed two destinct peaks (fraction 2 and 3), indicating a di-peptide.

FIG. 15—MS of fraction 2 from carboxy methylated Reverse Phase Chromatography (see FIG. 14). Spectra indicate a peptide having a molecular weight of 12104 Da.

FIG. 16—MS of fraction 3 from carboxy methylated Reverse Phase Chromatography (see FIG. 14). Spectra indicate a peptide having a molecular weight of 28222 Da.

FIG. 17—IEF of fraction 33 and 34 from Preparative Gel Filtration Chromatography. Lane 2 is pI 3-10 standards, lane 3 is pI 2.5-6.5 standards, lane 4 and 5 are fraction 33 and 34—respectively, lane 6 is Trysin Inhibitor (pI 4.55), lane 7 is β-lactoglobulin (pI 5.20) and lane 8 and 9 are fraction 33 and 34—respectively. Arrows indicate destinct bands in fraction 33.

FIG. 18—pH and relative OD (from inhibitor assay) as function of fractions from Chromatofocusing Chromatography of xylanase inhibitor. As can be seen from the figure, the relative OD decreases in fraction 7, indicating inhibitor activity. This correspond to pH 9.4.

FIG. 19—Residual activity, % of four xylanases as a function of inhibitor concentration. The four xylanases used are --♦-X1, -■-X3, -x-BX, -▲-Novo.

FIG. 20—Residual activity of 980601 (coli-1), 980603 (Belase) and three mutants of 980601 (XM1, XM2 and XM3) after incubation with a flour extract.

FIG. 21—Line-weaver—Burk plot of xylanase (980601) +/− inhibitor. Substrate concentration is % azo-xylan. V is relative OD 590 from assay (where 100 is S=2%).

FIG. 22—$K_i$ for different xylanases expressed as microliter inhibitor.

FIG. 23—Inhibition of three xylanases (980601=Bac. sub. wt, 980801=X1 and 980901=*Thermomyces*) as a function of pH. The data are obtained by substrating relevant blanks.

FIG. 24—pH optimum for three xylanases (980601=BX, 980801=X1 and 980901=Novo).

FIG. 25—Spec. vol=f(xylanase×dose)

FIG. 26—Spec. vol. increase=f(xylanase×dose)

FIG. 27—Stickiness=f(xylanase×dose)

FIG. 28—Stickiness as function of different xylanase preparations and control, measured after 10 (_10) and 45 (_45) minutes resting. 980603 is purified Röhm xylanase, XM1 is xylanase mutant 1 and #2199 is Röhm's Veron Special product.

FIG. 29—Stickiness increase as function of three xylanase preparations, after 10 (_10) and 45 (_45) minutes resting. 980603 is purified Röhm xylanase, XM1 is xylanase mutant 1 and #2199 is Röhm's Veron Special product.

FIG. 30—Stickiness increase as function of two xylanase preparations, after 10 (_10) and 45 (_45) minutes resting. XM1 is xylanase mutant 1 and #2199 is Röhm's Veron Special product.

FIG. 31—Stickiness increase as function of added Endo-β-1,4-Glucanase. 1: Control dough without xylanase, 2: 7500 TXU pure Röhm xylanase/kg flour, 3: 7500 TXU pure Röhm xylanase/kg flour+158 BGU/kg Flour, 4: 15000 TXU pure Röhm xylanase/kg flour, 5: 15000 TXU pure Röhm xylanase/kg flour+316 BGU/kg Flour. Dough were measured after 10 (Stik_10) and 45 (Stik_45) minutes.

EXAMPLES

Example 1

Dough Stickiness as a Function of Different Xylanases, Doses and Resting Time

The following xylanases ability to give dough stickiness were tested.

(See also Chen, W. Z. and Hoseney, R. C. (1995). Development of an objective method for dough stickiness. Lebensmittel Wiss u.—Technol., 28, 467-473.)

Enzymes

"X1" corresponds to a purified sample of endo-β-1,4-xylanase from *Aspergillus niger*. This xylanase has an activity of 8400 TXU (15000 TXU/mg).

"Novo" corresponds to Novo Nordisk's Pentopan Mono BG from *Thermomyces*. This xylanase has an activity of 350.000 TXU (56000 TXU/mg).

"BX" corresponds to a purified sample of the new bacterial xylanase. This sample has an activity of 2000 TXU (25000 TXU/mg).

"Röhm" corresponds to Röhm GmbH's bacterial xylanase, Veron Speciel. This sample has an activity of 10500 TXU (25000 TXU/mg).

Xylanase Assay

Xylanase assays were performed according to Protocol 1

Flour

Two kinds of flour have been used in this trial: Danish flour, batch no 98022 and German flour, batch no. 98048. The water absorbtions, at 400 BU, of the two kinds of flour are 58 and 60% respectively.

Dough Preparation

Dough were prepared as described in Protocol 2. After mixing the dough rested for 10 and 45 minutes respectively at 30° C. in sealed containers.

Stickiness Measurement

Stickiness measurements were performed according to Protocol 2

Results and Discussion

Fungal Xylanases Versus New Bacterial Xylanase

The following dough were made and tested for dough stickiness after 10 and 45 minutes in flour 98048.

TABLE 1

Dough made with different doses of two fungal xylanases and one bacterial xylanase.
(Dose is calculated per kg of flour.)

| Enzyme | TXU./kg |
|---|---|
| Blank | 0 |
| X1 (980801) | 1500 |
|  | 10000 |
| Nova (#2165) | 5000 |
|  | 60000 |
| BX (980802) | 1500 |
|  | 15000 |

The dough in Table 1 gave the dough stickiness results presented in Table 2 and FIG. 1.

Table. 2

Dough Made with Different Doses of Different Xylanases Vs. Blank

The dough was rested for 10 and 45 minutes, respectively. Stickiness is given as g×s, the stickiness figure is an average of 5 determinations.

| Dough | Stickiness, g × s | Std.Dev | std.dev., % |
|---|---|---|---|
| Control, 10 min | 5.533 | 0.16 | 2.89 |
| Control, 45 min | 8.103 | 0.277 | 3.42 |
| 1500 X1, 10 min | 7.275 | 0.204 | 2.80 |
| 1500 X1, 45 min | 8.675 | 0.134 | 1.54 |
| 10000 X1, 10 min | 9.295 | 0.802 | 8.63 |
| 10000 X1, 45 min | 13.339 | 1.264 | 9.48 |
| 5000 Novo, 10 min | 6.757 | 0.218 | 3.23 |
| 5000 Novo, 45 min | 7.23 | 0.337 | 4.66 |
| 60000 Novo, 10 min | 10.972 | 0.519 | 4.73 |
| 60000 Novo, 45 min | 16.559 | 1.626 | 9.82 |
| 1500 BX, 45 min | 4.372 | 0.358 | 8.19 |
| 15000 BX, 10 min | 6.567 | 0.639 | 9.73 |
| 15000 BX, 45 min | 5.545 | 0.518 | 9.34 |

The data from Table 2 are illustrated in FIG. 1.

As can be seen from Table 2 and FIG. 1 the fungal xylanase X1 and the xylanase in the Novo product give rise to dough stickiness. The new bacterial xylanase does not give rise to the same stickiness. In addition, the stickiness seems to decrease compared with control.

New Bacterial Xylanase Vs Röhm's Bacterial Xylanase

To test the functionality of the novel bacterial xylanase compared to the bacterial xylanase in the Röhm product: Veron Special, the following dough was made (see Table 3) using flour 98022.

TABLE 3

Dough made with different doses of two bacterial xylanases.
(Dose is calculated per kg of flour.)

| Enzyme | TXU/kg |
|---|---|
| Blank | 0 |
| BX | 5000 |
|  | 15000 |
| Röhm | 5000 |
|  | 15000 |

The dough in Table 3 gave the dough stickiness results presented in Table 4 and FIG. 2.

TABLE 4

Dough made with different doses of different xylanases vs. blank. Stickiness is given as g × s, the stickiness figure is an average of 5 determinations.

| Dough | Stickiness, g × mm | Std.Dev | std.dev,. % |
|---|---|---|---|
| Control 10 min | 5.269 | 0.16 | 3.04 |
| Control 45 min | 5.484 | 0.277 | 5.05 |
| 5000 BX, 10 min | 4.443 | 0.204 | 4.59 |
| 5000 BX, 45 min | 4.474 | 0.134 | 3.00 |
| 15000 BX, 10 min | 4.791 | 0.352 | 7.35 |
| 15000 BX, 45 min | 6.288 | 0.599 | 9.53 |
| 5000 Röhm, 10 min | 5.077 | 0.218 | 4.29 |
| 5000 Röhm, 45 min | 6.757 | 0.337 | 4.99 |
| 15000 Röhm, 10 min | 7.749 | 0.519 | 6.70 |
| 15000 Röhm, 45 min | 10.98 | 0.907 | 8.26 |

The data from Table 4 are illustrated in FIG. 2.

The results show that BX (the new bacterial xylanase) gives rise to much less stickiness than the fungal xylanase tested. Moreover, it is found that the new xylanase gives rise to much less dough stickiness than the Röhm bacterial xylanase.

Example 2

Inhibitor Purification Characterisation and Effect on Xylanases

Flour

Three different kinds of flour was used in these experiments (batch 98002, 98026 and 98058). Flour batch 98002 and 98058 is Danish flour. Flour batch 98026 is German flour.

Inhibitor Extraction

The inhibitor was extracted from the flour using ice cold distilled water and stirring. One equivalent of flour was added two equivalents of ice cold distilled water. The mix was added a magnetic bar, placed in an ice bath and stirred for 20 minutes. After stirring the flour slurry was poured into centrifuge vials and centrifuged (10000 g, 4° C. and 10 minutes). The supernatant contained the xylanase inhibitor.

Inhibitor Assay

Inhibitor assays were performed according to Protocol 3

Inhibitor Isolation

After extraction of a 100 g flour sample (98026) the xylanase inhibitor was purified by the following chromatographic techniques.

Gel Filtration Chromatography (this Procedure was Run Twice)

75 ml extract was applied to a 500 ml Superdex G-25 F (Pharmacia, Sweden) column at 10 ml/minute, calibrated with 20 mM NaOAc, pH 4.25. Eluent was collected in 30 ml fractions at the same flow. All fractions were spotted for inhibitor.

Cation exchange chromatography (this Procedure was Run Twice)

The inhibitor peak collected from the gel filtration run (240 ml) was applied to a 50 ml SP Sepharose (Pharmacia, Sweden) column at 5 ml/minute. After loading, the column was washed to baseline with A buffer (20 mM NaOAc, pH 4.25). The inhibitor was eluted by a linear gradient from A to B buffer (B: A+350 mM NaCl) over 10 column volumes at the same flow. The eluate was collected in fractions of 10 ml. Every second fraction was spotted for xylanase inhibitor.

Hydrophobic Interaction Chromatography (this Procedure was Run Twice)

The inhibitor peak from the cation exchange chromatography (110 ml) was added $(NH_4)_2SO_4$ to 1.0 M and applied to a 10 ml Phenyl Sepharose HIC (Pharmacia, Sweden) column at 2 ml/minute. The inhibitor was eluted from the column by a 12 column volume linear gradient from A (20 mM NaPi, 1M $(NH_4)_2SO_4$, pH 6.0) to B (20 mM NaPi, pH 6.0). The eluate was collected in fractions of 2.5 ml. Every second fraction was spotted for xylanase inhibitor.

Preparative Gel Filtration Chromatography 5 ml inhibitor peak from HIC run was up-concentrated to 2 ml using a rotatory evaporator. This sample was loaded to a 330 ml Superdex 75 PG (Pharmacia, Sweden) column at 1 ml/minute. The buffer system used was 50 mM NaOAc, 0.2 M NaCl, pH 5.0. The eluate was collected in 5.5 ml fractions. Every second fraction was spotted for xylanase inhibitor.

Analysis of Protease Activity

To be able to determine whether the found inhibitor effect was due to an inhibitor or a protease hydrolysing the xylanase, the following experiments were carried out.

Incubation Trials 2 ml of pure xylanase, 980601 (see Endo-β-1,4-xylanases) was incubated with 0.25 ml of inhibitor extract for three hours at 40 degree C. As a control the same incubation was made with boiled (5 minutes) inhibitor extract. After incubation the samples were added 50 mM NaOAc, pH 4.5 to 2.5 ml and desalted by gel filtration on a PD-10 column (Pharmacia, Sweden), obtaining 3.5 ml sample in 50 mM NaOAc, pH 4.5.

Analysis for Hydrolysis

The two samples of pure xylanase from the incubation trials were analysed on a SOURCE 15 S column. 1 ml of the gel filtered sample was applied to the column (calibrated with A buffer: 50 mM NaOAc, pH 4.5) at 2 ml/minute. The sample was eluted with a linear gradient from A to B (B: A+1 M NaCl) over 20 column volumes and collected in 2 ml fractions. The xylanase was detected using OD 280 nm and spotted for xylanase activity in the fractions (100 μl fraction+900 μl buffer (0.1 M citric acid-0.2 M di-sodium hydrogen phosphate buffer, pH 5.0)+1 Xylazyme tab, 10 minutes, 40 degree C. Reaction terminated with 10 ml 2% TRIS, blue colour=xylanase activity).

Inhibitor Characterization
Analytical Gel Filtration Chromatography

100 µl (concentrated two times on rotatory evaporator) of the inhibitor peak from the HIC run was applied to a 24 ml Superdex 75 10/30 (Pharmacia, Sweden) at 0.5 ml/minute. Running buffer used was 50 mM NaOAc, 0.1 M NaCl, pH 5.0. Eluate was collected in fractions of 2 ml. All fractions were spotted for inhibitor.

To be able to determine the size of the inhibitor a series of known proteins were applied to the 24 ml Superdex 75 10/30 column. The conditions for this run were as described above. The standard proteins used were:

| Protein | Size, KDa. |
|---|---|
| BSA | 67 |
| Ovalbumine | 43 |
| Chymotrypsine | 25 |
| Ribonuclease A | 13.7 |

The proteins were detected at 280 nm.

SDS Page

Fractions from Preparative gel filtration chromatography were added SDS sample buffer (prepared according to NOVEX protocol), boiled for three minutes and loaded on a 8-16% PAGE gel (NOVEX). The gel was stained according to NOVEX's protocol for silver staining. As molecular weight markers, Pharmacia's LMW markers were used.

Iso Electric Focusing (IEF)

To determine the pI of the native inhibitor, a sample of purified inhibitor (fraction 33 from 330 ml Superdex 75 PG) was loaded on a pH 3-10 IEF GEL (NOVEX). The gel was run according to manufactors protocol. Using Pharmacia's (Sweden) Broad pI kit, 3.5-9.3 as standards. The gel was stained with coomassie brilliant blue, according to producers protocol.

Chromatofocusing Chromatography

A sample of fraction 33 from Preparative gelfiltration chromatography, was gelfiltrated to water. 100 µl desaltet sample was loaded on a Mono P HR 515 (Pharmacia, Sweden). Starting conditions was obtained with 25 mM ethanolamin-HCl, pH 9.4. The column was eluted with Poly buffer 96: Water in a 1:10 ratio. pH adjusted to 6.0 (flow: 0.5 ml/min; fraction size: 0.5 ml). After elution with Poly buffer 96, the column was further eluted with Poly buffer 74: water in a 1:10 ratio. pH adjusted to 3.80 (flow: 0.5 ml/min; fraction size: 0.5 ml).

All fractions was pH measured and spotted for xylanase inhibitor, using Protocol 3.

Amino Acid Sequence

A sample (obtained from fraction 33 from 330 ml Superdex 75 PG) of pure inhibitor from preparative purification was used. 200 µl was loaded on a C4 Reverse Phase column (Applied Biosystems). The buffer system used was A: 0.1% TFA in water and B: 0.1% TFA in 100% Acetonitrile. Inhibitor peak from this run was carboxymethylated and rerun on C4 column again. In this way two inhibitor peptides, of interest, were obtained. These were N-terminal sequenced. Furthermore, the peptides were digested with Lys-C. The obtained peptides were recovered using reverse phase chromatography and amino acid sequenced.

To verify sequences obtained by amino acid sequencing, a small fraction of the sample of interest, was analysed using MS (Voyager).

Inhibitor Kinetics

Inhibitor assays were performed according to Protocol 5. In this respect, for the preliminary inhibitor characterisation studies, the xylanase used was 980601, diluted to 40 TXU/ml and the inhibitor was extracted from flour 98002. For $K_I$ determinations, the following xylanases were used: 980601, 980603, 980801, 980901, 980903, 980906 and 980907, diluted to approx. 40 TXU/ml. The inhibitor used for $K_I$ determinations was extracted from flour 98058.

Determination of Inhibition as a Function of pH

These experiments were carried out as described in Protocol 3 with the following modifications. Besides using 650 µl buffer (0.1 M citric acid-0.2 M di-sodium hydrogen phosphate) pH 5.0 in the assay, the assay was also carried out using the same buffer system at pH: 4, 6 and 7.

Endo-β-1,4-xylanases

The following xylanase preparations were used:

980601 (BX): Purified preparation of Danisco's new bacterial xylanase expressed in *E. coli*. (1225 TXU/ml)

980603 (Röhm): Purified preparation of Frimond's Belase xylanase (identical to Röhm's) (1050 TXU/ml)

980801 (X1): Purified X1 from *Aspergillus niger* (8400 TXU/g)

980802 (Röhm): Purified preparation of Frimond's Belase xylanase (identical to Röhm's) (265 TXU/ml)

980901 (Novo): Purified preparation of *Thermomyces xylanase* from Novo's Pentopan mono BG (2900 TXU/ml)

980903 (XM1): Purified mutant of *Bacillus* sub. wild type xylanase expressed in *E. coli*. (1375 TXU/ml)

980906 (XM3): Purified mutant of *Bacillus* sub. wild type xylanase expressed in *E. coil*. (1775 TXU/ml)

980907 (XM2): Purified mutant of *Bacillus* sub. wild type xylanase expressed in *E. coli*. (100 TXU/ml)

9535 (X3): Purified xylanase, X3 from *Aspergillus niger* (6490 TXU/ml)

Results and Discussion

Inhibitor Extraction for Isolation and Characterisation 100 g flour (98026) was extracted. After centrifugation a supernatant of 150 ml was obtained. The presence of inhibitor was checked in this extract (Table 5) and found positive.

TABLE 5

Residual activity as a function of +/- addition of inhibitor extract from wheat flour (98026).
The xylanase used is 980601.

|  | −inhibitor | +inhibitor | Residual activity, % |
|---|---|---|---|
| OD 590 | 0.675 | 0.165 | 24.44 |

Inhibitor Isolation 75 ml of the inhibitor extract was loaded on a 500 ml gel filtration column (FIG. 3). After spotting for the inhibitor, it could be located in fractions [4-11] (Table 6).

TABLE 6

Fractions from gel filtration chromatography of 75 ml inhibitor extract assayed for xylanase inhibitor. OD run 1 respectively 2 correspond to the two runs that were performed on the column. Inhibitor was found present in fractions [4-11]. These fractions were pooled for each run, giving two times 240 ml.

| Fraction no. | OD run 1 | OD run 2 |
|---|---|---|
| 1 | 0.674 |  |
| 2 | 0.665 |  |

TABLE 6-continued

Fractions from gel filtration chromatography of 75 ml inhibitor extract assayed for xylanase inhibitor. OD run 1 respectively 2 correspond to the two runs that were performed on the column. Inhibitor was found present in fractions [4–11]. These fractions were pooled for each run, giving two times 240 ml.

| Fraction no. | OD run 1 | OD run 2 |
|---|---|---|
| 3 | 0.652 | |
| 4 | 0.618 | 0.476 |
| 5 | 0.388 | 0.166 |
| 6 | 0.186 | 0.126 |
| 7 | 0.188 | 0.18 |
| 8 | 0.277 | 0.217 |
| 9 | 0.381 | 0.231 |
| 10 | 0.406 | 0.246 |
| 11 | 0.395 | 0.435 |
| 12 | 0.725 | |
| 13 | 0.683 | |
| 14 | 0.762 | |
| 15 | 0.737 | |

The pool of the inhibitor peak in both runs on the gel filtration column, was approx. 240 ml.

Two times, a 240 ml pool from gelfiltration was applied to the cation exchanger. The flow through was found negative for inhibitor. As can be seen from FIG. 4 and Table 7 the inhibitor bound to the column and eluted at approx. 750 mM NaCl.

TABLE 7

Fractions from cation exchange chromatography of 240 ml gel filtered inhibitor extract assayed for the presence of xylanase inhibitor. OD run 1 respectively 2 correspond to the two runs that were performed on the column. Inhibitor was found present in fractions [44–54].

| Fraction no. | OD run 1 | OD run 2 |
|---|---|---|
| 40 | 0.476 | 0.624 |
| 42 | 0.407 | 0.58 |
| 44 | 0.404 | 0.398 |
| 46 | 0.22 | 0.137 |
| 48 | 0.144 | 0.107 |
| 50 | 0.198 | 0.126 |
| 52 | 0.302 | 0.208 |
| 54 | 0.395 | 0.435 |
| 56 | 0.457 | 0.495 |
| 58 | 0.463 | 0.606 |

The pool of inhibitor from the ion exchange runs was 110 ml from each run. These two pooled fractions were added $(NH_4)_2SO_4$ to 1.0 M and applied to the HIC column in two runs. The flow through was spotted for inhibitor and found negative. As can be seen from FIG. 5 and Table 8 all inhibitor bound to the column and a good separation was obtained.

The analysis of the fractions from the HIC chromatography is shown in Table 8.

TABLE 8

Fractions from HIC chromatography of 147 ml inhibitor extract assayed for xylanase inhibitor. OD run 1 respectively 2 corresponds to the two runs that were performed on the column. Inhibitor was found present in fractions [15–23].

| Fraction no. | OD run 1 | OD run 2 |
|---|---|---|
| Blank | 0.469 | 0.659 |
| 12 | 0.462 | 0.622 |
| 14 | 0.486 | 0.555 |
| 16 | 0.202 | 0.188 |
| 18 | 0.1 | 0.118 |
| 20 | 0.102 | 0.146 |
| 22 | 0.242 | 0.193 |
| 24 | 0.392 | 0.502 |
| 26 | 0.485 | 0.6 |

Fractions 17 and 18 from the HIC chromatography were concentrated approx. two times and applied to a preparative gel filtration column (FIG. 6).

The analysis of the fractions from the preparative gel filtration is shown in Table 9.

TABLE 9

Fractions from Preparative gel filtration chromatography of 2 ml concentrated inhibitor sample assayed for the presence of xylanase inhibitor. Inhibitor was found present in fractions [31–33].

| Fraction no. | OD 590 nm |
|---|---|
| 26 | 0.738 |
| 28 | 0.774 |
| 30 | 0.645 |
| 32 | 0.117 |
| 34 | 0.705 |
| 36 | 0.749 |
| 38 | 0.754 |
| 40 | 0.761 |
| 42 | 0.769 |

Analysis of Protease Activity

Based on the above assay of the xylanase inhibitor, it can not be ruled out that the decrease in xylanase activity, when mixed with the flour extract, is not due to a proteolytic hydrolysis of the xylanase. Therefore, a purified xylanase was incubated with an "inhibitor" extract. As can be seen from FIGS. 7 and 8, no hydrolysis seems to occur. There is a little more background in the chromatogram with active inhibitor (FIG. 8). However, this back-ground corresponds to the chromatogram of the inhibitor alone (chromatogram of inhibitor not shown). The difference in background must be due to precipitation in the boiled inhibitor sample.

Inhibitor Characterisation

Analytical Gel Filtration Chromatography

100 µl two times concentrated inhibitor sample from fraction 18 in the second HIC run was applied to a 24 ml analytical Superdex 75 10/30 (Pharmacia, Sweden) (FIG. 9). The eluate was collected in fractions of 2 ml. These fractions were assayed for the xylanase inhibitor (Table 10).

TABLE 10

Fractions from analytical gel filtration chromatography of 100 µl concentrated inhibitor sample assayed for the presence of xylanase inhibitor. Inhibitor was found present in fractions [6–7].

| Fraction no. | OD 590 nm |
|---|---|
| Blank | 0.613 |
| 6 | 0.233 |

TABLE 10-continued

Fractions from analytical gel filtration chromatography of 100 μl concentrated inhibitor sample assayed for the presence of xylanase inhibitor. Inhibitor was found present in fractions [6–7].

| Fraction no. | OD 590 nm |
|---|---|
| 7 | 0.304 |
| 8 | 0.51 |
| 9 | 0.569 |
| 10 | 0.565 |
| 11 | 0.652 |

After the gel filtration of the up-concentrated inhibitor sample a mix of four standard molecular weight proteins was applied to the column, using the exactly same procedure (chromatogram not shown). In table 11 the molecular weights and the elution times for the proteins are summarised.

TABLE 11

Standard proteins used for determination of the MW of the inhibitor. Abbreviations and equations used are explained below the table.

| Std. protein | Ve, ml | Kav* | MW, kDa | log (MW) |
|---|---|---|---|---|
| BSA | 9.46 | 0.059508 | 67 | 1.826075 |
| Ovalbumin | 10.38 | 0.119017 | 43 | 1.633468 |
| Chymotrypsin | 12.49 | 0.255498 | 25 | 1.39794 |
| Ribonuklease A | 13.49 | 0.320181 | 13.7 | 1.136721 |

*Kav = (Ve − Vo)/(Vt − Vo)
Where:
Ve = ret. Time, ml =
Vo = void vol., ml = 8.54
Vt = 24 ml = 24

Plotting the log (MW) as a function of Kav. It is possible to obtain an equation and estimating the molecular size of an unknown molecule (FIG. 10).

Using the equation obtained in FIG. 10 and the retention time for the inhibitor, it is possible to calculate the molecular size of the inhibitor:

$$MW, kDa = 10^{(-2,4485 \times kav + 1.9602)}$$
$$= 10^{(-2,4485 \times 0.173559 + 1.9602)}$$
$$= 10^{1.5352}$$
$$= 34.29$$

The molecular weight found for the inhibitor was higher than we expected according to Rouau and Surget (1998, Evidence for the presence of a Pentosanase Inhibitor in Wheat Flour. Journal of Cereal Science. 28: 63-70)), the MW of the molecule is approx. 8 KDa. The MW obtained by gel filtration could be explained by aggregation of several inhibitor molecules. To study this further an SDS PAGE gel was run of fractions 31, 32 and 33 from the preparative gel filtration chromatography (FIG. 11). As can be seen from this gel, three bands appears in the lanas loaded with purified inhibitor sample. These band correspond to proteins with MW's of approx. 40, 30 and 10 kDa.

MW Determination Using MS

A sample of fraction 33 from preparative gel filtration of the inhibitor was desalted using the Presorb system and 5 volumes of 20 mM Acetic acid. 200 μl was loaded on a C4 Reverse Phase column (Applied Biosystems). From this run, three peaks was obtained. One of these peaks (peak 3) was clearly dominating, and thought to be the inhibitor (FIG. 12). The other peaks from the run have also been sequenced. From the sequence obtained it can be concluded that they are all originating from the same wheat protein, Serpin, and are not identical to the inhibitor (peak 3). Therefore peak 3 is concluded to be the xylanase inhibitor of interest. This peak was further characterised using MS (Voyager).

MS spectra analysis revealed a signal corresponding to a protein of 39503 Da, using sinapic acid as matrix (FIG. 13).

As mentioned above, the SDS PAGE gel indicated three bands. One band at approx. 10 kDa, one at approx. 30 kDa and a band at approx. 40 kDa. To explain the results seen from SDS-PAGE, the pure dominant fraction was collected, lyophilised and carboxymethylated and then rerun on the C4 column, using same conditions as mentioned above.

The fraction obtained by this rerun (FIG. 14) was analysed using MS. As can be seen from FIGS. 15 and 16, the MW of these poly-peptides are 12104 and 28222 Da.

Without wishing to be bound by theory we believe that the xylanase inhibitor is either a native di-peptide (MW 39503 Da) or it is denaturated and reduced (two peptides with MW 12104 and 28222 Da—respectively) during the analytical process.

Determination of pI for the Xylanase Inhibitor Using IEF and Chromatofocusing Chromatography The IEF gel showed three bands in the alkaline area (approx. 9.3, 8.6 and 8.2—respectively) and three bands in the acidic area (approx. 5.1, 5.3 and 5.5—respectively) (FIG. 17). Based on these results alone it may not be feasible to determine the pI of the native xylanase inhibitor. In this regard, we knew from the sequencing results, that the sample only contained the xylanase inhibitor and three fragments of Serpin, of approx. 4500 Da. A theoretical calculation of the pI for Serpin is 5.58 and the pI calculated on the fragment we obtained by sequencing gives pI 5.46 (using Swiss Prot programmes). This could indicate that the three acidic bands seen on the gel, are the three peaks of Serpin seen with Reverse Phase Chromatography (FIG. 12), and the three alkaline bands are the three different forms of the xylanase inhibitor, i.e. the native di-peptide form and the two peptides (as indicated by sequencing).

As can be seen from the Chromatofocusing Chromatography results presented in FIG. 18, the xylanase inhibitor does not bind to the column under the given conditions. This could mean that the native xylanase inhibitor has a pI of 8.5 or even higher. Hence, it would seem that the assumptions presented above, namely that there are three alkaline bands on the IEF gel and so there could be three possible forms of the xylanase inhibitor, may be correct.

In conclusion, we believe that the native xylanase inhibitor has pI in the interval 8.0-9.5. Within this interval, there are three bands. These three bands probably correspond to the xylanase inhibitor possibly existing in three forms (see the results determined using IEF). In this respect, in using IEF, the protein runs as a native protein but that some di-peptide proteins may be partly damaged by this technique, thereby giving rise to more than one band.

Sequence Data

The two peptides forming the inhibitor, were sequenced giving N-terminal and internal sequences. The results are presented in the attached sequence listings as SEQ ID No.s 13-19.

The sequences making up the first chain (chain A) are shown as SEQ ID No.s 13 and 14. The sequences making up the second chain (chain B) are shown as SEQ ID No.s 15 to 19.

A data base search for homology to the sequenced polypeptides came out negative. Neither of the poly-peptides have been sequenced or described before.

Effect of Inhibitor on Different Xylanases

Several trials have been carried out to study the inhibition of different xylanases. First we believed that the decrease in xylanase activity was due to a proteolytic activity in the extract. Therefore, different xylanases were incubated with different volumes of "inhibitor" extract (FIG. 19). The xylanases were found to be inhibited to different extends. What we also found was that there seemed to be an increase in inhibition as a function of "inhibitor" concentration.

The results illustrated in FIG. 19 could indicate that the decrease was due to proteolysis or inhibitor. However, time course experiments with constant xylanase and inhibitor concentrations and the above mentioned results under "Analysis for protease activity", did not show decreased activity as a function of time. To be able to distinguish between protease and inhibitor, real kinetics has to be made (see "inhibitor kinetics").

Two *Bacillus subtilis* xylanases have been studied very closely regarding their baking performance. These xylanases differed a little in their functionality, meaning that one gave a slightly higher specific volume when baked in identical doses. One explanation could be different inhibition of their activity in the flour. An experiment was therefore performed to examine this. The experiment has been repeated twice, using two different kinds of flour as source for the inhibitor (Table 14).

TABLE 14

Inhibition of two xylanases (980601 and 980603) by inhibitor extracted from two kinds of flour (98002 and 98026). Inhibition is calculated as % inhibition and as % residual activity, compared to blank.

|  |  | Flour |  |  |
| --- | --- | --- | --- | --- |
|  |  | 98002 | 98026 | Avg |
| Inhibation, % | 980601 | 67.03 | 75.04 |  |
|  | 980603 | 60.76 | 61.33 |  |
| Rest act., % | 980601 | 32.97 | 24.96 | 28.96 |
|  | 980603 | 39.24 | 38.67 | 38.96 |
| Difference, % |  |  |  | 25.65 |

The trial shows that the two xylanases are inhibited to different extents by the inhibitor. The xylanases differ in only six amino acids.

Based on 980601, three xylanase mutants have been made (XM1, XM2 and XM3). These mutants have been analysed for inhibition (FIG. 20).

As can be seen from FIG. 20 the three mutants differ in residual activity, meaning that they are inhibited to different degrees by the xylanase inhibitor. Four (BX, Röhm, XM1 and XM3) of the five xylanases have the same specific activity (approx. 25000 TXU/mg protein). XM2 is expected to have the same specific activity.

The difference in inhibition between XM1 and XM2 is approx. 250% (the residual activity of XM1 is 2.5 times higher than the rest activity of XM2). This difference is due to one amino acid. Amino acid 122 in XM2 is changed from arginine to asparagine, introducing less positive charge near the active site.

Inhibitor Kinetics

Simple preliminary kinetics were performed. Just to be able to determine whether the inhibitor is competitive or non-competitive.

Different amounts of substrate were incubated with a constant xylanase- and inhibitor concentration (FIG. 21).

As can be seen from FIG. 21, $V_{max}$ for both xylanase with and without inhibitor is approx. 1.19. This indicates that the inhibition is competitive.

Since the preliminary inhibitor experiments described above, indicating difference in $K_i$ between the xylanases studied. The real $K_i$ for several xylanases were determined. As can be seen from the data in FIG. 22, the $K_i$ values do differ significantly between the xylanases. This confirms the results indicated by the simple preliminary inhibitor characterisation.

Inhibition as a Function of pH

A simple spot for xylanase inhibitor at a different pH revealed that there seemed to be an effect of pH on the inhibition of the xylanases. Therefore, an experiment was set up to examine this effect. As can be seen from FIG. 23 the inhibition of the xylanases are influenced by pH. FIG. 24 illustrates the pH optima for the xylanases. If these two curves are compared, we see the highest inhibition at the pH optimum for the xylanase, except for the pH 4 measurement of the Novo xylanase (980901).

To determine whether the inhibition ratios measured in the assays reported here are relevant in the dough, some calculations can be made:

| Inhibitor extraction | |
| --- | --- |
| Gram flour: | 6 |
| ml water: | 12 |
| g flour/ml: | 0.5 |
| g flour in assay: | 0.05 |
| Xylanase solution | |
| TXU/ml: | 12 |
| TXU/ml in assay: | 3 |
| Inhibitor:xylanase ratios | |
| TXU/kg flour: | 60000 in inhibitor assay |
| TXU/kg flour: | 3000 in bakery applications |

From the above calculations, the inhibitor:xylanase ratio in the assay can be calculated to be 20 times lower in the assay than in dough. This can only mean that the xylanase must be much more inhibited in dough. However, the mobility and water activity is much lower in dough and this might influence the inhibition.

Summary Discussion

Wheat flour contains endogeneous endo-β-1,4-xylanase inhibitor. The inhibitor can be extracted from wheat flour by a simple extraction using water, meaning that the inhibitor is water soluble. The inhibitor was purified using gel filtration-, ion exchange- and hydrophobic interaction chromatographic techniques.

Characterisation of the purified inhibitor, using analytical gel filtration chromatography, SDS PAGE, reverse phase chromatography and MS, revealed a poly-peptide of approx. 40 KDa. This poly-peptide turned out to be a di-peptide, containing two peptides with molecular weights of 12104 and 28222 Da, respectively. The purified inhibitor (more precise the two peptides) was N-terminal sequenced, followed by digestion and sequencing of peptides obtained.

The preliminary experiment with the inhibitor indicated that the decrease in xylanase activity found could be due to proteolysis. However, analysis of incubation trials (xylanase+ inhibitor) and kinetics on the inhibitor indicated that the observed decrease in xylanase activity was due to a competitive inhibitor.

Inhibitor experiments using several xylanases indicate differences in sensibility towards the inhibitor. Some xylanases are inhibited almost 100% by the inhibitor (at a lower inhibitor:xylanase ratio than present in the flour). By varying pH in the inhibitor assay it turns out the inhibition is highly dependent on the pH in the assay. Examining the xylanase mutants revealed that changing one amino acid can mean a 250% decrease in inhibition.

To confirm the results described above, $K_i$ values were determined for several xylanases. The results showed different $K_i$'s depending on the xylanase used, confirming the differences in resistance towards the inhibitor as function of xylanase seen in preliminary results.

Example 3

Baking Trials

The data below are from a baking trail with the XM1 mutant. The data show that this novel xylanase mutant is clearly superior to BX (*Bacillus subtilis* wild type) based on volume. Based on stickiness measurement there are no significant difference between the two xylanases Enzymes 980902 (BX): Purified *Bacillus* sub. wild type xylanase expressed in *E. coli*. (2000 TXU/ml)

980903 (XM1): Purified mutant of *Bacillus* sub. wild type xylanase expressed in *E. coli*. (1375 TXU/ml)

Flour

Danish flour, batch 98022.

Baking Test (Hard Crust Rolls)

Flour 2000 g, dry yeast 40 g, sugar 32 g, salt 32 g, GRINDSTED™ Panodan A2020 4 g, water 400 Brabender Units+4% were kneaded in a Hobart mixer with hook for 2 minutes low speed and 9 minutes high speed. The dough temperature was 26° C. The dough was scaled to 1350 gram. Resting 10 minutes at 30° C. followed by moulding on a Fortuna moulder. Proofing 45 minutes at 34° C., 85% RH. Baked in a Bago-oven 18 minutes 220° C. and steamed 12 seconds.

After cooling the rolls were scaled and their volume measured by the rape seed deplacement method.

$$\text{Specific volume} = \frac{\text{volume of the bread, ml}}{\text{weight of the bread, g}}$$

Stickiness Measurement

Stickiness measurement was performed according to Protocol 2.

As can be seen from Table 15 the novel xylanase mutant (XM1) gives rise to significant higher bread volume increase than BX.

TABLE 15

Bread volume increase (ml/gram) and stickiness (g × s) as function of two xylanases (BX and XM1) applied at different dosages.

| Sample | Dose, TXU/kg | Stickiness, g × s | Specific vol., ml/g | Spec. vol. increase, % |
|---|---|---|---|---|
| BX | 2000 | 6.00 | 6.03 | 2.55 |
| BX | 5000 | 6.60 | 6.49 | 10.37 |

TABLE 15-continued

Bread volume increase (ml/gram) and stickiness (g × s) as function of two xylanases (BX and XM1) applied at different dosages.

| Sample | Dose, TXU/kg | Stickiness, g × s | Specific vol., ml/g | Spec. vol. increase, % |
|---|---|---|---|---|
| BX | 8000 | 5.00 | 6.77 | 15.14 |
| BX | 12000 | 7.00 | 6.72 | 14.29 |
| XM1 | 2000 | 4.30 | 6.60 | 12.24 |
| XM1 | 5000 | 6.20 | 6.88 | 17.01 |
| XM1 | 8000 | 6.20 | 7.06 | 20.07 |
| XM1 | 12000 | 6.90 | 7.32 | 24.49 |
| Control | 0 | 4.50 | 5.88 | — |

The data are shown in FIGS. 25, 26 and 27.

Example 4

Dough Stickiness as a Function of XM1, the Röhm Veron Special Xylanase and a Purified Version of the Röhm Veron Special Xylanase To determine whether the novel xylanase, XM1 gives more or less sticky dough than Röhm's Veron Special xylanase (and a purified version hereof) dough were prepared and stickiness as function of xylanase was determined.

Flour

Danish flour, batch 98022 was used.

Dough Preparation

Dough were prepared as described in Protocol 2. After mixing the dough rested for 10 and 45 minutes, respectively, in sealed containers before stickiness measurement.

Stickiness Measurement

Stickiness measurements were performed according to Protocol 2.

Enzymes 980903 (XM1): Purified mutant of *Bacillus* sub. wild type xylanase expressed in *E. coli*. (1375 TXU/ml)

2199: the Röhm Veron Special xylanase (10500 TXU/g)

980603 (Röhm): Purified preparation of Frimond's Belase xylanase (identical to Röhm's) (1050 TXU/ml)

The following doughs were made (Table 16):

TABLE 16

Dough made for determination of stickiness

| Xylanase | Dosage, TXU/kg flour |
|---|---|
| 980603 (Purified Rohm xylanase) | 15.000 |
| Control | 0 |
| XM1 | 15.000 |
| #2199 (Rohm's Veron Special) | 15.000 |

The dough in Table 16 gave the stickiness results in Table 17.

TABLE 17

Results from stickiness measurements on dough prepared with Purified Rohm xylanase, control, XM1 and the Rohm Veron Special xylanase.

| Xylanase | TXU/kg flour | Leavening time, min. | Stickiness, g × s | Stickiness increase, g × s |
|---|---|---|---|---|
| 980603 | 15.000 | 10 | 7.22 | 2.22 |
| 980603 | 15.000 | 45 | 10.15 | 4.08 |

TABLE 17-continued

Results from stickiness measurements on dough
prepared with Purified Rohm xylanase, control,
XM1 and the Rohm Veron Special xylanase.

| Xylanase | TXU/kg flour | Leavening time, min. | Stickiness, g × s | Stickiness increase, g × s |
|---|---|---|---|---|
| Control | 0 | 10 | 5.00 | 0 |
| Control | 0 | 45 | 6.09 | 0 |
| XM1 | 15.000 | 10 | 6.61 | 1.61 |
| XM1 | 15.000 | 45 | 9.64 | 3.55 |
| #2199 | 15.000 | 10 | 8.57 | 3.57 |
| #2199 | 15.000 | 45 | 12.14 | 6.05 |

The data are shown in FIGS. 28, 29 and 30.

The increase in stickiness using the XM1 is lower than the stickiness increase with the purified Röhm xylanase. The stickiness increase obtained using the unpurified Röhm xylanase is much higher.

Example 5

Dough Stickiness as a Function of Bacterial Endo-β-1,4-Glucanase

The results in the following are from an experiment designed to study the ability of bacterial Endo-β-1,4-Glucanase to give stickiness.

Enzymes 981102-1 (Xyl): Correspond to a purified preparation of Röhm's bacterial xylanase from the product Veron Special. The preparation is pure xylanase and do not contain any Endo-β-1,4-Glucanase (350 TXU/ml)

981102-2 (Xyl+Gluc): Correspond to a purified preparation of Röhm's bacterial xylanase from the product Veron Special, containing Endo-β-1,4-Glucanase (900 TXU/ml+19 BGU/ml)

Xylanase Assay

Xylanase assays were performed according to Protocol 1

Glucanase Assay

Glucanase assays were performed according to Protocol 4

Flour

Danish flour, batch no 98058 was used. The water absorbtions, at 400 BU is 60%.

Dough Preparation

Dough were prepared as described in Protocol 2. After mixing the dough rested for 10 and 45 minutes respectively at 30° C. in sealed containers.

Stickiness Measurement

Stickiness measurements were performed according to Protocol 2

The dough listed in Table 18 were prepared and examined for stickiness.

TABLE 18

Dough prepared for examining stickiness

| Dough No. | Dough | TXU/kg flour | BGU/kg flour |
|---|---|---|---|
| 1 | Control | 0 | 0 |
| 2 | TXU | 7500 | 0 |
| 3 | TXU + BGU | 7500 | 158 |
| 4 | TXU | 15000 | 0 |
| 5 | TXU + BGU | 15000 | 316 |

The dough listed in Table 18 gave the stickiness results in Table 19.

TABLE 19

Stickiness results from dough with xylanase
and xylanase + glucanase
Dough No. refers to the dough No. in Table 18
Stik_10 indicate results from stickiness
measurements after 10 minutes
Stik_45 indicate measurements
after 45 minutes of resting

| Dough No. | Stik_10, g × s | std.dev | Stik_45, g × s | std.dev |
|---|---|---|---|---|
| 1 | 4.5 | 0.342 | 5.11 | 0.552 |
| 2 | 5.29 | 0.619 | 8.62 | 0.607 |
| 3 | 5.47 | 0.663 | 9.38 | 0.832 |
| 4 | 8.61 | 0.408 | 9.15 | 0.418 |
| 5 | 8.73 | 0.35 | 10.19 | 0.857 |

As can be seen from Table 19, the Endo-β-1,4-Glucanase addition to the dough increases the stickiness of the dough. The results from Table 19 are illustrated in FIG. 31.

Summary

In summary the present invention provides and the Examples show inter alia:

a. The isolation of an endogenous endo-β-1,4-xylanase inhibitor from wheat flour.

b. The characterisation of an endogenous endo-β-1,4-xylanase inhibitor isolated from wheat flour.

c. The characterisation of the effect of endogenous endo-β-1,4-xylanase inhibitor on different xylanases.

d. A means for selecting xylanases not detrimentally affected by endogenous endo-β-1,4-xylanase inhibitor.

e. A means for selecting xylanases which are not detrimentally affected by endo-β-1,4-xylanase inhibitors.

f. Xylanases that provide dough exhibiting favourable volume and acceptable stickiness than when compared to doughs comprising fungal xylanases.

g. A method for screening xylanases and/or mutating the same using an endogenous endo-β-1,4-xylanase inhibitor, and the use of those xylanases or mutants thereof in the manufacture of doughs.

h. A foodstuff prepared with the xylanases of the present invention.

All publications mentioned in the above specification are herein incorporated by reference. Various modifications and variations of the described methods and system of the present invention will be apparent to those skilled in the art without departing from the scope and spirit of the present invention. Although the present invention has been d scribed in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A dough for making a bakery product comprising a polypeptide expressed from the nucleotide sequence of SEQ ID NO: 6, wherein said dough for making a bakery product is suitable for use in a foodstuff.

2. The dough for making a bakery product of claim 1, wherein said polypeptide does not contain a leader sequence.

3. The dough for making a bakery product of claim 1, wherein said polypeptide has the amino acid sequence of SEQ ID NO: 5.

4. The dough for making a bakery product of claim 2, wherein said polypeptide has the amino acid sequence of amino acids 29-213 of SEQ ID NO: 5.

5. A dough for making a bakery product prepared by incorporating a bacterial xylanase comprising a polypeptide expressed from the nucleotide sequence of SEQ ID NO: 6, whereby the resultant dough is less sticky than an otherwise identical dough prepared by incorporating a fungal xylanase instead of said bacterial xylanase.

6. The dough of claim 5, wherein said polypeptide does not contain a leader sequence.

7. The dough of claim 5, wherein said polypeptide has the amino acid of SEQ ID NO: 5.

8. The dough of claim 7, wherein said polypeptide has the amino acid sequence of amino acids 29-213 of SEQ ID NO: 5.

9. A bakery product prepared by baking the dough of claim 5.

10. The dough of claim 5, comprising wheat flour, water and a bacterial xylanase expressed from the nucleotide sequence of SEQ ID NO: 6.

11. The dough of claim 10, wherein said bacterial xylanase is from a *Bacillus subtilis* strain.

12. The dough of claim 10, wherein said bacterial xylanase is free of detrimental levels of glucanase enzymes.

13. The dough of claim 10, further comprising yeast.

14. A bakery product prepared by baking the dough of claim 13.

15. A method for reducing stickiness of a dough for making a bakery product comprising incorporating a bacterial xylanase expressed from the nucleotide sequence of SEQ ID NO: 6 in the dough, wherein said dough for making a bakery product is suitable for use in a foodstuff and whereby the resultant dough is less sticky than an otherwise identical dough prepared by incorporating a fungal xylanase instead of said bacterial xylanase.

16. The method of claim 15, further comprising measuring the stickiness of said dough by placing 4 g of the dough in a dough stickiness cell;
extruding the dough 1 mm;
pressing a probe into the extruded dough at a set force of 40 g;
raising the probe;
measuring a peak force and a distance at which the dough releases from the probe.

* * * * *